United States Patent
Fredriksson et al.

(10) Patent No.: US 11,628,224 B2
(45) Date of Patent: Apr. 18, 2023

(54) THERAPEUTIC AGENTS TARGETING CLPTM1

(71) Applicant: GENAGON THERAPEUTICS AB, Solna (SE)

(72) Inventors: Johan Erik Simon Fredriksson, Bromma (SE); Olof Andries Blokzijl, Stockholm (SE)

(73) Assignee: GENAGON THERAPEUTICS AB, Solna (SE)

( * ) Notice: Subject to any disclaimer, the term of this patent is extended or adjusted under 35 U.S.C. 154(b) by 585 days.

(21) Appl. No.: 16/477,389

(22) PCT Filed: Jan. 12, 2018

(86) PCT No.: PCT/EP2018/050773
§ 371 (c)(1),
(2) Date: Jul. 11, 2019

(87) PCT Pub. No.: WO2018/130657
PCT Pub. Date: Jul. 19, 2018

(65) Prior Publication Data
US 2019/0343962 A1    Nov. 14, 2019

(30) Foreign Application Priority Data
Jan. 12, 2017   (GB) ..................................... 1700553

(51) Int. Cl.
*A61K 47/68*   (2017.01)
*C07K 16/30*   (2006.01)
*A61K 39/395*   (2006.01)
*A61K 39/00*   (2006.01)

(52) U.S. Cl.
CPC ...... *A61K 47/6849* (2017.08); *A61K 47/6855* (2017.08); *A61K 47/6865* (2017.08); *C07K 16/3015* (2013.01); *A61K 2039/505* (2013.01); *A61K 2039/585* (2013.01); *C07K 16/30* (2013.01); *C07K 2317/73* (2013.01)

(58) Field of Classification Search
CPC ............ A61K 47/6849; A61K 47/6855; A61K 47/6865; A61K 2039/505; A61K 2039/585; A61K 47/6809; A61K 47/6851; A61K 2039/5156; C07K 16/3015; C07K 16/30; C07K 2317/73; C07K 2317/70; C07K 2319/33; G01N 33/53
See application file for complete search history.

(56) References Cited

U.S. PATENT DOCUMENTS

| | | | |
|---|---|---|---|
| 5,827,642 A | 10/1998 | Riddell et al. | |
| 6,040,177 A | 3/2000 | Riddell et al. | |
| 6,797,514 B2 | 9/2004 | Berenson et al. | |
| 6,824,780 B1 | 11/2004 | Devaux et al. | |
| 6,867,041 B2 | 3/2005 | Berenson et al. | |
| 6,905,874 B2 | 6/2005 | Berenson et al. | |
| 8,168,586 B1 | 5/2012 | Fang et al. | |
| 8,524,238 B2 | 9/2013 | Fang et al. | |
| 2014/0099310 A1 | 4/2014 | Fang et al. | |
| 2016/0333083 A1* | 11/2016 | James | C07K 16/3023 |
| 2019/0256592 A1* | 8/2019 | Blokzijl | A61P 1/00 |

FOREIGN PATENT DOCUMENTS

| | | | |
|---|---|---|---|
| WO | 2012/079000 A1 | 6/2012 | |
| WO | 2012/129514 A1 | 9/2012 | |
| WO | 2013/126746 A2 | 8/2013 | |
| WO | 2013/166110 A1 | 11/2013 | |
| WO | 2015/108719 A1 | 7/2015 | |
| WO | WO-2015197446 A1 * | 12/2015 | ............. A61K 38/18 |
| WO | 2017/013188 A1 | 1/2017 | |

OTHER PUBLICATIONS

Macrophage Inhibitory Cytokine 1 Reduces Cell Adhesion and Induces Apoptosis in Prostate Cancer Cells Tao Liu, Asne R. Bauskin, John Zaunders, David A. Brown, Susan Pankurst, Pamela J. Russell and Samuel N. Breit Cancer Res Aug. 15, 2003 (63) (16) 5034-5040 (Year: 2003).*
Rudikoff et al (Proc. Natl. Acad. Sci. USA, 79(6): 1979-1983, Mar. 1982) (Year: 1982).*
Paul, Fundamental Immunology, 3rd Edition, 1993, pp. 292-295 (Year: 1993).*
Colman P. M. (Research in Immunology, 145:33-36, 1994) (Year: 1994).*
Edwards et al. 2003. The remarkable flexibility of the human antibody repertoire; isolation of over one thousand different antibodies to a single protein, BlyS. Journal of Molecular Biology 334:103-118 (Year: 2003).*
Murphy et al. (Journal of Immunological Methods, vol. 463, p. 127-133, 2018) (Year: 2018).*
Inoue K, Hatano K, Hanamatsu Y, Saigo C, Kito Y, Bunai K, Shibata T, Takeuchi T. Pathobiological role of cleft palate transmembrane protein 1 family proteins in oral squamous cell carcinoma. J Cancer Res Clin Oncol. Apr. 2019;145(4):851-859 (Year: 2019).*
Lewis AL, Chaft J, Girotra M, Fischer GW. Immune checkpoint inhibitors: a narrative review of considerations for the anaesthesiologist. Br J Anaesth. Mar. 2020;124(3):251-260 (Year: 2020).*
Weiner, Louis M. et al., Antibody-Based Immunotherapy of Cancer, Cell, vol. 148, pp. 1081-1084 (Mar. 16, 2012).

(Continued)

*Primary Examiner* — Hong Sang
*Assistant Examiner* — Sung Min Yoon
(74) *Attorney, Agent, or Firm* — Porter Wright Morris & Arthur LLP

(57) ABSTRACT

A therapeutic agent capable of binding to the receptor CLPTM1 at the surface of an immune cell and modulating its activity for use in modulating the activity of the immune system to treat cancer, wherein the therapeutic agent is capable of inhibiting the growth and/or viability of an anti-inflammatory and/or immunosuppressive cell to relieve unwanted or deleterious immunosuppression by eliminating anti-inflammatory and/or immunosuppressive immune cells; and/or the therapeutic agent is capable of stimulating an antigen-presenting immune cell and acts to stimulate antigen-presenting immune cells to activate an anti-cancer immune response.

24 Claims, 19 Drawing Sheets
Specification includes a Sequence Listing.

(56) References Cited

OTHER PUBLICATIONS

Official Office Action from European Application No. 18702617.4 dated Apr. 21, 2020.

Albertoni, Michele et al., Anoxia induces macrophage inhibitory cytokine-1 (MIC-1) in glioblastoma cells independently of p53 and HIF-1, Oncogene, vol. 21, pp. 4212-4219 (2002).

Biggadike, Keith et al., Discovery of 6-Amino-2-{[(1S)-1-methylbutyl] oxy} -9- [5-(1-piperidinyl) pentyl]-7,9-dihydro-8H-purin-8-one (GSK2245035), a Highly Potent and Selective Intranasal Toll-like Receptor 7 Agonist for the Treatment of Asthma, J. Med. Chem., vol. 59, pp. 1711-1726 (2016).

Bruhns, Pierre, Specificity and affinity of human Fc receptors and their polymorphic variants for human IgG subclasses, BLOOD, vol. 113, No. 16, (Apr. 2009).

Creelan, Benjamin C., Update on Immune Checkpoint Inhibitors in Lung Cancer, Cancer Control, vol. 21, No. 1, pp. 1-10 (Jan. 2014).

Diamantis, Nikolaos et al., Antibody-drug conjugates—an emerging class of cancer treatment, British Journal of Cancer, vol. 114, pp. 362-367 (2016).

Dronca, Roxana S. et al., Immunomodulatory Antibody Therapy of Cancer: The Closer, the Better, Clinical Cancer Research, vol. 21, No. 5, pp. 944-947 (Published OnlineFirst Oct. 28, 2014).

Folgueira, Maria Aparecida Azevedo Koike et al., Gene Expression Profile Associated with Response to Doxorubicin-Based Therapy in Breast Cancer, Clin Cancer Res, vol. 11, No. 20, pp. 7434-7443 (Oct. 15, 2005).

Gadd, Adam J. R. et al., Targeted Activation of Toll-Like Receptors: Conjugation of a Toll-Like Receptor 7 Agonist to a Monoclonal Antibody Maintains Antigen Binding and Specificity, Bioconjugate Chem., vol. 26, pp. 1743-1752 (Aug. 19, 2015).

Gong, Jiang-Hong et al., Characterization of a Human Cell Line (NK-92) with Phenotypical and Functional Characteristics of Activated Natural Killer Cells, Leukemia, vol. 8, No. 4, pp. 652-658 (Apr. 1994).

Hanson, Melissa C. et al., Nanoparticulate STING agonists are potent lymph node-targeted vaccine adjuvants, The Journal of Clinical Investigation, vol. 125, No. 6, pp. 2532-2546 (Jun. 2015).

Jiang, Xu-Rong et al., Advances in the assessment and control of the effector functions of therapeutic antibodies, Drug Discovery, vol. 10, pp. 101-110 (Feb. 2011).

Khalil, Danny N. et al., The New Era of Cancer Immunotherapy: Manipulating T-Cell Activity to Overcome Malignancy, Advances in Cancer Research, vol. 128, pp. 1-68 (Jan. 1, 2015).

Khalil, Danny N., et al., The future of cancer treatment: immunomodulation, CARS and combination immunotherapy, Clinical Oncology, vol. 13, No. 5, pp. 273-291 (Mar. 15, 2016).

Kim, Kwang-Kyu, Macrophage inhibitory cytokine-1 activates AKT and ERK-1/2 via the transactivation of ErbB2 in human breast and gastric cancer cells, Carcinogenesis, vol. 29, No. 4, pp. 704-712 (2008).

Lazar, Greg A. et al., Engineered antibody Fc variants with enhanced effector function, PNAS, vol. 103, No. 11, pp. 4005-4010 (Mar. 14, 2006).

Lee, Susan J. et al., Immunomodulator therapy: Monoclonal antibodies, fusion proteins, cytokines, and immunoglobulins, J Allergy Clin Immunol, vol. 125, No. 2, pp. S314-S323 (Aug. 2009).

Eggermont, Loek J. et al., Towards efficient cancer immunotherapy: advances in developing artificial antigen-presenting cells, Trends in Biotechnology, vol. 32, No. 9, pp. 456-465 (Sep. 2014).

Lupton, Stephen D. et al., Dominant Positive and Negative Selection Using a Hygromycin Phosphotransferase-Thymidine Kinase Fusion Gene, Molecular and Cellular Biology, vol. 11, No. 6, pp. 3374-3378 (Jun. 1991).

Müller, Philipp et al., Microtubule-Depolymerizing Agents Used in Antibody-Drug Conjugates Induce Antitumor Immunity by Stimulation of Dendritic Cells, Cancer Immunol Res; vol. 2, No. 8, pp. 741-756 (Aug. 2014).

Müller, Philipp et al., Trastuzumab emtansine (T-DM1) renders HER2+ breast cancer highly susceptible to CTLA-4/PD-1 blockade, Science Translational Medicine, vol. 7, No. 315, pp. 1-16 (Nov. 25, 2015).

Natsume, Akito et al., Fucose Removal from Complex-Type Oligosaccharide Enhances the Antibody-Dependent Cellular Cytotoxicity of Single-Gene-Encoded Bispecific Antibody Comprising of Two Single-Chain Antibodies Linked to the Antibody Constant Region, J. Biochem, vol. 140, pp. 359-368 (2006).

Neuzillet, Cindy et al., Targeting the TGFβ pathway for cancer therapy, Pharmacology & Therapeutics, vol. 147, pp. 22-31 (2015).

Overdijk, Marije B. et al., Crosstalk between Human IgG Isotypes and Murine Effector Cells, J Immunol, vol. 189, pp. 3430-3438 (prepublished online Sep. 5, 2012).

Puskás, László G. et al., Novel Anti-CRR9/CLPTM1L Antibodies with Antitumorigenic Activity Inhibit Cell Surface Accumulation, PI3K Interaction, and Survival Signaling, Mol Cancer Ther, vol. 15, No. 5, pp. 985-997 (online Mar. 3, 2016).

Salazar, Andres M. et al., Therapeutic In Situ Autovaccination against Solid Cancers with Intratumoral Poly-ICLC: Case Report, Hypothesis, and Clinical Trial, Cancer Immunol Res, vol. 2, No. 8, pp. 720-725 (Aug. 2014).

Santa Cruz Biotechnology Inc., Cataloge, CLPTM1 (G-7): sc-374619 (2013).

Schmidt, M. et al., Cytokine and Ig-production by CG-containing sequences with phosphorodiester backbone and dumbbell-shape, Allergy, vol. 61, pp. 56-63 (2006).

Scott, Andrew M. et al., Monoclonal antibodies in cancer therapy, Cancer Immunity, vol. 12, pp. 14-21 (May 1, 2012).

Selby, Mark J. et al., Anti-CTLA-4 Antibodies of IgG2a Isotype Enhance Antitumor Activity through Reduction of Intratumoral Regulatory T Cells, Cancer Immunol Res, vol. 1, No. 1, pp. 32-43 (Jul. 2013).

Shields, Robert L. et al., High Resolution Mapping of the Binding Site on Human IgG1 for FcγRI, FcγRII, FcγRIII and FcRn and Design of IgG1 Variants with Improved Binding to the FcγR, The Journal of Biological Chemistry, vol. 276, No. 9, pp. 6591-6604 (Mar. 2, 2001).

Shields, Robert L. et al., Lack of Fucose on Human IgG1 N-Linked Oligosaccharide Improves Binding to Human FcγRIII and Antibody-dependent Cellular Toxicity, The Journal of Biological Chemistry, vol. 277, No. 30, pp. 26733-26740 (Jul. 26, 2002).

Sivestri, Ida et al., A Perspective of Immunotherapy for Prostate Cancer, Cancers, vol. 8, No. 64, pp. 1-20 (2016).

Stewart, Ross et al., A variant human IgG1-Fc mediates improved ADCC, Protein Engineering, Design & Selection, vol. 24, No. 9, pp. 671-678 (2011).

Stewart, Ross et al., The role of Fc gamma receptors in the activity of immunomodulatory antibodies for cancer, Journal for ImmunoTherapy of Cancer, vol. 2, No. 29, pp. 1-10 (2014).

Stieglmaier PhD, Julia et al., Utilizing the BiTE (bispecific T-cell engager) platform for immunotherapy of cancer, Expert Opinion on Biological Therapy, vol. 15, No. 8, pp. 1093-1099 (published online: May 13, 2015).

Storz, Ulrich, IP Issues of Therapeutic Antibodies, SpringerBriefs in Biotech Patents, pp. 1-17 (2012).

Takeuchi, Tamotsu et al., Characterization of a 50 kDa surface membrane protein on thymic stromal cells as an important factor for early T cell development, International Immunology, vol. 7, No. 4, pp. 583-590 (1995).

Takeuchi, T. et al., Transgenic expression of a novel thymic epithelial cell antigen stimulates abberant development of thymocytes, J Immunol, vol. 159, pp. 726-733 (1997).

Vogel et al., Efficient generation of human natural killer cell lines by viral transformation, Leukemia, vol. 28, pp. 192-195(2014).

Wälchli, Sebastien et al., A Practical Approach to T-Cell Receptor Cloning and Expression, Plos One, vol. 6, No. 11 pp. 1-11 (Nov. 2011).

Williams, Carly Bess et al., Tumor-associated macrophages: unwitting accomplices in breast cancer malignancy, Breast Cancer, vol. 2, pp. 1-12 (published online Jan. 20, 2016).

(56) References Cited

OTHER PUBLICATIONS

Wilson, David R. et al., Biodegradable STING agonist nanoparticles for enhanced cancer immunotherapy, Nanomedicine, vol. 14, No. 2, pp. 237-246 (Feb. 14, 2018).
Wu, Tom Y.-H, Strategies for designing synthetic immune agonists, Immunology, vol. 148, pp. 315-325 (2016).
Yamane-Ohnuki, Naoko et al., Production of therapeutic antibodies with controlled fucosylation, mAbs, vol. 1, No. 3, pp. 230-236 (May/Jun. 2009).
Zhang, Yue et al., High-Infiltration of Tumor-Associated Macrophages Predicts Unfavorable Clinical Outcome for Node-Negative Breast Cancer, Plos One, vol. 8, No. 9 (Sep. 2013).
UKIPO Search Report, pp. 1-5, (dated Aug. 29, 2017).

\* cited by examiner

QAGPGGAPRVASRNL (SEQ ID NO: 78)
GGAPRVASRNLFPKD (SEQ ID NO: 79)
RVASRNLFPKDTLMN (SEQ ID NO: 80)
RNLFPKDTLMNLHVY (SEQ ID NO: 81)
PKDTLMNLHVYISEH (SEQ ID NO: 82)
LMNLHVYISEHEHFT (SEQ ID NO: 83)
HVYISEHEHFTDFNA (SEQ ID NO: 84)
SEHEHFTDFNATSAL (SEQ ID NO: 85)

VPPPLDQYVKFDAVS (SEQ ID NO: 86)
　　LDQYVKFDAVSGDYY (SEQ ID NO: 87)
　　　　VKFDAVSGDYYPIIY (SEQ ID NO: 88)
　　　　　　AVSGDYYPIIYFNDY (SEQ ID NO: 89)
　　　　　　　　DYYPIIYFNDYWNLQ (SEQ ID NO: 90)
　　　　　　　　　　IIYFNDYWNLQKDYY (SEQ ID NO: 91)
　　　　　　　　　　　　NDYWNLQKDYYPINE (SEQ ID NO: 92)
　　　　　　　　　　　　　　NLQKDYYPINESLAS (SEQ ID NO: 93)

Figure 8

| Celltype | Flow cytometry markers | 4T1 (breast) % | MFI | B16 (melanoma) % | MFI | CT26 (colon) % | MFI | LLC (lung) % | MFI | Healthy spleen % | MFI |
|---|---|---|---|---|---|---|---|---|---|---|---|
| CD8 DCs | CD45+CD11c+MHCII+CD11b- | 24 | 552 | 0 | 0 | 38 | 264 | 4 | 66 | 0 | 0 |
| CD11b DCs | CD45+CD11c+MHCII+CD11b+ | 20 | 1903 | 67 | 4698 | 61 | 6401 | 18 | 2447 | 0 | 0 |
| pDCs | CD45+CD11c+PDCA-1+ | 47 | 3688 | 67 | 8878 | 41 | 6378 | 20 | 3378 | 0 | 0 |
| Neutrophils | CD45+CD11b+Ly6Ghi Ly6Cint | 70 | 526 | 9 | 21 | 88 | 563 | 43 | 301 | 0 | 0 |
| PMN-MDSC | CD45+CD11b+Ly6G+Ly6C | 1 | 383 | 0 | 0 | 10 | 355 | 16 | 107 | 0 | 0 |
| M-MDSC | CD45+CD11b+Ly6G-Ly6Chi | 85 | 1938 | 65 | 2054 | 79 | 2027 | 53 | 507 | 0 | 0 |
| Macrophages | CD45+CD11b+F480+ | 28 | 866 | 31 | 149 | 69 | 3068 | 35 | 1068 | 0 | 0 |
| B cells | CD45+B220+ | 78 | 660 | 20 | 106 | 58 | 272 | 11 | 275 | 0 | 0 |
| CD4 T cells | CD45+CD4+ | 43 | 321 | 41 | 186 | 39 | 240 | 31 | 110 | 0 | 0 |
| Tregs | CD45+CD4+FoxP3+ | 47 | 233 | 49 | 215 | 77 | 265 | 48 | 119 | 0 | 0 |
| Teffs | CD45+CD4+CD44+ | 43 | 222 | 36 | 175 | 61 | 198 | 35 | 100 | 0 | 0 |
| CD8 T cells | CD45+CD8+ | 46 | 285 | 48 | 170 | 64 | 269 | 27 | 696 | 0 | 0 |
| NK cells | CD45+NK1.1 | 39 | 3171 | 5 | 191 | 60 | 4787 | 6 | 98 | 0 | 0 |
| Tumor cells | CD45- | 48 | 493 | 80 | 1188 | 84 | 1430 | 43 | 338 | 0 | 0 |

SEQUENCE LISTING

<160> NUMBER OF SEQ ID NOS: 94

<210> SEQ ID NO 1
<211> LENGTH: 669
<212> TYPE: PRT
<213> ORGANISM: Homo sapiens

<400> SEQUENCE: 1

```
Met Ala Ala Gln Glu Ala Asp Gly Ala Arg Ser Ala Val Val Ala
1               5                   10                  15

Ala Gly Gly Ser Ser Gly Gln Val Thr Ser Asn Gly Ser Ile Gly
                20                  25                  30

Arg Asp Pro Ala Glu Thr Gln Pro Gln Asn Pro Pro Ala Gln Pro
                35                  40                  45

Ala Pro Asn Ala Trp Gln Val Ile Lys Gly Val Leu Phe Arg Ile Phe
        50                  55                  60

Ile Ile Trp Ala Ile Ser Ser Trp Phe Arg Arg Gly Pro Ala Pro Gln
65                  70                  75                  80

Asp Gln Ala Gly Pro Gly Gly Ala Pro Arg Val Ala Ser Arg Asn Leu
                85                  90                  95

Phe Pro Lys Asp Thr Leu Met Asn Leu His Val Tyr Ile Ser Glu His
                100                 105                 110

Glu His Phe Thr Asp Phe Asn Ala Thr Ser Ala Leu Phe Trp Glu Gln
                115                 120                 125

His Asp Leu Val Tyr Gly Asp Trp Thr Ser Gly Glu Asn Ser Asp Gly
                130                 135                 140

Cys Tyr Glu His Phe Ala Glu Leu Asp Ile Pro Gln Ser Val Gln Gln
145                 150                 155                 160

Asn Gly Ser Ile Tyr Ile His Val Tyr Phe Thr Lys Ser Gly Phe His
                165                 170                 175

Pro Asp Pro Arg Gln Lys Ala Leu Tyr Arg Arg Leu Ala Thr Val His
                180                 185                 190

Met Ser Arg Met Ile Asn Lys Tyr Lys Arg Arg Phe Gln Lys Thr
                195                 200                 205

Lys Asn Leu Leu Thr Gly Glu Thr Glu Ala Asp Pro Glu Met Ile Lys
                210                 215                 220

Arg Ala Glu Asp Tyr Gly Pro Val Glu Val Ile Ser His Trp His Pro
225                 230                 235                 240

Asn Ile Thr Ile Asn Ile Val Asp Asp His Thr Pro Trp Val Lys Gly
                245                 250                 255

Ser Val Pro Pro Leu Asp Gln Tyr Val Lys Phe Asp Ala Val Ser
                260                 265                 270

Gly Asp Tyr Tyr Pro Ile Ile Tyr Phe Asn Asp Tyr Trp Asn Leu Gln
            275                 280                 285

Lys Asp Tyr Tyr Pro Ile Asn Glu Ser Leu Ala Ser Leu Pro Leu Arg
            290                 295                 300

Val Ser Phe Cys Pro Leu Ser Leu Trp Arg Trp Gln Leu Tyr Ala Ala
305                 310                 315                 320

Gln Ser Thr Lys Ser Pro Trp Asn Phe Leu Gly Asp Glu Leu Tyr Glu
                325                 330                 335

Gln Ser Asp Glu Glu Asp Ser Val Lys Val Ala Leu Leu Glu Thr
                340                 345                 350

Asn Pro Tyr Leu Leu Ala Leu Thr Ile Ile Val Ser Ile Val His Ser
                355                 360                 365
```

```
Val Phe Glu Phe Leu Ala Phe Lys Asn Asp Ile Gln Phe Trp Asn Ser
    370                 375                 380

Arg Gln Ser Leu Glu Gly Leu Ser Val Arg Ser Val Phe Phe Gly Val
385                 390                 395                 400

Phe Gln Ser Phe Val Leu Leu Tyr Ile Leu Asp Asn Glu Thr Asn
                405                 410                 415

Phe Val Val Gln Val Ser Val Phe Ile Gly Val Leu Ile Asp Leu Trp
                420                 425                 430

Lys Ile Thr Lys Val Met Asp Val Arg Leu Asp Arg Glu His Arg Val
                435                 440                 445

Ala Gly Ile Phe Pro Arg Leu Ser Phe Lys Asp Lys Ser Thr Tyr Ile
                450                 455                 460

Glu Ser Ser Thr Lys Val Tyr Asp Asp Met Ala Phe Arg Tyr Leu Ser
465                 470                 475                 480

Trp Ile Leu Phe Pro Leu Leu Gly Cys Tyr Ala Val Tyr Ser Leu Leu
                485                 490                 495

Tyr Leu Glu His Lys Gly Trp Tyr Ser Trp Val Leu Ser Met Leu Tyr
                500                 505                 510

Gly Phe Leu Leu Thr Phe Gly Phe Ile Thr Met Thr Pro Gln Leu Phe
                515                 520                 525

Ile Asn Tyr Lys Leu Lys Ser Val Ala His Leu Pro Trp Arg Met Leu
                530                 535                 540

Thr Tyr Lys Ala Leu Asn Thr Phe Ile Asp Asp Leu Phe Ala Phe Val
545                 550                 555                 560

Ile Lys Met Pro Val Met Tyr Arg Ile Gly Cys Leu Arg Asp Asp Val
                565                 570                 575

Val Phe Phe Ile Tyr Leu Tyr Gln Arg Trp Ile Tyr Arg Val Asp Pro
                580                 585                 590

Thr Arg Val Asn Glu Phe Gly Met Ser Gly Glu Asp Pro Thr Ala Ala
                595                 600                 605

Ala Pro Val Ala Glu Val Pro Thr Ala Ala Gly Ala Leu Thr Pro Thr
                610                 615                 620

Pro Ala Pro Thr Thr Thr Thr Ala Thr Arg Glu Glu Ala Ser Thr Ser
625                 630                 635                 640

Leu Pro Thr Lys Pro Thr Gln Gly Ala Ser Ser Ala Ser Glu Pro Gln
                645                 650                 655

Glu Ala Pro Pro Lys Pro Ala Glu Asp Lys Lys Lys Asp
                660                 665

<210> SEQ ID NO 2
<211> LENGTH: 353
<212> TYPE: PRT
<213> ORGANISM: Homo sapiens

<400> SEQUENCE: 2

Ala Ala Ala Gln Glu Ala Asp Gly Ala Arg Ser Ala Val Val Ala Ala
1               5                   10                  15

Gly Gly Gly Ser Ser Gly Gln Val Thr Ser Asn Gly Ser Ile Gly Arg
                20                  25                  30

Asp Pro Pro Ala Glu Thr Gln Pro Gln Asn Pro Ala Gln Pro Ala
                35                  40                  45

Pro Asn Ala Trp Gln Val Ile Lys Gly Val Leu Phe Arg Ile Phe Ile
                50                  55                  60

Ile Trp Ala Ile Ser Ser Trp Phe Arg Arg Gly Pro Ala Pro Gln Asp
65                  70                  75                  80
```

```
Gln Ala Gly Pro Gly Gly Ala Pro Arg Val Ala Ser Arg Asn Leu Phe
                85                  90                  95
Pro Lys Asp Thr Leu Met Asn Leu His Val Tyr Ile Ser Glu His Glu
            100                 105                 110
His Phe Thr Asp Phe Asn Ala Thr Ser Ala Leu Phe Trp Gln His
        115                 120                 125
Asp Leu Val Tyr Gly Asp Trp Thr Ser Gly Glu Asn Ser Asp Gly Cys
    130                 135                 140
Tyr Glu His Phe Ala Glu Leu Asp Ile Pro Gln Ser Val Gln Gln Asn
145                 150                 155                 160
Gly Ser Ile Tyr Ile His Val Tyr Phe Thr Lys Ser Gly Phe His Pro
                165                 170                 175
Asp Pro Arg Gln Lys Ala Leu Tyr Arg Arg Leu Ala Thr Val His Met
            180                 185                 190
Ser Arg Met Ile Asn Lys Tyr Lys Arg Arg Phe Gln Lys Thr Lys
        195                 200                 205
Asn Leu Leu Thr Gly Glu Thr Glu Ala Asp Pro Glu Met Ile Lys Arg
    210                 215                 220
Ala Glu Asp Tyr Gly Pro Val Glu Val Ile Ser His Trp His Pro Asn
225                 230                 235                 240
Ile Thr Ile Asn Ile Val Asp Asp His Thr Pro Trp Val Lys Gly Ser
                245                 250                 255
Val Pro Pro Pro Leu Asp Gln Tyr Val Lys Phe Asp Ala Val Ser Gly
            260                 265                 270
Asp Tyr Tyr Pro Ile Ile Tyr Phe Asn Asp Tyr Trp Asn Leu Gln Lys
        275                 280                 285
Asp Tyr Tyr Pro Ile Asn Glu Ser Leu Ala Ser Leu Pro Leu Arg Val
    290                 295                 300
Ser Phe Cys Pro Leu Ser Leu Trp Arg Trp Gln Leu Tyr Ala Ala Gln
305                 310                 315                 320
Ser Thr Lys Ser Pro Trp Asn Phe Leu Gly Asp Glu Leu Tyr Glu Gln
                325                 330                 335
Ser Asp Glu Glu Gln Asp Ser Val Lys Val Ala Leu Leu Glu Thr Asn
            340                 345                 350
Pro

<210> SEQ ID NO 3
<211> LENGTH: 7
<212> TYPE: PRT
<213> ORGANISM: Homo sapiens

<400> SEQUENCE: 3

Tyr Ile Ser Glu His Glu His
1               5

<210> SEQ ID NO 4
<211> LENGTH: 6
<212> TYPE: PRT
<213> ORGANISM: Homo sapiens

<400> SEQUENCE: 4

Leu Phe Trp Glu Gln His
1               5

<210> SEQ ID NO 5
<211> LENGTH: 31
```

<212> TYPE: PRT
<213> ORGANISM: Homo sapiens

<400> SEQUENCE: 5

Tyr Ile Ser Glu His Glu His Phe Thr Asp Phe Asn Ala Thr Ser Ala
1               5                   10                  15

Leu Phe Trp Glu Gln His Asp Leu Val Tyr Gly Asp Trp Thr Ser
            20                  25                  30

<210> SEQ ID NO 6
<211> LENGTH: 16
<212> TYPE: PRT
<213> ORGANISM: Homo sapiens

<400> SEQUENCE: 6

Ala Leu Phe Trp Glu Gln His Asp Leu Val Tyr Gly Asp Trp Thr Ser
1               5                   10                  15

<210> SEQ ID NO 7
<211> LENGTH: 9
<212> TYPE: PRT
<213> ORGANISM: Homo sapiens

<400> SEQUENCE: 7

Tyr Phe Asn Asp Tyr Trp Asn Leu Gln
1               5

<210> SEQ ID NO 8
<211> LENGTH: 3
<212> TYPE: PRT
<213> ORGANISM: Homo sapiens

<400> SEQUENCE: 8

Pro Lys Asp
1

<210> SEQ ID NO 9
<211> LENGTH: 4
<212> TYPE: PRT
<213> ORGANISM: Homo sapiens

<400> SEQUENCE: 9

Pro Lys Asp Thr
1

<210> SEQ ID NO 10
<211> LENGTH: 14
<212> TYPE: PRT
<213> ORGANISM: Homo sapiens

<400> SEQUENCE: 10

Ala Pro Arg Val Ala Ser Arg Asn Leu Phe Pro Lys Asp Thr
1               5                   10

<210> SEQ ID NO 11
<211> LENGTH: 13
<212> TYPE: PRT
<213> ORGANISM: Homo sapiens

<400> SEQUENCE: 11

Pro Arg Val Ala Ser Arg Asn Leu Phe Pro Lys Asp Thr
1               5                   10

<210> SEQ ID NO 12

```
<211> LENGTH: 12
<212> TYPE: PRT
<213> ORGANISM: Homo sapiens

<400> SEQUENCE: 12

Arg Val Ala Ser Arg Asn Leu Phe Pro Lys Asp Thr
1               5                   10

<210> SEQ ID NO 13
<211> LENGTH: 11
<212> TYPE: PRT
<213> ORGANISM: Homo sapiens

<400> SEQUENCE: 13

Val Ala Ser Arg Asn Leu Phe Pro Lys Asp Thr
1               5                   10

<210> SEQ ID NO 14
<211> LENGTH: 10
<212> TYPE: PRT
<213> ORGANISM: Homo sapiens

<400> SEQUENCE: 14

Ala Ser Arg Asn Leu Phe Pro Lys Asp Thr
1               5                   10

<210> SEQ ID NO 15
<211> LENGTH: 9
<212> TYPE: PRT
<213> ORGANISM: Homo sapiens

<400> SEQUENCE: 15

Ser Arg Asn Leu Phe Pro Lys Asp Thr
1               5

<210> SEQ ID NO 16
<211> LENGTH: 8
<212> TYPE: PRT
<213> ORGANISM: Homo sapiens

<400> SEQUENCE: 16

Arg Asn Leu Phe Pro Lys Asp Thr
1               5

<210> SEQ ID NO 17
<211> LENGTH: 7
<212> TYPE: PRT
<213> ORGANISM: Homo sapiens

<400> SEQUENCE: 17

Asn Leu Phe Pro Lys Asp Thr
1               5

<210> SEQ ID NO 18
<211> LENGTH: 6
<212> TYPE: PRT
<213> ORGANISM: Homo sapiens

<400> SEQUENCE: 18

Leu Phe Pro Lys Asp Thr
1               5

<210> SEQ ID NO 19
<211> LENGTH: 5
<212> TYPE: PRT
```

<213> ORGANISM: Homo sapiens

<400> SEQUENCE: 19

Phe Pro Lys Asp Thr
1               5

<210> SEQ ID NO 20
<211> LENGTH: 14
<212> TYPE: PRT
<213> ORGANISM: Homo sapiens

<400> SEQUENCE: 20

Pro Arg Val Ala Ser Arg Asn Leu Phe Pro Lys Asp Thr Leu
1               5                   10

<210> SEQ ID NO 21
<211> LENGTH: 13
<212> TYPE: PRT
<213> ORGANISM: Homo sapiens

<400> SEQUENCE: 21

Val Ala Ser Arg Asn Leu Phe Pro Lys Asp Thr Leu Met
1               5                   10

<210> SEQ ID NO 22
<211> LENGTH: 13
<212> TYPE: PRT
<213> ORGANISM: Homo sapiens

<400> SEQUENCE: 22

Ala Ser Arg Asn Leu Phe Pro Lys Asp Thr Leu Met Asn
1               5                   10

<210> SEQ ID NO 23
<211> LENGTH: 13
<212> TYPE: PRT
<213> ORGANISM: Homo sapiens

<400> SEQUENCE: 23

Ser Arg Asn Leu Phe Pro Lys Asp Thr Leu Met Asn Leu
1               5                   10

<210> SEQ ID NO 24
<211> LENGTH: 13
<212> TYPE: PRT
<213> ORGANISM: Homo sapiens

<400> SEQUENCE: 24

Arg Asn Leu Phe Pro Lys Asp Thr Leu Met Asn Leu His
1               5                   10

<210> SEQ ID NO 25
<211> LENGTH: 13
<212> TYPE: PRT
<213> ORGANISM: Homo sapiens

<400> SEQUENCE: 25

Asn Leu Phe Pro Lys Asp Thr Leu Met Asn Leu His Val
1               5                   10

<210> SEQ ID NO 26
<211> LENGTH: 13
<212> TYPE: PRT
<213> ORGANISM: Homo sapiens

<400> SEQUENCE: 26

Leu Phe Pro Lys Asp Thr Leu Met Asn Leu His Val Tyr
1               5                   10

<210> SEQ ID NO 27
<211> LENGTH: 13
<212> TYPE: PRT
<213> ORGANISM: Homo sapiens

<400> SEQUENCE: 27

Phe Pro Lys Asp Thr Leu Met Asn Leu His Val Tyr Ile
1               5                   10

<210> SEQ ID NO 28
<211> LENGTH: 13
<212> TYPE: PRT
<213> ORGANISM: Homo sapiens

<400> SEQUENCE: 28

Pro Lys Asp Thr Leu Met Asn Leu His Val Tyr Ile Ser
1               5                   10

<210> SEQ ID NO 29
<211> LENGTH: 12
<212> TYPE: PRT
<213> ORGANISM: Homo sapiens

<400> SEQUENCE: 29

Pro Lys Asp Thr Leu Met Asn Leu His Val Tyr Ile
1               5                   10

<210> SEQ ID NO 30
<211> LENGTH: 11
<212> TYPE: PRT
<213> ORGANISM: Homo sapiens

<400> SEQUENCE: 30

Pro Lys Asp Thr Leu Met Asn Leu His Val Tyr
1               5                   10

<210> SEQ ID NO 31
<211> LENGTH: 10
<212> TYPE: PRT
<213> ORGANISM: Homo sapiens

<400> SEQUENCE: 31

Pro Lys Asp Thr Leu Met Asn Leu His Val
1               5                   10

<210> SEQ ID NO 32
<211> LENGTH: 9
<212> TYPE: PRT
<213> ORGANISM: Homo sapiens

<400> SEQUENCE: 32

Pro Lys Asp Thr Leu Met Asn Leu His
1               5

<210> SEQ ID NO 33
<211> LENGTH: 8
<212> TYPE: PRT
<213> ORGANISM: Homo sapiens

<400> SEQUENCE: 33

Pro Lys Asp Thr Leu Met Asn Leu
1               5

<210> SEQ ID NO 34
<211> LENGTH: 7
<212> TYPE: PRT
<213> ORGANISM: Homo sapiens

<400> SEQUENCE: 34

Pro Lys Asp Thr Leu Met Asn
1               5

<210> SEQ ID NO 35
<211> LENGTH: 6
<212> TYPE: PRT
<213> ORGANISM: Homo sapiens

<400> SEQUENCE: 35

Pro Lys Asp Thr Leu Met
1               5

<210> SEQ ID NO 36
<211> LENGTH: 5
<212> TYPE: PRT
<213> ORGANISM: Homo sapiens

<400> SEQUENCE: 36

Pro Lys Asp Thr Leu
1               5

<210> SEQ ID NO 37
<211> LENGTH: 15
<212> TYPE: PRT
<213> ORGANISM: Homo sapiens

<400> SEQUENCE: 37

Gly Gly Ala Pro Arg Val Ala Ser Arg Asn Leu Phe Pro Lys Asp
1               5                   10                  15

<210> SEQ ID NO 38
<211> LENGTH: 15
<212> TYPE: PRT
<213> ORGANISM: Homo sapiens

<400> SEQUENCE: 38

Arg Val Ala Ser Arg Asn Leu Phe Pro Lys Asp Thr Leu Met Asn
1               5                   10                  15

<210> SEQ ID NO 39
<211> LENGTH: 15
<212> TYPE: PRT
<213> ORGANISM: Homo sapiens

<400> SEQUENCE: 39

Arg Asn Leu Phe Pro Lys Asp Thr Leu Met Asn Leu His Val Thr
1               5                   10                  15

<210> SEQ ID NO 40
<211> LENGTH: 15
<212> TYPE: PRT
<213> ORGANISM: Homo sapiens

<400> SEQUENCE: 40

Pro Leu Asp Thr Leu Met Asp Leu His Val Tyr Ile Ser Glu His
1               5                   10                  15

```
<210> SEQ ID NO 41
<211> LENGTH: 15
<212> TYPE: PRT
<213> ORGANISM: Homo sapiens

<400> SEQUENCE: 41

Leu Asp Gln Tyr Val Lys Phe Asp Ala Val Ser Gly Asp Tyr Tyr
1               5                   10                  15

<210> SEQ ID NO 42
<211> LENGTH: 15
<212> TYPE: PRT
<213> ORGANISM: Homo sapiens

<400> SEQUENCE: 42

Leu Asp Gln Tyr Val Lys Phe Asp Ala Val Ser Gly Asp Tyr Tyr
1               5                   10                  15

<210> SEQ ID NO 43
<211> LENGTH: 15
<212> TYPE: PRT
<213> ORGANISM: Homo sapiens

<400> SEQUENCE: 43

Ala Val Ser Gly Asp Tyr Tyr Pro Ile Ile Tyr Phe Asn Asp Tyr
1               5                   10                  15

<210> SEQ ID NO 44
<211> LENGTH: 15
<212> TYPE: PRT
<213> ORGANISM: Homo sapiens

<400> SEQUENCE: 44

Asp Tyr Tyr Pro Ile Ile Tyr Phe Asn Asp Tyr Trp Asn Leu Gln
1               5                   10                  15

<210> SEQ ID NO 45
<211> LENGTH: 15
<212> TYPE: PRT
<213> ORGANISM: Homo sapiens

<400> SEQUENCE: 45

Ile Ile Tyr Phe Asn Asp Tyr Trp Asn Leu Gln Lys Asp Tyr Tyr
1               5                   10                  15

<210> SEQ ID NO 46
<211> LENGTH: 15
<212> TYPE: PRT
<213> ORGANISM: Homo sapiens

<400> SEQUENCE: 46

Asn Asp Tyr Trp Asn Leu Gln Lys Asp Tyr Tyr Pro Ile Asn Glu
1               5                   10                  15

<210> SEQ ID NO 47
<211> LENGTH: 15
<212> TYPE: PRT
<213> ORGANISM: Homo sapiens

<400> SEQUENCE: 47

Asn Leu Gln Lys Asp Tyr Tyr Pro Ile Asn Glu Ser Leu Ala Ser
1               5                   10                  15
```

```
<210> SEQ ID NO 48
<211> LENGTH: 15
<212> TYPE: PRT
<213> ORGANISM: Homo sapiens

<400> SEQUENCE: 48

Pro Trp Asn Phe Leu Gly Asp Glu Leu Tyr Glu Gln Ser Asp Glu
1               5                   10                  15

<210> SEQ ID NO 49
<211> LENGTH: 14
<212> TYPE: PRT
<213> ORGANISM: Homo sapiens

<400> SEQUENCE: 49

Asp Glu Glu Gln Asp Ser Val Lys Val Ala Leu Leu Glu Thr
1               5                   10

<210> SEQ ID NO 50
<211> LENGTH: 14
<212> TYPE: PRT
<213> ORGANISM: Homo sapiens

<400> SEQUENCE: 50

Thr Glu Ala Asp Pro Glu Met Ile Lys Arg Ala Glu Asp Tyr
1               5                   10

<210> SEQ ID NO 51
<211> LENGTH: 15
<212> TYPE: PRT
<213> ORGANISM: Homo sapiens

<400> SEQUENCE: 51

Thr Glu Ala Asp Pro Glu Met Ile Lys Arg Ala Glu Asp Tyr Cys
1               5                   10                  15

<210> SEQ ID NO 52
<211> LENGTH: 13
<212> TYPE: PRT
<213> ORGANISM: Homo sapiens

<400> SEQUENCE: 52

Gly Asp Tyr Tyr Pro Ile Ile Tyr Phe Asn Asp Tyr Trp
1               5                   10

<210> SEQ ID NO 53
<211> LENGTH: 14
<212> TYPE: PRT
<213> ORGANISM: Homo sapiens

<400> SEQUENCE: 53

Cys Gly Asp Tyr Tyr Pro Ile Ile Tyr Phe Asn Asp Tyr Trp
1               5                   10

<210> SEQ ID NO 54
<211> LENGTH: 13
<212> TYPE: PRT
<213> ORGANISM: Homo sapiens

<400> SEQUENCE: 54

Arg Asn Leu Phe Pro Lys Asp Thr Leu Met Asn Leu His
1               5                   10

<210> SEQ ID NO 55
<211> LENGTH: 14
```

```
<212> TYPE: PRT
<213> ORGANISM: Homo sapiens

<400> SEQUENCE: 55

Cys Arg Asn Leu Phe Pro Lys Asp Thr Leu Met Asn Leu His
1               5                   10

<210> SEQ ID NO 56
<211> LENGTH: 27
<212> TYPE: PRT
<213> ORGANISM: Homo sapiens

<400> SEQUENCE: 56

Gly Gly Ala Pro Arg Val Ala Ser Arg Asn Leu Phe Pro Lys Asp Thr
1               5                   10                  15

Leu Met Asn Leu His Val Tyr Ile Ser Glu His
            20                  25

<210> SEQ ID NO 57
<211> LENGTH: 35
<212> TYPE: PRT
<213> ORGANISM: Homo sapiens

<400> SEQUENCE: 57

Leu Asp Gln Tyr Val Lys Phe Asp Ala Val Ser Gly Asp Tyr Tyr Pro
1               5                   10                  15

Ile Ile Tyr Phe Asn Asp Tyr Trp Asn Leu Gln Lys Asp Tyr Tyr Pro
            20                  25                  30

Ile Asn Glu
        35

<210> SEQ ID NO 58
<211> LENGTH: 15
<212> TYPE: PRT
<213> ORGANISM: Mus musculus

<400> SEQUENCE: 58

Pro Trp Asn Phe Leu Gly Asp Glu Leu Tyr Glu Gln Ser Asp Glu
1               5                   10                  15

<210> SEQ ID NO 59
<211> LENGTH: 112
<212> TYPE: PRT
<213> ORGANISM: Mus musculus

<400> SEQUENCE: 59

Glu Val Gln Leu Val Glu Ser Gly Gly Val Val Gln Pro Gly Arg
1               5                   10                  15

Ser Leu Arg Leu Ser Cys Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Ser Gly Ser Tyr Trp Gly Gln Gly Thr Leu Val Thr Val Ser Ser
            100                 105                 110
```

```
<210> SEQ ID NO 60
<211> LENGTH: 110
<212> TYPE: PRT
<213> ORGANISM: Mus musculus

<400> SEQUENCE: 60

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Lys Ser Ser
                85                  90                  95

Asn Thr Val Val Phe Gly Gly Gly Thr Lys Val Thr Val Leu
            100                 105                 110

<210> SEQ ID NO 61
<211> LENGTH: 43
<212> TYPE: PRT
<213> ORGANISM: Mus musculus

<400> SEQUENCE: 61

Leu Trp Arg Trp Gln Leu Tyr Ala Ala Gln Ser Thr Lys Ser Pro Trp
1               5                   10                  15

Asn Phe Leu Gly Asp Glu Leu Tyr Glu Gln Ser Asp Glu Gln Asp
            20                  25                  30

Ser Val Lys Val Ala Leu Leu Glu Thr Asn Pro
            35                  40

<210> SEQ ID NO 62
<211> LENGTH: 120
<212> TYPE: PRT
<213> ORGANISM: Mus musculus

<400> SEQUENCE: 62

Gln Val Gln Leu Gln Gln Ser Gly Thr Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Arg Tyr Asn Glu Lys Phe
    50                  55                  60

Lys Gly Lys Ala Thr Leu Thr Ala Asp Lys Ser Ser Thr Ala His
65                  70                  75                  80

Met Gln Leu Ser Ser Leu Thr Ser Asp Ser Ala Val Tyr Cys Ala
                85                  90                  95

Arg Trp Gly Gly Asn Tyr Ser Gly Tyr Ala Met Asp Tyr Trp Gly Gln
            100                 105                 110

Gly Thr Ser Val Thr Val Ser Ser
            115                 120
```

<210> SEQ ID NO 63
<211> LENGTH: 103
<212> TYPE: PRT
<213> ORGANISM: Mus musculus

<400> SEQUENCE: 63

Gln Ile Val Leu Thr Gln Ser Pro Val Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Ala Gly Thr Lys Leu
            100

<210> SEQ ID NO 64
<211> LENGTH: 363
<212> TYPE: DNA
<213> ORGANISM: Mus musculus

<400> SEQUENCE: 64
caggtccagc tgcagcagtc tggaactgaa ctggtgaggc ctgggacttc agtgaaggtg      60
tcctgcaagg cttctggata cgccttcact aattacttga tagagtgggt aaagcagagg     120
cctggacagg gccttgagtg gattggagtg attaatcctg aagtggtgg tactaggtac      180 aatgagaagt tcaagggcaa ggcaacactg actgcagaca atcctccac cactgcccac      240 atgcagctca gcagcctgac atctgatgac tctgcggtct atttctgtgc aagatggggg     300
ggaaactact ctggctatgc tatggactac tggggtcaag gaacctcagt caccgtctcc     360
tca                                                                   363

<210> SEQ ID NO 65
<211> LENGTH: 318
<212> TYPE: DNA
<213> ORGANISM: Mus musculus

<400> SEQUENCE: 65
caaattgttc tcacccagtc tccagtaatc atgtctgcat ctccagggga gaaggtcacc      60
ataacctgca gtgccagctc aagtgtaagt tacatgcact ggttccagca gaagccaggc     120
acttctccca aactctggat ttatagcaca tccaacctgg cttctggagt ccctgctcgc     180
ttcagtggca gtggatctgg gacctcttac tctctcacaa tcagccgaat ggaggctgaa     240
gatgctgcca cttattactg ccagcaaagg agtagttacc cacccacgtt cggtgctggg     300
accaagctgg agctgaaa                                                   318

<210> SEQ ID NO 66
<211> LENGTH: 10
<212> TYPE: PRT
<213> ORGANISM: Mus musculus

<400> SEQUENCE: 66

Ser Ala Ser Ser Ser Val Ser Tyr Met His

```
<210> SEQ ID NO 67
<211> LENGTH: 7
<212> TYPE: PRT
<213> ORGANISM: Mus musculus

<400> SEQUENCE: 67

Ser Thr Ser Asn Leu Ala Ser
1               5

<210> SEQ ID NO 68
<211> LENGTH: 9
<212> TYPE: PRT
<213> ORGANISM: Mus musculus

<400> SEQUENCE: 68

Gln Gln Arg Ser Ser Tyr Pro Pro Thr
1               5

<210> SEQ ID NO 69
<211> LENGTH: 5
<212> TYPE: PRT
<213> ORGANISM: Mus musculus

<400> SEQUENCE: 69

Asn Tyr Leu Ile Glu
1               5

<210> SEQ ID NO 70
<211> LENGTH: 16
<212> TYPE: PRT
<213> ORGANISM: Mus musculus

<400> SEQUENCE: 70

Val Ile Asn Pro Gly Ser Gly Gly Thr Arg Tyr Asn Glu Lys Phe Lys
1               5                   10                  15

<210> SEQ ID NO 71
<211> LENGTH: 11
<212> TYPE: PRT
<213> ORGANISM: Mus musculus

<400> SEQUENCE: 71

Ala Arg Trp Gly Gly Asn Tyr Ser Gly Tyr Ala
1               5                   10

<210> SEQ ID NO 72
<211> LENGTH: 14
<212> TYPE: PRT
<213> ORGANISM: Mus musculus

<400> SEQUENCE: 72

Thr Gly Thr Ser Ser Asp Val Gly Gly Tyr Asn Tyr Val Ser
1               5                   10

<210> SEQ ID NO 73
<211> LENGTH: 8
<212> TYPE: PRT
<213> ORGANISM: Mus musculus

<400> SEQUENCE: 73

Tyr Glu Val Thr Asn Arg Pro Ser
1               5
```

<210> SEQ ID NO 74
<211> LENGTH: 10
<212> TYPE: PRT
<213> ORGANISM: Mus musculus

<400> SEQUENCE: 74

Ser Ser Tyr Lys Ser Ser Asn Thr Val Val
1               5                   10

<210> SEQ ID NO 75
<211> LENGTH: 13
<212> TYPE: PRT
<213> ORGANISM: Mus musculus

<400> SEQUENCE: 75

Ala Ala Ser Gly Phe Thr Phe Ser Thr Tyr Ala Met His
1               5                   10

<210> SEQ ID NO 76
<211> LENGTH: 10
<212> TYPE: PRT
<213> ORGANISM: Mus musculus

<400> SEQUENCE: 76

Val Ile Ser Tyr Asp Gly Thr Asn Lys Tyr
1               5                   10

<210> SEQ ID NO 77
<211> LENGTH: 5
<212> TYPE: PRT
<213> ORGANISM: Mus musculus

<400> SEQUENCE: 77

Gly Ser Gly Ser Tyr
1               5

<210> SEQ ID NO 78
<211> LENGTH: 15
<212> TYPE: PRT
<213> ORGANISM: Homo sapiens

<400> SEQUENCE: 78

Gln Ala Gly Pro Gly Gly Ala Pro Arg Val Ala Ser Arg Asn Leu
1               5                   10                  15

<210> SEQ ID NO 79
<211> LENGTH: 15
<212> TYPE: PRT
<213> ORGANISM: Homo sapiens

<400> SEQUENCE: 79

Gly Gly Ala Pro Arg Val Ala Ser Arg Asn Leu Phe Pro Lys Asp
1               5                   10                  15

<210> SEQ ID NO 80
<211> LENGTH: 15
<212> TYPE: PRT
<213> ORGANISM: Homo sapiens

<400> SEQUENCE: 80

Arg Val Ala Ser Arg Asn Leu Phe Pro Lys Asp Thr Leu Met Asn
1               5                   10                  15

<210> SEQ ID NO 81
<211> LENGTH: 15
<212> TYPE: PRT
<213> ORGANISM: Homo sapiens

<400> SEQUENCE: 81

Arg Asn Leu Phe Pro Lys Asp Thr Leu Met Asn Leu His Val Tyr
1               5                   10                  15

<210> SEQ ID NO 82
<211> LENGTH: 15
<212> TYPE: PRT
<213> ORGANISM: Homo sapiens

<400> SEQUENCE: 82

Pro Lys Asp Thr Leu Met Asn Leu His Val Tyr Ile Ser Glu His
1               5                   10                  15

<210> SEQ ID NO 83
<211> LENGTH: 15
<212> TYPE: PRT
<213> ORGANISM: Homo sapiens

<400> SEQUENCE: 83

Leu Met Asn Leu His Val Tyr Ile Ser Glu His Glu His Phe Thr
1               5                   10                  15

<210> SEQ ID NO 84
<211> LENGTH: 15
<212> TYPE: PRT
<213> ORGANISM: Homo sapiens

<400> SEQUENCE: 84

His Val Tyr Ile Ser Glu His Glu His Phe Thr Asp Phe Asn Ala
1               5                   10                  15

<210> SEQ ID NO 85
<211> LENGTH: 15
<212> TYPE: PRT
<213> ORGANISM: Homo sapiens

<400> SEQUENCE: 85

Ser Glu His Glu His Phe Thr Asp Phe Asn Ala Thr Ser Ala Leu
1               5                   10                  15

<210> SEQ ID NO 86
<211> LENGTH: 15
<212> TYPE: PRT
<213> ORGANISM: Homo sapiens

<400> SEQUENCE: 86

Val Pro Pro Pro Leu Asp Gln Tyr Val Lys Phe Asp Ala Val Ser
1               5                   10                  15

<210> SEQ ID NO 87
<211> LENGTH: 15
<212> TYPE: PRT
<213> ORGANISM: Homo sapiens

<400> SEQUENCE: 87

Leu Asp Gln Tyr Val Lys Phe Asp Ala Val Ser Gly Asp Tyr Tyr
1               5                   10                  15

```
<210> SEQ ID NO 88
<211> LENGTH: 15
<212> TYPE: PRT
<213> ORGANISM: Homo sapiens

<400> SEQUENCE: 88

Val Lys Phe Asp Ala Val Ser Gly Asp Tyr Tyr Pro Ile Ile Tyr
1               5                   10                  15

<210> SEQ ID NO 89
<211> LENGTH: 15
<212> TYPE: PRT
<213> ORGANISM: Homo sapiens

<400> SEQUENCE: 89

Ala Val Ser Gly Asp Tyr Tyr Pro Ile Ile Tyr Phe Asn Asp Tyr
1               5                   10                  15

<210> SEQ ID NO 90
<211> LENGTH: 15
<212> TYPE: PRT
<213> ORGANISM: Homo sapiens

<400> SEQUENCE: 90

Asp Tyr Tyr Pro Ile Ile Tyr Phe Asn Asp Tyr Trp Asn Leu Gln
1               5                   10                  15

<210> SEQ ID NO 91
<211> LENGTH: 15
<212> TYPE: PRT
<213> ORGANISM: Homo sapiens

<400> SEQUENCE: 91

Ile Ile Tyr Phe Asn Asp Tyr Trp Asn Leu Gln Lys Asp Tyr Tyr
1               5                   10                  15

<210> SEQ ID NO 92
<211> LENGTH: 15
<212> TYPE: PRT
<213> ORGANISM: Homo sapiens

<400> SEQUENCE: 92

Asn Asp Tyr Trp Asn Leu Gln Lys Asp Tyr Tyr Pro Ile Asn Glu
1               5                   10                  15

<210> SEQ ID NO 93
<211> LENGTH: 15
<212> TYPE: PRT
<213> ORGANISM: Homo sapiens

<400> SEQUENCE: 93

Asn Leu Gln Lys Asp Tyr Tyr Pro Ile Asn Glu Ser Leu Ala Ser
1               5                   10                  15

<210> SEQ ID NO 94
<211> LENGTH: 6
<212> TYPE: DNA
<213> ORGANISM: Artificial Sequence
<220> FEATURE:
<223> OTHER INFORMATION: Expression vector 3' UTR

<400> SEQUENCE: 94 aataaa                                                                    6
```

THERAPEUTIC AGENTS TARGETING CLPTM1

The Sequence Listing submitted herewith, entitled "July-11-2019-Sequence-listing_ST25.txt", created Jun. 20, 2019 and having a size of 30,027 bytes, is incorporated herein by reference.

The present invention relates to immuno-oncology. More particularly, the present invention is directed to methods, therapeutic agents and compositions which target immune cells via the receptor CLPTM1 expressed on their cell surface, in order to modulate the immune system, especially in the treatment of cancer. Therapeutic agents capable of binding to CLPTM1 may be used according to various aspects of the present invention to eliminate cells expressing CLPTM1 at their surface, including immune cells, optionally in combination with other therapeutic agents, notably immune checkpoint inhibitors. The elimination of such cells is beneficial in the treatment of cancer. In other aspects of the invention, therapeutic agents capable of binding to CLPTM1 may be used to activate antigen-presenting cells, and thereby to activate an immune response, including particularly an immune response against cancer cells.

CLPTM1 is a transmembrane protein with a ~350 amino acid extracellular domain (the amino acid sequence of the ECD of human CLPTM1 is shown in SEQ ID NO: 2 and has 353 amino acids (representing amino acids 2-354 of SEQ ID NO: 1)). CLPTM1 has an unusual expression pattern and is expressed, for instance, in the cells of the immune system. Its physiological roles have not yet been fully elucidated but CLPTM1 has been identified to be genetically linked to cleft lip and palate (hence its name Cleft Lip and Palate Transmembrane protein 1). In the work leading to the present invention, we have discovered that CLPTM1 is expressed in various cells of the immune system, including Natural Killer cells (NK-cells), and antigen-presenting cells such as certain dendritic cells and macrophages, and also in various classes of lymphocytes, particularly various classes of T-lymphocytes; particular sub-sets of CD4+, CD8+ T-cells may express CLPTM1, as may particular subsets of CD3 CD45+ non-T-cells. In particular we have demonstrated cell surface expression.

We have previously identified that CLPTM1 is a receptor for Growth and Differentiation Factor 15 (GDF15) (also known as MIC-1). We have also identified that GDF15 is capable of binding to the pyroglutaminated RFamide Peptide Receptor (QRFPR). Binding agents for these receptors, specifically binding agents which inhibit the binding and/or effect of GDF15 at these receptors (i.e. antagonistic binding agents, or more particularly agents which are antagonistic with respect to the effect of GDF15 at the receptors) and polypeptides derived from these receptors and in their use in various therapies are the subject of commonly-owned patent application WO 2017/013188 (PCT/EP2016/067338), the disclosure of which is hereby incorporated by reference in its entirety.

GDF15 is a member of the TGF-β superfamily, but has a relatively low (24%) sequence homology with other members of the TGF-β superfamily. Elevated levels of GDF15 have been implicated in cancer, anorexia nervosa, osteoporosis, kidney disorders, pulmonary arterial hypertension, and cardiovascular disease, and also in cachexia and more generally in loss or suppression of appetite. GDF15 is a marker for mortality by any cause. The therapies proposed in WO 2017/013188 (PCT/EP2016/067338) are based on inhibiting the effect of GDF15, and thus for treating or preventing a condition associated with elevated or unwanted levels of GDF15, including the conditions listed above, and with respect to the receptor CLPTM1, particularly on reducing the immunosuppressive effects of GDF15, for example in the treatment of cancer.

It has previously been identified that certain proteins, which we have now identified to be ligands for CLPTM1, including GDF15 and TGFβ3, are expressed at high levels in certain cancers. GDF15, for example, is secreted in large amounts in late stage cancers, including prostate, breast and gastric cancers (Kim et al., 2008. Carcinogenesis 29, 704-712)), and colorectal cancers and glioblastomas (Albertoni et al., 2002. Oncogene 21, 4212-4219). Without wishing to be bound by theory, it is believed that expression of ligands for CLPTM1 in cancers can lead to a reduction in the local immune response generated by immune cells present in the tumour micro-environment, allowing evasion of the immune system by tumour cells. Elevated levels of ligands for CLPTM1 are therefore believed to have an immunosuppressive effect within the tumour micro-environment.

In cancer tissues, the tissue comprises not only tumour cells, but also infiltrating immune cells, including macrophages. Macrophages are derived from circulating monocytes, and when entering tissues become polarised into various macrophage types, including mainly the pro-inflammatory M1 cells, and anti-inflammatory M2 cells. The presence and amount of M2 macrophages in a tumour micro-environment are negative indicators of patient survival (Williams et al. 2016. Breast Cancer 2, 15025). A high density of M2-polarised tumour associated macrophages (TAM) in prostate cancer is statistically associated with a poor prognosis (Silvestri et al. 2016. Cancers 8, 64). Cancer cells often secrete factors that make macrophages adopt the anti-inflammatory M2 cell fate, including TGFβ and IL10. Current therapeutic strategies targeting M2 macrophages include attempting to convert M2 macrophages into M1 macrophages, and eliminating M2 macrophages from the tumour micro-environment.

In the work leading up to the present invention, it has been identified that CLPTM1 is selectively expressed on CD14+ macrophages (FIG. 1). CD14+ tumour-infiltrating leucocytes (TILs) having low levels of MHC2 (HLA-DR) on their surface are likely to be immunosuppressive as they lack the ability to present immunogenic peptides at their surface. CD14+ TILs derived from cancer patients have been found to have high levels of CLPTM1 at their surface (FIG. 2). CLPTM1 is also highly expressed on T-cells of TILs from cancer patients, on a population with low levels of TMEM173 (FIG. 3). This sub-population of T-cells is not highly active, as TMEM173 is required for the production of IFNγ and cytokines for T-cell activity. CLPTM1 is not significantly expressed on peripheral pro-inflammatory CD14+M1 macrophages or on dendritic cells derived from CD14+ PBMC in in vitro culture (FIG. 4). However, notably, we have identified that CLPTM1 is highly expressed on various antigen-presenting cells (APCs) found within the tumour microenvironment (TME), including dendritic cells (particularly plasmacytoid DCs (pDCs)), whereas CLPTM1 expression was not detectable on equivalent cells isolated from healthy spleen tissue (FIG. 8). We believe that the in vitro derived dendritic cells (DCs) of FIG. 4 are not truly representative of in vivo DCs, including those of the TME. Activation of APCs increases the ability of APCs to activate various cells of the immune system, including cytotoxic cells such as cytotoxic T-cells, typically through the secretion of pro-inflammatory cytokines. Activation of APCs within a tumour microenvironment is the mechanism underlying therapeutic cancer vaccines, and is believed to stimulate immunogenic cell death of cancer cells. However, the use of natural APCs such as a patient's own DCs has so far generated variable results. In order to overcome these disadvantages, artificial APCs have been suggested as a putative immunotherapy-based treatment for cancer (Loek et al. 2014. Trends in Biotechnology 32, 456-465).

Due to its high expression in immune cells, CLPTM1 presents an attractive candidate receptor for specifically targeting immune cells in order to modulate the activity of the immune system in a subject, particularly the immune system within a tumour microenvironment. Two separate and complementary mechanisms, which act to modulate the immune system in different ways, have been identified on the basis of the above observations. Due to its high expression in anti-inflammatory immune cells, and inactive T-cells, CLPTM1 presents an attractive candidate receptor for specifically targeting anti-inflammatory immune cells within a tumour micro-environment, to inhibit the growth and/or viability of such anti-inflammatory immune cells. As indicated above, the presence of anti-inflammatory immune cells may be beneficial to tumour growth as they may help cancer cells to evade the immune system. Anti-inflammatory immune cells thus represent a promising new target in cancer therapy. Furthermore, due to its expression on certain antigen-presenting cells within a tumour microenvironment, CLPTM1 represents an attractive candidate receptor for activating an anti-cancer immune response. We believe that tumour immunity benefits from the further activation of pDCs in the tumour micro-environment.

The present invention is therefore directed towards providing therapeutic agents which are capable of binding to CLPTM1 and which are able to harness mechanisms for modulating the immune system of a subject in order to treat cancer, including in one aspect by eliminating cells, and in another aspect by activating the immune system. Such agents can specifically recognise cells expressing CLPTM1 at their cell surface, and either target such cells for elimination, or allow cells expressing CLPTM1 to be specifically targeted with particular immunomodulatory therapeutic agents to modulate the activity of the immune system, specifically to activate the immune system.

The present invention particularly seeks to provide means to stimulate an immune response against cancer by a patient's own immune system by modulating the immune system within a tumour microenvironment. Specifically, this may be achieved by eliminating immunosuppressive CLPTM1-expressing immune cells in order to counter the anti-inflammatory effect that such cells have in a tumour micro-environment, and/or by stimulating antigen-presenting immune cells to activate cancer cell killing by the immune system. Without wishing to be bound by theory, it is believed that these effects can enhance the pro-inflammatory effects of other immune cells present within a tumour micro-environment (both by removing anti-inflammatory immune cells and by triggering pro-inflammatory immune cells to mount an immune response within a tumour), and can activate an immune response against a cancer. The effect of this is that a patient's own immune system can be harnessed to attack cancerous cells. Additionally, any cancer cells expressing CLPTM1 at their surface will be targeted by a patient's own immune system in a similar manner. Any cancer cells expressing CLPTM1 on their cell surface may also be targeted by a therapeutic agent as defined herein, to eliminate CLPTM1-expressing cancer cells.

Various strategies may be adopted to harness the targeting potential of CLPTM1-binding agents to the elimination of CLPTM1-expressing cells. These include notably the use of anti-CLPTM1 antibodies with immune effector activity, cytotoxic immune cells expressing chimeric antigen receptors (CARs) directed against CLPTM1, and antibody-based constructs such as conjugates of antibodies with drugs (e.g. toxins), or bi-specific T-cell engagers (BiTEs). BiTEs are single chain antibody constructs comprising minimal binding domains of antibodies for the T-cell receptor-associated molecule CD3 and for a target, cell-surface expressed, "cancer antigen" (here the CLPTM1 protein is targeted, rather than a cancer antigen as such). Concurrent engagement of the target cell antigen and CD3 leads to activation of cytotoxic T-cells, resulting in lysis, and hence elimination, of the target cells (see Stieglmaier et al., 2015, Expert Opinion on Biological Therapy, 15:8, 1093-1099 for a general discussion of BiTEs).

A number of such strategies, targeting various different cell surface expressed proteins, typically using antibodies, or antibody-based binding domains, have been proposed in the art, or have found clinical utility in the treatment of cancer. Principally, such known therapeutic agents target cell surface proteins whose expression levels are higher on cancer cells than normal healthy cells (i.e. "cancer antigens"). Such known immunotherapies include notably the use of a number of monoclonal antibodies such as Trastuzumab (Herceptin) targeting epidermal growth factor receptor 2 protein (HER2), Cetuximab (Erbitux) targeting epidermal growth factor receptor (EGFR), Bevacizumab (Avastin) targeting vascular endothelial growth factor-A (VEGF-A) and Rituximab targeting CD20, which is present on B-cells. Such antibodies exert their effects by various immune effector means, including notably antibody dependent cell-mediated cytotoxicity (ADCC) in which antibodies binding to target cells target the cells for elimination by cytotoxic immune cells, such as NK cells, macrophages, neutrophils and eosinophils; the Fc portions of the cell-bound antibodies on the target cells are bound by receptors on the cytotoxic immune cells, thereby triggering the cytotoxic response. Similar immune effector functions of the Fc portions of antibodies include ADCP (antibody dependent cell-mediated phagocytosis and CDC (complement dependent cytotoxicity).

Various antibody drug conjugates have also been used therapeutically to target cancer cells. For example, Kadcyla comprises the Herceptin antibody targeting Her2 (the receptor which is overexpressed in $Her^+$ breast cancer cells), conjugated to the tubulin inhibitor Mertansine (DM1). Brentuximab vedotin comprises a chimeric IgG1 antibody targeting CD30 conjugated monomethyl auristatin E, a drug that prevents cell division by disrupting microtubules, and is used in the treatment of Hodgkin lymphoma and anaplastic large cell lymphoma (ALCL). Gemtuzumab ozogamicin comprises an IgG4 anti-CD33 antibody conjugated to a cytotoxic calicheamicin derivative, and is used for the treatment of acute myeloid leukaemia (AML). Typically such antibody-toxin conjugates work by binding to target cells leading to internalisation and delivery of the toxin to the cell interior, where it exerts its effects.

Multiple other cell toxic conjugates are under development both clinically and pre-clinically using various different toxic agents, including radioisotopes and small molecule or other chemotherapeutic agents (see Diamantis et al. Antibody-drug conjugates—an emerging class of cancer treatment. British Journal of Cancer (2016) 114, 362-367). It will therefore be seen that a wide variety of receptors on a wide variety of different cells, and a number of different toxic agents have been utilised to specifically target and eliminate cells (e.g. cancer cells) expressing particular proteins at their cell surface.

Chimeric antibody receptors (CARs) represent yet another means for eliminating cells expressing a specific protein at their surface, and have also been used widely to target cancer cells. CARs are widely known in the art, and are fusion proteins comprising an antigen binding domain, typically but not always derived from an antibody, linked to the signalling domain of the TcR complex (or equivalent), and can be used to direct T cells or other immune effector cells against cancer cells expressing a specific ligand if a suitable antigen binding domain or antibody is selected. The use of CARs is therefore a well-known and practiced technology, and the use of immune cells expressing CARs represents an attractive and promising approach in various therapies, including cancer therapy.

Recently, microtubule inhibitors, such as DM1 and auristatin E, have been found to have an effect on immune cells found in a tumour microenvironment when administered in vivo, either in an isolated form (dolostatin) (Müller et al. Cancer Immunology Research 2, 741-755), or as an antibody drug conjugate in the form of Ado-trastuzumab emtansine (T-DM1) (Müller et al. Science Translational Medicine 7, 315ra188). It is believed that these effects are separate from the cytotoxic effect that these drugs have on cancer cells themselves. In particular, tubulin inhibitors have been found to activate dendritic cells when administered. Administration of such agents, which act to stimulate the immune system by activating dendritic cells, has been found to increase intratumoral effector T-cells, and reduce tumour size. However, these compounds have yet to be administered in a form which allows the direct and specific targeting of cells of the immune system, and instead the effects which have been observed arise from non-specific targeting of immune cells.

The present invention is thus based on principles and therapeutic strategies well known and established in the art, but adapts these approaches to target a previously unrecognised target protein, as a means of targeting unwanted or harmful cells in cancer therapy, most notably by modulating the immune system to achieve an anti-cancer immune response.

Unlike the majority of the immunotherapeutic agents known in the art, the therapeutic agents of the present invention are not primarily targeted towards binding (and thus eliminating) cancer cells per se, and instead are targeted primarily towards immune cells, including anti-inflammatory or immunosuppressive immune cells such as M2 macrophages, which can be found in a tumour micro-environment, and which can reduce or prevent the immune response mounted against cancer cells by a patient's own immune system, and antigen-presenting cells, particularly dendritic cells, the stimulation of which using particular agents has been found to activate an anti-cancer immune response. It is therefore in this way, rather than via direct targeting of tumour cells, that the present invention aims to provide therapies for cancer. However, as described further below, in certain or particular aspects, including for example in the treatment of certain cancer conditions or in certain combination therapies, the direct targeting of cancer cells is not excluded.

Accordingly, in a first aspect the present invention provides a therapeutic agent capable of binding to the receptor CLPTM1 at the surface of an immune cell and modulating its activity for use in modulating the activity of the immune system to treat cancer, wherein (i) the therapeutic agent is capable of inhibiting the growth and/or viability of an anti-inflammatory and/or immunosuppressive cell to relieve unwanted or deleterious immunosuppression by eliminating anti-inflammatory and/or immunosuppressive immune cells; and/or (ii) the therapeutic agent is capable of stimulating an antigen-presenting immune cell and acts to stimulate antigen-presenting immune cells to activate an anti-cancer immune response.

More particularly, in certain embodiments the therapeutic agent may comprise a binding agent capable of binding to CLPTM1 conjugated or otherwise linked to a moiety capable of modulating the activity of an immune cell, including by inhibiting, directly or indirectly, the growth and/or viability of a cell (notably a mammalian cell), or by stimulating an antigen-presenting immune cell to activate an anti-cancer immune response.

The moiety is particularly a separate moiety, that is, it is a moiety which is separate and distinct from the binding moiety. For example, the moiety may not be part of an antibody, and in particular embodiments it may not comprise a Fc portion of antibody, or any part thereof (more particularly, the moiety may not comprise a Fc portion, or part thereof, with immune effector function). As an example of a separate moiety the binding agent may be conjugated to a drug, e.g. a toxin. Such a separate moiety may be capable of directly inhibiting the growth and/or viability of a cell (e.g. it may be a toxin). An example of a separate moiety which is capable of indirectly modulating the activity of an immune cell (e.g. inhibiting the growth and/or viability of a cell) is a moiety which acts to recruit an immune cell or other immune response. A particular example of a separate moiety is an agent (or, alternatively expressed, a drug) capable of stimulating an immune effector cell, or in other words an immune-stimulating or immune-activating agent (or, alternatively expressed, an immune cell stimulator or immune cell activator).

In another example, the moiety may be an immune cell, notably an immune effector cell, e.g. a cytotoxic immune cell (in which case the binding agent may be "linked to" the "moiety" by being expressed on the surface of the immune cell). However, in other embodiments the therapeutic agent may comprise, or may be, a binding agent which is capable of inhibiting the growth and/or viability of a cell, e.g. which has immune effector function. For example the binding agent, e.g. an antibody, may comprise a Fc portion with immune effector function.

Accordingly, in particular embodiments the therapeutic agent may be:

(i) an antibody capable of binding to the receptor CLPTM1, wherein said antibody has immune effector activity, particularly antibody dependent cell-mediated cytotoxicity (ADCC), antibody dependent cell-mediated phagocytosis (ADCP) and/or complement dependent cytotoxicity (CDC);

(ii) a conjugate comprising a binding agent capable of binding to CLPTM1 conjugated to another (or second) agent, more particularly to an active agent (i.e. a functionally active or therapeutically active agent), for example a drug (e.g. a toxin such as a cytotoxic and/or cytostatic agent);

(iii) a bi-specific binding agent having a first binding domain capable of binding to CLPTM1 and a second binding domain capable of binding to a cytotoxic immune cell, particularly wherein the second binding domain is capable of binding to CD3; or (iv) a cytotoxic immune cell expressing a CAR capable of binding to CLPTM1, particularly wherein the cytotoxic immune cell is an NK cell or a T-cell.

Certain such therapeutic agents are novel products in their own right and hence in a further aspect the invention provides a therapeutic agent comprising a binding agent capable of binding to the receptor CLPTM1 expressed on the surface of a cell conjugated to a drug (e.g. a toxin such as a cytotoxic or cytostatic agent), wherein the binding agent is a CLPTM1 ligand or a fragment thereof, in particular wherein the binding agent is GDF15, TGFβ1, TGFβ2 or TFGβ3, or a fragment thereof.

In another aspect the invention provides a therapeutic agent being a bi-specific binding agent having a first binding domain capable of binding to CLPTM1 and a second binding domain capable of binding to a cytotoxic immune cell.

A still further aspect of the present invention provides a therapeutic agent being a cytotoxic immune cell which expresses on its cell surface a CAR capable of binding to CLPTM1.

Yet further aspects of the invention provide:

A pharmaceutical composition comprising a therapeutic agent of the invention as defined herein, in combination with one or more pharmaceutically acceptable carriers or excipients;

A therapeutic agent of the invention as defined herein for use in therapy;

Use of a therapeutic agent of the invention as defined herein in the manufacture of a medicament for use in modulating the activity of the immune system to treat cancer (notably by eliminating CLPTM1-expressing immune cells in the treatment of cancer, or by stimulating an antigen-presenting cell thereby to activate an immune response);

A method of treating cancer, said method comprising administering to a subject in need thereof a therapeutically effective amount of the therapeutic agent or the pharmaceutical composition of the invention as defined herein, wherein the therapeutic agent acts to modulate the activity of the immune system (notably by eliminating CLPTM1-expressing immune cells in the subject or by stimulating an antigen-presenting cell in the subject thereby to activate an anti-cancer immune response).

Further, it has been determined that cell surface-expressed CLPTM1 may be used as a biomarker for selecting, or identifying, subjects who may benefit from the therapies of the present invention.

Accordingly a yet still further aspect of the invention provides a method of identifying a cancer-suffering subject who may benefit from therapy with a therapeutic agent capable of binding to CLPTM1 at the surface of a cell and eliminating CLPTM1-expressing cells and/or activating a CLPTM1-expressing antigen-presenting cell, as defined herein, said method comprising detecting the presence of CLPTM1 expressed on the surface of a cell in a cell-containing sample from said subject. The cell may be an immune cell, or more particularly an anti-inflammatory or immunosuppressive immune cell, or an antigen-presenting cell.

Other aspects of the invention include a nucleic acid molecule encoding a CAR capable of binding to CLPTM1, and a vector comprising such a nucleic acid molecule.

In another aspect, the present invention provides a method of activating the immune system of a subject, said method comprising administering to said subject a conjugate comprising a binding agent capable of binding to CLPTM1 conjugated to an immune cell activating agent which is capable of stimulating an antigen-presenting immune cell, wherein said conjugate acts to stimulate antigen-presenting immune cells in the subject to activate an immune response.

In a yet further aspect, the present invention provides a product comprising:

(a) a therapeutic agent capable of binding to the receptor CLPTM1 at the surface of an immune cell and modulating its activity, wherein (i) the therapeutic agent is capable of inhibiting the growth and/or viability of an anti-inflammatory and/or immunosuppressive cell to relieve unwanted or deleterious immunosuppression by eliminating anti-inflammatory and/or immunosuppressive immune cells; and/or (ii) the therapeutic agent is capable of stimulating an antigen-presenting immune cell and acts to stimulate antigen-presenting immune cells to activate an anti-cancer immune response; and (b) an immune checkpoint inhibitor, as a combined preparation for separate, sequential or simultaneous use to modulate the activity of the immune system in the treatment of cancer.

In particular, the immune checkpoint inhibitor is an anti-PD1, an anti-PDL1, or an anti-CTLA-4 antibody.

Furthermore, present invention provides a method of modulating the activity of the immune system to treat cancer, said method comprising administering to a subject in need thereof a therapeutically effective amount of the therapeutic agent as defined above and an immune checkpoint inhibitor, preferably wherein the immune checkpoint inhibitor is an anti-PD1, an anti-PDL1, or an anti-CTLA-4 antibody.

More broadly, also disclosed, and provided according to the present invention, is a product (i.e. a combination therapy product, or a combined product) comprising:

(a) a therapeutic agent capable of binding to the receptor CLPTM1 at the surface of a cell and capable of (i) inhibiting the growth and/or viability of a cell, and/or (ii) stimulating an antigen-presenting immune cell; and (b) an immune checkpoint inhibitor, as a combined preparation for separate, sequential or simultaneous use in the treatment of cancer.

In a particular embodiment the immune checkpoint inhibitor is an anti-PD1, an anti-PDL1, or an anti-CTLA-4 antibody.

This aspect also provides a method of treating cancer comprising administering to a subject in need thereof a therapeutically effective amount of (a) a therapeutic agent capable of binding to the receptor CLPTM1 at the surface of a cell and capable of (i) inhibiting the growth and/or viability of a cell, and/or (ii) stimulating an antigen-presenting immune cell; and (b) an immune checkpoint inhibitor.

The therapeutic agent of part (a) of this aspect may be any therapeutic agent as defined and described herein, but in a particular embodiment it is a conjugate comprising a binding agent capable of binding to CLPTM1 conjugated to an active agent, e.g. drug, particularly an immune cell activator capable of stimulating an antigen-presenting cell, including any such agent defined herein, e.g. a tubulin inhibitor. In a preferred embodiment the therapeutic agent is a conjugate comprising a binding agent capable of binding to CLPTM1 conjugated to a tubulin inhibitor. In another embodiment the therapeutic agent is a conjugate comprising a binding agent capable of binding to CLPTM1 conjugated to a toxin.

In this aspect of the invention the therapeutic agent capable of binding to CLPTM1 may in part (i) inhibit the growth and/viability of any cell expressing CLPTM1, including a cancer cell, and/or an immune cell, e.g. an anti-inflammatory and/or immunosuppressive immune cell.

As reported in Example 14 below, we have further shown that a therapeutic agent as disclosed and defined herein may be particularly effective against metastasis of cancer and particularly against breast cancer metastases. We have also observed that metastases may in general have higher surface expression of CLPTM1 compared to primary tumours.

Accordingly another aspect disclosed, or provided, herein is a therapeutic agent capable of binding to the receptor CLPTM1 at the surface of a cell and (i) inhibiting the growth and/or viability of a cell and/or (ii) stimulating an antigen-presenting immune cell, for use in the treatment of metastasis from cancer, especially from breast cancer.

In particular, this may include metastases of breast cancer to the lung.

The therapeutic agent of the various aspects of the invention can bind specifically to a target cell (i.e. a cell expressing CLPTM1), and is capable, directly or indirectly, of modulating the activity of a target cell, including particularly an immune cell, thereby to modulate the activity of the immune system to treat cancer.

The therapeutic agent may be capable of inhibiting the growth and/or viability of a target cell, and particularly of an anti-inflammatory and/or immunosuppressive cell expressing CLPTM1, thereby causing a said target cell to be eliminated. Inhibiting the growth and/or viability of cells includes any activity or function which has a negative effect on survival or viability of cells, e.g. rendering a cell incapable of growth or replication. The therapeutic agent may thus be, or may comprise (e.g. be conjugated to), a cytotoxic and/or cytostatic agent. Thus, for example, a cytotoxic agent may cause the cell to be killed (e.g. to undergo apoptosis, or be phagocytosed, or otherwise disrupted or rendered non-viable). A cytostatic agent may lead to cell elimination by rendering the cell incapable of growth and/or replication. It will be noted that the term "eliminated" does not require that all target cells present in the subject are removed (e.g. killed) and includes a reduction in the number of such cells. In other words, the term does not require total or absolute elimination, and includes depletion of the cells. The term "eliminated" may accordingly be used interchangeably with the term "abrogated".

Target cells may be eliminated directly, for example where the therapeutic agent comprises a toxic component, or indirectly, for example by recruiting a component of the immune system that is capable of causing a target cell to be eliminated following binding of the agent to the target cell. The therapeutic agents of the present invention may therefore effect an immune response which leads to the death of a target cell. Such a response may comprise recruiting components (including humoral (e.g. antibodies and/or components of the complement pathway) and cellular components) of the immune system of a subject in order to effect cell death, or may comprise direct binding of a cytotoxic immune cell which expresses a receptor specific for the target cell and thus can specifically recognise a target cell, whereupon recognition of the target cell by a cytotoxic cell effects cell death. In certain preferred embodiments therefore the therapeutic agents of or for use according to the invention are (or comprise) cytotoxic agents. The term "cytotoxic" is used herein to mean that the agent can effect cell death in a cell to which it binds.

Additionally or alternatively, the therapeutic agent may be capable of stimulating an antigen-presenting immune cell, and act to stimulate antigen-presenting immune cells to activate an anti-cancer immune response. An antigen presenting cell (APC) may be any immune cell capable of presenting an antigen to other cells of the immune system, but typically may be a dendritic cell, or a macrophage or an antigen-presenting B cell. This includes, for example, activating antigen-presenting cells such as dendritic cells and promoting their maturation, and may include facilitating antigen uptake and migration of tumour-resident dendritic cells to tumour-draining lymph nodes, thereby potentiating a tumour-specific T-cell response. Activation of an anti-cancer immune response may therefore comprise an increase in tumour infiltrating lymphocytes present within a tumour, including CD4+Th1 and $T_{reg}$ cells, and CD8+ cytotoxic T-cells. Cytokines, such as IFNγ, which is secreted by cells of the immune system (including CD4+Th1 and CD8+ cytotoxic T cells) during an immune response may also be up-regulated, which in turn may induce further immune activation, including the maturation and proliferation of NK, NK, and B cells. Additionally, the phenotype of immune cells present within the tumour microenvironment may be shifted upon stimulation of the immune system as described herein. For example, the phenotype of immunosuppressive cells present within the tumour microenvironment, such as $T_{regs}$, Myeloid Derived Suppressor Cells (MDSC) or M2 macrophages may shift to a less immunosuppressive state. The anti-cancer immune response may therefore comprise the activation and proliferation of both myeloid and lymphoid cells of the immune system in various ways in order to achieve an anti-cancer immune response.

Accordingly, an anti-cancer immune response may be defined herein to be, or to include, killing of cancer cells, and/or rejection of a tumour, or any anti-cancer or anti-tumour effect mediated by the immune system. It may comprise, or involve, any, or all, of the full spectrum of anti-cancer (or anti-tumour) immunity, and may comprise activation of cytotoxic immune cells (e.g. cytotoxic T cells or NK cells), and/or regulatory immune cells, such as $T_{reg}$ or Th cells. The anti-cancer immune response may result in reduction of the size or extent of a cancer or tumour, the slowing or cessation of cancer cell or tumour growth, or the elimination of a cancer or tumour.

The term "target cell" refers to any cell which is to have its activity modulated (e.g. its growth and/or viability inhibited, or which is to be eliminated, or which is to be stimulated in order to stimulate an anti-cancer immune response) by any of the therapeutic agents according to the invention or disclosed herein. It may therefore be any CLPTM1-expressing cell, but in certain or particular aspects or embodiments it is an immune cell. In particular, this may be any CLPTM1-expressing cell (e.g. immune cell) present in or around a tumour (i.e. any cell or immune cell present in a tumour microenvironment) or a site of cancer in the body. This may include the circulation in the context of a haemopoietic cancer. As noted above, in various aspects the CLPTM1-expressing cell is an immune cell, however it may not be ruled out that a cancer cell (which term includes a tumour cell) expressing CLPTM1 at its surface may be targeted as a secondary effect by the therapeutic agents described herein. Furthermore, in certain other aspects disclosed herein the CLPTM1-expressing cell may be a cancer cell.

In certain embodiments the immune cell may be an immunosuppressive cell, or an anti-inflammatory cell of the immune system. Thus the cell may be a tumour-infiltrating immune cell, or tumour-infiltrating leucocyte (TIL). Such cells include macrophages in particular, notably M2 macrophages, but also include other cells, including T-cells, e.g. Treg cells. The therapeutic agents may accordingly be used according to the invention in therapies which eliminate anti-inflammatory immune cells which express CLPTM1, and in particular, such anti-inflammatory immune cells in a tumour micro-environment, in order to treat or prevent cancer. In particularly preferred embodiments, these agents may eliminate M2 macrophages and/or MDSCs in a tumour micro-environment.

Alternatively, the immune cell may be an antigen-presenting cell, such as a dendritic cell, particularly a plasmacytoid dendritic cell (pDC), or a macrophage. The therapeutic agents may accordingly be used according to the invention to stimulate such antigen-presenting immune cells, in order to treat or prevent cancer.

The term "treating" is used broadly herein to include any aspect of improving or ameliorating a condition or the clinical status of a subject suffering from or having the condition. Thus, a complete cure of the condition is not required and "treating" includes improving any aspect, parameter or symptom of a condition. In the context of cancer, treatment may include tumour regression, prevention or delay in progression, development or spread of the cancer, prolonged survival, improved quality of life, or any improvement in the clinical status of the subject, as well as remission of the cancer.

Similarly, the term "preventing" is used broadly herein to include any aspect of reducing or delaying a condition, or the onset or progression of a condition. Thus preventing does not require complete or absolute prevention of the development of a condition and may include delaying or slowing the progression or onset of any aspect, symptom or parameter of a condition. The severity of a symptom, parameter or aspect may be reduced and/or it may be delayed in developing. In the particular context of cancer, prevention may include reducing, delaying or preventing the spread, or development of the cancer, e.g. reduction or delay in metastasis.

As described above, in one embodiment the therapeutic agent may be an antibody which is capable of binding to the receptor CLPTM1 and which has immune effector function.

Antibodies having immune effector function, e.g. antibody-dependent cellular cytotoxicity (ADCC) and/or antibody dependent cell mediated phagocytosis (ADCP), or Complement Dependent Cytotoxicity can act in much the same way as any other antibody, i.e. by binding to a specific antigen on the surface of a cell they can prevent another entity from binding to or interacting with the target antigen, for example where the antigen is a receptor they can prevent a ligand or another molecule at the cell surface, e.g. another receptor, from interacting with the receptor. In this way, specific receptors on the surface of a cell (e.g. a cancer cell) can be blocked from binding to their ligands, or otherwise effecting their role or function.

However, such antibodies may also act by effecting an immune response against the cells to which they bind, e.g. by targeting the cells for elimination by cytotoxic immune cells such as NK cells, macrophages, neutrophils and eosiniphils. For example, CD16 receptors on NK cells are known to bind to the Fc portion of antibodies having Antibody Dependent Cell-mediated Cytotoxicity (ADCC) effector function, triggering degranulation and apoptosis. In this way, the antibodies of the present invention having immune effector function can act both to block binding of ligands for CLPTM1 mentioned above (GDF15, TGBβ1, TGFβ2 and TGFβ3) to the receptor, thereby blocking the immunosuppressive effects of the receptor, as well as targeting a cell (e.g. an immune cell such as an M2 macrophage) for elimination by cytotoxic lymphocytes of a subject's own immune system.

Not all antibodies have immune effector function and this depends on the nature of the Fc portion of the antibody. Antibodies which have an immune effector function comprise a sequence, or part, which is capable of inducing an immune response by a component of the immune system, e.g. a response by a subject's own immune cells. Put another way, antibodies which have an immune effector function comprise an immunogenic sequence, and thus be considered to be immunogenic. Antibodies which have an immune effector function therefore comprise a portion (or domain etc.) which can induce an immune response. In particular, the antibodies for use according to the present invention comprise an Fc portion which has immune effector function. Alternatively put, such antibodies may comprise an Fc portion which is immunogenic.

Immune effector functions induce a response by a subject's immune system against a specific target. The immune effector function of the antibodies of the present invention may induce an immune response in a number of different ways, depending on the nature of the antibody and its immune effector function. In other words, an antibody of the present invention may have one or more of several different immune effector functions, and different immune effector functions are known in the art. The term "immune effector function" (or "immune effector activity" which may be used interchangeably with said term) thus includes an effect in inducing any immune response which may act to eliminate a cell.

In particularly preferred embodiments of the present invention, the antibodies may induce antibody-dependent cellular cytotoxicity (ADCC) and/or antibody dependent cell mediated phagocytosis (ADCP). Examples of immunogenic Fc-tag sequences are known in the art (see e.g. Lazar et al. 2006. PNAS 103, 4005-4010); Shields et al. 2001. J. Biol. Chem. 276, 6591-6604; and Stewart et al. 2011. Protein Engineering, Design and Selection 24, 671-678). Such antibodies act to recruit cytotoxic cells of the immune system to attack a cell expressing CLPTM1 at its surface, e.g. NK-cells, macrophages, neutrophils and eosinophils. Numerous receptors which can target antibodies having effector function are known, and these are expressed on a variety different cytotoxic immune cells. For example, CD16 receptors on NK cells can recognise the Fc portion of antibodies bound to a target cell via the CLPTM1 receptor, and can exert its effect by triggering the target cell to degranulate and undergo apoptosis. Some immune cells trigger target cell death in an antibody dependent manner by releasing perforin and granzyme proteins causing cell lysis.

The antibodies of the present invention may additionally or alternatively effect an immune response by activating the complement system (in particular, the classical complement pathway), a component of the mammalian innate immune system. The effector function can therefore work through Complement Dependent Cytotoxicity in order to mediate an immune response against cells expressing CLPTM1. The C1 complex may be activated when an antibody is complexed with the CLPTM1 receptor, leading to the chain reaction and activation of the complement pathway. In this way, phagocytosis (by opsonising antigens), inflammation (by attracting macrophages and neutrophils) and membrane attack (by rupturing the membrane of a target cell) can lead to elimination of target cells.

The antibody according to this aspect of the present invention may be any antibody which has or comprises an immune effector function.

The term "antibody" is used broadly herein to include any type of antibody or antibody-based molecule. This includes not only native antibody molecules but any modified, synthetic or recombinant antibodies, as well as derivatives or fragments thereof. An antibody according to any aspect of the invention may thus be any molecule or entity or construct having antibody-based binding regions, that is a binding domain(s) which is/are derived from an antibody. Accordingly, an antibody according to any aspect of the present invention and disclosure may alternatively be defined as a binding molecule comprising an antigen-binding domain obtained or derived from an antibody. The antibody may be of, or may be derived from/based on an antibody of any convenient or desired species, class or sub-type. As noted above, the antibody may be natural, derivatised or synthetic. It may be monoclonal or polyclonal. Thus the antibody may bind to a single epitope or it may be a mixture of antibodies (or antibody molecules) binding to different epitopes.

Accordingly an antibody having immune effector function may be any type of antibody molecule, including an antibody fragment, which includes a portion having immune effector function. Various antibody-like molecules are known in the art (e.g. affibodies), and may be used in this aspect of the invention, provided they comprise a region or portion which provides immune effector function.

The portion of the antibody which provides immune effector function may be native to a particular antibody (i.e. the antibody may be an antibody isotype which naturally provides immune effector function), or the antibody may be modified to provide immune effector function, e.g. by substituting the Fc portion of an antibody with that of another antibody which provides immune effector function, or by providing an antibody as a fusion protein, e.g. to comprise one or more Fc sequences which provides immune effector function.

Preferably, the antibody is an IgG antibody having immune effector function. In humans, ADCC and ADCP are strongest in IgG1 antibodies and lowest in IgG4 antibodies, and the antibodies most widely-used in immunotherapy in humans are IgG1 and IgG3 antibodies. Thus, preferably the antibody may be an IgG1 or IgG3 antibody, preferably an IgG1 antibody. The antibodies may also be derived from any animal conventionally used (e.g. sheep, rabbits, goats or mice, or egg yolk), and may be monoclonal or polyclonal antibodies.

In a particular embodiment, the antibody may be a so-called "half molecule" antibody fragment, e.g. a molecule obtained by reductive cleavage of the disulphide binds connecting the respective heavy chains of an immunoglobulin dimer, or a molecule engineered (e.g. by site-directed mutagenesis) not to comprise the required cysteine residues to allow the formation of inter-chain disulphide binds (i.e. between the two halves of an immunoglobulin dimer). Thus, the antibody may be a monovalent antibody, e.g. comprising only a single light chain-heavy chain heterodimer, and thus only a single binding site for CLPTM1. In particular, it is believed that monovalent antibodies binding to CLPTM1-positive cells will not be internalised, or will be internalised to a lesser degree than may occur with a bivalent antibody, and hence they are preferred, according to this aspect of the invention, as an antibody with immune effector function.

An antibody may be a single chain antibody. A single chain antibody may be defined as a genetically engineered molecule containing the variable region of the light chain, the variable region of the heavy chain, linked by a suitable polypeptide linker as a fused single chain molecule. A single chain antibody may be provided with immune effector function by including a domain, or region, in the fused molecule which has immune effector activity. For example, a single chain antibody comprising variable region domains (e.g. a scFv) may be fused to a Fc portion or domain with immune effector activity.

A chimeric antibody may be prepared by combining the variable domain of an anti-CLPTM1 antibody of one species with the constant regions of an antibody derived from a different species. Such techniques may be used e.g. to humanise antibodies for therapeutic use.

Preferably the antibody will be a humanised or chimeric antibody, i.e. an antibody which has been modified or created to comprise a binding domain (e.g. a complementarity determining region (CDR)) which recognises a human CLPTM1 and a fixed (e.g. Fc) domain that has been modified to increase their similarity to antibody variants produced naturally in humans. In a particular aspect, a humanised or chimeric monoclonal antibody may be the IgG1 or IgG3 subtype. Modifications of this type are desirable to provide antibodies which have the greatest immune effector function.

In another preferred embodiment the antibody may be a human antibody. Human antibodies may be prepared using transgenic mice or other transgenic animals which may have been modified to express human immunoglobulin genes. They may also be obtained from phage display or indeed they may be isolated from human subjects, namely a human subject in whom the anti-receptor antibodies natively exist or are present (i.e. without the need to immunise the subject for antibody production), for example a human auto-immune subject.

The antibodies may be modified or engineered in order to further increase the strength of their immune effector function. For example, it is known that glycoengineered therapeutic antibodies lacking a core fucose from the Fc N-glycans exhibit ADCC at lower concentrations with much higher efficacy compared to fucosylated counterparts (Natsume et al. 2006. J Biochem 140, 359-368), and can evade the inhibitory effect of serum IgG. Compared to fucosylated IgGs, non-fucosylated forms exhibit dramatically enhanced ADCC due to the enhancement of FcγRIIIa binding capacity (Shields et al. 2002. J Biol Chem 277, 26733-40) without any detectable change in CDC or antigen binding capability. Antibodies with reduced fucosylation, or which are non-fucosylated therefore represent a particularly attractive therapeutic agent for ADCC. An afucosylated antibody may be prepared a number of means as described in Yamane-Ohnuki and Satoh 2009. mAbs 1, 230-236, which is herein incorporated by reference in its entirety. Thus, in a preferred embodiment of this aspect of the present invention, the antibodies may be afucosylated or have reduced fucosylation, compared to a fucosylated antibody.

Alternatively, the antibodies may be modified in other ways to increase their immune effector function. For example amino acid changes in the Fc region may enhance effector functions such as S239D/1332E versions of Fc regions (Lazar et al PNAS 2006 vol 103 no 11 4005-4010).

In another aspect, the present invention uses or provides a therapeutic agent which is, or which comprises, a binding agent capable of binding to the receptor CLPTM1 expressed on the surface of a cell conjugated to an active agent e.g. a drug, such as a toxin.

Example 3 and FIG. 6 show the effectiveness of targeting cells expressing CLPTM1 using such a binding agent conjugated to a cytotoxic drug, and demonstrate that such a binding agent is highly effective at eliminating cells expressing CLPTM1. Examples 7 and 6 and FIGS. 10 and 9 show that an immune activator conjugated to a CLPTM1 binding agent (in this case an antibody) is capable of stimulating antigen-presenting immune cells isolated from a tumour microenvironment, and demonstrate that such activation may be effective at reducing the size of a tumour. Example 8 and FIG. 11 also show that this arises as a result of activation of an anti-cancer immune response.

In addition to antibodies as discussed above (which includes antibodies which may or may not have immune effector function), any binding agents which are capable of binding to CLPTM1 may be used according to this aspect of the invention. Thus, any binding agent which is capable of specifically binding to CLPTM1, including its native ligands or portions or parts thereof, may be conjugated to an active agent (such as a drug, e.g. a toxin such as a cytotoxic and/or cytostatic drug, or an immune cell activator, in order to provide a therapeutic agent according to this aspect of the invention, which may be used to modulate the activity of a cell (e.g. an immune cell) expressing CLPTM1 at its cell surface.

A binding agent of this aspect of the invention may thus be any binding partner for CLPTM1, and thus includes any agent, e.g. any compound, molecule or entity having the ability to bind to CLPTM1. In particular the binding agent may bind specifically to CLPTM1 (or more particularly, the extracellular domain thereof).

Binding agents according to this aspect of the present invention may thus be selected from proteins or polypeptides such as antibodies (which as noted above includes fragments or derivatives of antibodies or any molecule comprising an antibody-derived binding domain), a combinatorially derived polypeptide from phage display or ribosome display or any other peptide display system, GDF15, TGFβ1, TGFβ2, TGFβ3 or fragments thereof (e.g. polypeptides comprising all or a portion of GDF15, TGFβ1, TGFβ2 or TGFβ3), or a nucleic acid molecule, such as an aptamer, or combinations thereof, capable of binding to CLPTM1.

In a preferred embodiment of the invention, the binding agent is a protein, preferably an antibody molecule, as defined and described above.

An antibody according to this aspect of the present invention includes: (a) any of the various classes or subclasses of immunoglobulin e.g. IgG, IgA, IgM, IgD or IgE derived from any animal e.g. any of the animals conventionally used e.g. sheep, rabbits, goats, or mice or egg yolk;
(b) monoclonal or polyclonal antibodies;
(c) intact antibodies or fragments of antibodies, monoclonal or polyclonal, the fragments being those which contain the binding region of the antibody e.g. fragments devoid of the Fc portion (e.g. Fab, Fab', F(ab')2, Fv), the so called "half molecule" fragments obtained by reductive cleavage of the disulphide bonds connecting the heavy chain components in the intact antibody. Fv may be defined as a fragment containing the variable region of the light chain and the variable region of the heavy chain expressed as two chains;
(d) antibodies produced or modified by recombinant DNA or other synthetic techniques, including monoclonal antibodies, fragments of antibodies, humanised antibodies, chimeric antibodies, or synthetically made or altered antibody-like structures.

Thus the antibody may be a functional derivative or "equivalent" of a native antibody e.g. single chain antibody.

Methods of making such antibody fragments and synthetic and derivatised antibodies are well known in the art. Also included are antibody fragments containing the complementarity-determining regions (CDRs) or hypervariable regions of the antibodies. These may be defined as the region comprising the amino acid sequences on the light and heavy chains of an antibody which form the three dimensional loop structure that contributes to the formation of the antigen binding site. CDRs may be used to generate CDR-grafted antibodies. As used herein "CDR grafted" defines an antibody having an amino acid sequence in which at least parts of one or more sequences in the light and/or variable domains have been replaced by analogous parts of CDR sequences from an antibody having a different binding specificity for a given antigen. One of skill in the art can readily produce such CDR grafted antibodies using methods well known in the art.

The antibody may be a chimeric antibody as described above, including particularly a humanised antibody.

Monoclonal antibodies and their fragments and derivatives are preferred antibodies according to the present invention.

In another preferred embodiment the antibody of this aspect of the invention may be a human antibody, as discussed above.

Antibodies binding to CLPTM1 have been reported and are commercially available (see for example in the Examples below). One such example is the anti-CLPTM1 antibody bs-8018R available from Bioss Antibodies (USA). Another example is the rabbit monoclonal antibody EPR8800 available under the name RabMab® from Abcam, Cambridge, UK. Furthermore, antibodies to the receptors may readily be prepared using known and routine techniques. Anti-CLTPM1 antibodies have been prepared in the course of work leading to the present invention and are used in the Examples below. These include the antibodies identified by the designations 7G12 and 59D04 used herein. These antibodies are defined with reference to their CDR and heavy and light chain sequences below. Methods for determining the binding site of an antibody in its antigen (the moiety to which it binds) are also routine and so it is readily possible to determine the epitope, or antibody binding site in CLPTM1.

Conjugation of a drug to a binding agent allows the drug to be targeted to specific cells within a patient (i.e. cells expressing a specific receptor—in the case of the present invention; CLPTM1), thereby allowing a far lower overall dose of a drug (e.g. a toxin) to be administered to a patient than conventional therapy would otherwise allow. It is evident that the effect of this will be to reduce the likelihood and severity of side-effects arising from a particular course of therapy, whilst also allowing specific populations of cells to be targeted.

Binding agents may be conjugated to drugs directly (including by means of a linker as discussed elsewhere) alternatively binding agent drug conjugates may be provided in which the binding agent and the drug are themselves conjugated to a separate molecule or moiety. Examples of the latter may include antibody nanoparticle conjugates, in which both the drug and the antibody are conjugated to the same nanoparticle. Alternatively expressed, the CLPTM1 binding agent may be conjugated to a nanoparticle or other carrier comprising or containing the drug. Advantageously, such a nanoparticle may allow the targeted delivery of a greater number of drug molecules to a cell expressing CLPTM1 at its cell-surface than a drug molecule directly conjugated to a binding agent.

Advantageously, the binding agent-drug conjugates are actively taken up into a target cell upon binding of the agent to CLPTM1, e.g. into vesicles or endosomes. CLPTM1 is known to be in a state of dynamic flux at the cell membrane, and thus binding moieties capable of binding to CLPTM1 may be taken up by endocytosis by a target cell.

We have observed that certain binding agents (e.g. antibodies) binding to CLPTM1 at the surface of a cell may be internalised, and we believe that at least in some cases this may be due to their bivalent nature. Hence, according to one aspect of the invention, in one embodiment the binding agent (e.g. antibody) is bivalent (i.e. it may be a bivalent antibody).

In another embodiment the therapeutic agent (e.g. a binding agent-drug conjugate) is capable of being internalised by the CLPTM1-expressing cell.

We have also observed that the extent to which binding agents (in this particular example, antibodies) binding to CLPTM1 at the surface of a cell are internalised may vary (see FIG. 14). This may affect the extent to which a drug conjugated to a binding agent is actually taken up into a target cell. Without wishing to be bound by theory, it is believe this variation may be at least in part down to variations in the affinity of binding agents for the CLPTM1 receptor. Thus, in preferred embodiments, the therapeutic agent of any aspect of the invention, or in one particular aspect or embodiment the binding agent drug conjugate, binds to the extracellular domain of CLPTM1 with a high affinity, i.e. the binding agent may be a high affinity binding agent for CLPTM1.

The affinity of a binding agent for CLPTM1 may be determined qualitatively. This may be done, for example, by measuring the uptake of a binding agent conjugated to a fluorescent moiety, and determining the mean fluorescence intensity of said cell, e.g. by flow cytometry. An example of such an assay is described in Example 13 and shown in FIG. 15. FIG. 15 demonstrates that the 59D04 antibody (either as an IgG1 or IgG2a isotype) is efficiently taken up by human CD14+ cells, whereas a negative control IgG1 antibody, and the "Santa Cruz" (Santa Cruz G7) anti-CLPTM1 antibodies are not. As described in greater detail below, the 59D04 antibody has been found to have higher affinity for CLPTM1 than the "Santa Cruz" antibody. Thus, in certain embodiments a high affinity binding agent may have a higher binding affinity for CLPTM1 than the Santa Cruz G7 anti-CLPTM1 antibody, or may have a binding affinity which is the same as or higher than the 59D04, or the Abcam or the 7G12 antibodies disclosed herein.

Alternatively, the binding affinity may be measured in a more quantitative manner, and this may be performed in any of a variety of different ways, including by various biophysical means such as Surface Plasmon Resonance (SPR) or Isothermal Titration calorimetry (ITC), or by spectroscopic means such as NMR shift-mapping in order to calculate a $K_D$ value for a binding agent.

Alternatively, a dilution series of the binding agent may be prepared and binding of the binding agent to CLPTM1 may be measured for the each concentration of the binding agent, thereby to determine the concentration at which 50% of the maximal binding is achieved, i.e. measure an $EC_{50}$ value for a binding agent. Binding in such an assay may be measured in a variety of convenient, ways, including by ELISA, e.g. by immobilising CLPTM1 on the surface of wells of a multi-well plate and measuring the extent of binding of the binding agent at each different concentration, or by flow cytometry, by measuring the extent of binding of the binding agent to cells expressing CLPTM1. In each case, binding of the binding agent to CLPTM1 may be measured directly, e.g. using a binding agent that has been labelled with a detection label, or indirectly, e.g. using a secondary detection reagent, e.g. a secondary antibody, which carries such a label (the literal meaning of the term "secondary" antibody in this context refers to embodiments of the invention in which the detection agent is an antibody, but it should be understood that an equivalent detection assay may be performed for other binding agents using an antibody which carries a detection label, and thus that this term should not be considered to be limiting on the nature of the binding agent).

Accordingly, the binding agents which are to be used according to this aspect of the present invention (e.g. which may be termed "high affinity") may preferably have an $EC_{50}$ value of 1 µg/ml or less when determined by measuring binding to membrane-permeabilised O-876 cells expressing native CLPTM1 by flow cytometry. More particularly, however, the $EC_{50}$ value when measured in this way is 0.9, 0.8, 0.7, 0.6, 0.5, 0.4, 0.3, 0.2 or 0.1 µg/ml or less. In representative particular embodiments, the $EC_{50}$ value when measured in this way is 0.5 or 0.1 µg/ml or less.

In experiments described in the Examples below, antibody 7G12 was found to demonstrate greater than 50% maximal binding at 1 µg/ml. The $EC_{50}$ value is accordingly lower than 1 µg/ml. Thus, the threshold for affinity of the binding agent according to the invention may be set at less than 1 µg/ml.

Alternatively, the affinity of the binding agent may be defined on the basis that the binding agent demonstrates greater than 50% maximal binding at 1 µg/ml or less when determined by measuring binding of the binding agent to membrane-permeabilised 0-876 cells expressing native CLPTM1 by flow cytometry. In other words the affinity may be defined as a value at which the binding agent shows greater than 50% of the maximal binding in the flow cytometry assay defined above. In particular embodiments, the affinity value when measured and defined in this way is 0.9, 0.8, 0.7, 0.6, 0.5, 0.4, 0.3, 0.2 or 0.1 µg/ml or less (i.e. the binding agent demonstrates greater than 50% maximal binding at 0.9, 0.8, 0.7, 0.6, 0.5, 0.4, 0.3, 0.2 or 0.1 µg/ml or less when measured in the flow cytometry assay defined above). In representative embodiments, the affinity value when measured in this way is 0.5 or 0.1 µg/ml or less.

The component conjugated to the binding agent according to this aspect of the present invention may be any component capable of modulating the activity of a cell, including an immune cell, i.e. any active agent or drug. In particular, it may be a drug or active agent capable of inhibiting the growth and/or viability of a cell, or of stimulating an antigen presenting cell. In certain embodiments, said component (i.e. the active agent or drug) may be a radioisotope, a toxin or a small molecule compound.

The immunomodulatory effect that a given drug has on a cell (e.g. an immune cell) expressing CLPTM1 may vary depending on the drug and on the identity of the cell (e.g. immune cell). Thus, a drug which is toxic (e.g. cytotoxic and/or cytostatic) to a first type of immune cell, and thus which acts to inhibit the growth and/or viability of said cell, may act as an immune activator when contacted with a second type of immune cell. Furthermore, and as described above, a drug may act to shift the phenotype of an immunosuppressive and/or anti-inflammatory immune cell, thereby to activate an anti-cancer immune response.

In one embodiment the drug may be immune cell activator. Exemplary immune cell activators include Toll-like Receptor (TLR) agonists (e.g. the TLR7 agonist UC-1V150, which has been used in therapy coupled to Rituximab anti-CD20 antibody (Gadd A J et al Bioconjug Chem. 2015 Aug. 19; 26(8):1743-52 and WO 2013166110). Alternative TLR agonists are in therapeutic development, and the drug may thus be, for example, a TLR3 agonist (Hiltonol (poly-ICLC), Ampligen), a TLR4 agonist (MPLA (Monophosphoryl Lipid A), G100 (Immune Design)) TLR5 (Entolimod), a TLR7 agonist, (TMX-101, Aldara, AZD8848 (also known as DSP-3025), GSK2245035 (Biggadike et al, J. Med. Chem. 2016, 59, 1711-1726), RG7795 (previously ANA-773), PF-4878691, GS9620 (also known as IMDZQ)) TLR7/8 (3M-052 (also known as MEDI-9197), R848 (Resquimod)), a TLR8 agonist (VTX-2337 (Motolimod)), a TLR9 agonist, (10181SS, MGN1703 (Lefitolimod, also known as dSLIM-30L1, Schimdt et al Allergy 2006: 61: 56-63), PF-3512676 (CpG 7909), SD-101, IMO-2125, CMP-001), ora TLR2/4 agonist, (BCG), Wu, T. Y.-H. (2016), Immunology, 148: 315-325. Alternatively, the drug may be a STING agonist (Hanson et al. J Clin Invest. 2015; 125(6):2532-2546. Wilson et al Nanomedicine. 2017 Nov. 7; 14(2):237-246. STING agonists are in therapeutic development and show promise as immune activators for cancer treatment. Examples of STING agonists are (2'2'cGAMP, 3'3'-cGAMP, 2'3'cGAMP, or various synthetic analogues of these such as ADU-S100 (MIW-815), or DMXAA (Vadimezan)).

Of particular interest is Hiltonol (poly-ICLC), as a TLR3 agonist which activates translocation of CLPTM1 to the cell surface and induces type I interferon responses such as IFNb effective in activating an anti-tumour immune response. Poly-ICLC (Polyinosinic-polycytidylic acid-polylysine-carboxymethylcellulose, PUBCHEM CID:121596028) is a plasma stabilized version of poly-IC, a dsRNA molecule.

DNA binding agents have also been found to have immune stimulating properties and may also be used as an immune activating drug component of a conjugate, for example a pyrrolobenzodiazepine dimer (PBD), As discussed above, compounds which act to inhibit microtubule formation have been identified as being capable of stimulating antigen-presenting cells, particularly within a tumour microenvironment. In one embodiment therefore, the drug may be an antimicrotubule agent (also known as a microtubule inhibitor or tubulin inhibitor). This class of drugs typically includes maytansinoids such as mertansine (DM1) or emtansine, as well as auristatin or auristatin derivatives, including derivatives of auristatin E, such as esters formed between auristatin E and a keto acid, or monomethyl auristatin E (MMAE), and these may be provided in a cytotoxic drug conjugate according to this aspect of the present invention. Other examples of anti-tubulin agents include taxanes (e.g. paclitaxel and docataxel) and taxane analogues (e.g. epothilone A and B), vinca alkaloids (e.g. vincristine, vinblastine, vindesine and vinorelbine), baccatine derivatives, nocodazole, colchicine and colcimid, estramustine, cryptophysins, cematodin, combretastatins, discodermolide and eleutherobin.

In one embodiment, the drug may be toxic to a cell. A drug which is toxic to an immune cell, in particular an anti-inflammatory and/or immunosuppressive cell, may result in its elimination. Similarly a drug which is toxic (or also toxic) to a cancer cell, may result in its elimination. Thus, the component (drug) which is conjugated to the binding agent may be any toxic component, that is any component which is toxic to a cell, and which may result in its elimination. A wide range of toxins are known in the art and the toxin may be any element, radioactive isotope (radioisotope), small molecule, or biological molecule or pharmaceutical compound that is toxic (e.g. cytotoxic and/or cytostatic) to a mammalian cell, particularly to a mammalian cell which expresses CLPTM1 at its cell surface (e.g. a cell of the immune system such as an M2 macrophage).

Thus, according to one particular embodiment, the drug may be a radioisotope used in radiotherapy to treat cancer. Typical examples of radioisotopes which may be used for this purpose therefore include iodine-131, lutetium-177 and yttrium-90, strontium-89 and samarium-135.

Antimicrotubule agents (as described above as immune cell activators) may be toxic to certain mammalian cells (including cancer cells) and hence these may also be used toxic components of conjugates.

Further exemplary small molecules which may be conjugated to a binding agent according to this aspect of the invention include α-amanitin, SN38, pyrrolobenzodiazepines, Calicheamicin, DM4, Duocarmycin, doxorubicin and methotrexate. Indeed, any chemotherapeutic agent used or proposed to treat cancer (i.e. any chemotherapy drug) may be used, as may another toxic agent known or proposed for any medical use (e.g. to kill or ablate any other cells). A wide range of such agents are known and described in the literature. The drug (e.g. toxin) may be conjugated to the binding agent directly, or alternatively may be conjugated to the binding agent by an intermediate molecule, i.e. a linker. Preferably, the linker is highly stable prior to administration and in the circulatory system of a patient in order to minimise the extent to which the cytotoxic payload of the therapeutic conjugate can circulate freely in a subject, and to ensure that a higher dose of the drug is administered directly to the target cells of interest.

Linkers may be cleavable, and preferably are cleavable following uptake by a target cell. Examples of cleavable linkers include disulphide bonds, hydrazones and peptides. Alternatively, linkers may be non-cleavable, and may, for example, comprise a thioester linkage.

Methods for coupling or conjugating a drug/active agent to a binding agent such as an antibody are well known in the art. These may include for example coupling the drug via a thiol group present in or introduced into the drug by SMCC linkers reactive to lysines present in the antibody (or other protein-based binding agent). Alternatively, the coupling may be via maleimide groups introduced into the drug, coupled to disulphide groups in the antibody (binding agent). Such disulphides may be generated in the antibody (binding agent) by slight reduction.

Cells expressing CLPTM1 at their surface may alternatively be eliminated using a cytotoxic immune cell comprising a Chimeric Antigen Receptor (CAR) capable of binding to CLPTM1.

Thus, according to another aspect the present invention therefore also provides a nucleic acid molecule encoding a chimeric antigen receptor (CAR) directed against CLPTM1, wherein said CAR when expressed on the surface of an immune effector cell is capable of binding to CLPTM1 expressed on a target cell surface.

The CAR may thus comprise a binding domain which is capable of binding specifically to CLPTM1. In particular the CAR may contain an antigen binding domain capable of binding specifically to CLPTM1, although it is not essential that the binding domain of the CAR is derived from an antibody, and binding domains from other sources may be used. In a particular embodiment the CAR comprises an antigen binding domain comprising a $V_L$ sequence and a $V_H$ sequence from an antibody specific for CLPTM1.

A vector comprising such a nucleic acid molecule, as well as a cytotoxic immune cell comprising said vector and expressing a CAR directed against CLPTM1 thus represent yet further aspects of the present invention.

Another aspect of the invention provides an immune effector cell comprising a nucleic acid molecule or vector of the invention as defined herein. The immune effector cells of the invention may find particular utility in therapy.

Also provided is a method of generating a CLPTM1-specific immune effector cell, said method comprising introducing a nucleic acid molecule or vector of the invention as defined herein into an immune effector cell.

CARs are engineered receptors which comprise a binding domain capable of binding to a target entity (e.g. a target molecule or epitope), typically an antigen recognition domain (e.g. from an antibody), fused to components of the native T-cell receptor (TCR), and are used to engineer cytotoxic immune cells (e.g. T-cells or NK cells) to have the specificity of a monoclonal antibody. Cytotoxic immune cells expressing a CAR therefore express receptors specific to a particular target entity (e.g. antigen), and thereby can be used to eliminate specific cells which express that entity (e.g. antigen) at their cell surface (including anti-inflammatory immune cells such as M2 macrophages as described above).

In a typical CAR, the variable portions of the immunoglobulin heavy and light chains are fused by a flexible linker to form an scFv (i.e. to allow the different domains of the scFv to orient in different directions, so that the structure of the antigen binding site of the native antibody on which the CAR is based may form. Thus, a CAR based on a known anti-CLPTM1 antibody (i.e. comprising the variable regions of an anti-CPLTM1 antibody as a scFv) will have the antigen binding site of that antibody, and thus will be specific for CLPTM1.

The binding domain of the CAR is extracellular (i.e. when the CAR is expressed on an immune effector cell). The CAR may thus comprise, in one embodiment, an extracellular domain comprising an antigen binding domain comprising $V_L$ and $V_H$ sequences of an anti-CLPTM1 antibody.

The nucleic acid molecule of the invention may be used to prepare immune effector cells (more particularly modified immune effector cells) directed against cells expressing CLPTM1. Such (modified) immune effector cells express the CAR on their cell surface and are capable of recognising, or binding to, a target cell expressing CLPTM1, e.g. an M2 macrophage. Accordingly, the nucleic acid molecule is such that an immune effector cell expressing said CAR (i.e. the CAR encoded by the nucleic acid molecule) is capable of effector activity (e.g. cytotoxic activity) against (e.g. killing) a target cell expressing CLPTM1. A modified immune effector cell is accordingly a genetically modified or engineered immune effector cell, or alternatively expressed an immune effector cell which has been transduced with a nucleic acid molecule of the invention.

The nucleic acid molecule may be introduced into an immune effector cell as mRNA or as DNA for expression in the cell. Vectors may be used to transfer the nucleic acid molecule into the cell or to produce the nucleic acid for transfer (e.g. to produce mRNA for transfer, or to produce a nucleic acid molecule for preparation of an expression vector for transfer into a cell).

The vector may for example be an mRNA expression vector, a cloning vector or an expression vector for transfer into an immune cell e.g. a viral vector.

An immune effector cell may be any immune cell capable of an immune response against a target cell expressing CLPTM1. More particularly, the immune effector cell is capable of abrogating, damaging or deleting a target cell, i.e. of reducing, or inhibiting, the viability of a target cell, preferably killing a target cell (in other words rendering a target cell less or non-viable). The immune effector cell is thus preferably a cytotoxic immune effector cell.

The term "cytotoxic" as used in the context of an immune effector cell is synonymous with "cytolytic" and is used herein to refer to a cell capable of inducing cell death by lysis or apoptosis in a target cell.

The term "immune effector cell" as used herein includes not only mature or fully differentiated immune effector cells but also precursor (or progenitor) cells therefor, including stem cells (more particularly haemopoietic stem cells, HSC), or cells derived from HSC. An immune effector cell may accordingly be a T-cell, NK cell, NKT cell, neutrophil, macrophage, or a cell derived from HSCs contained within the CD34+ population of cells derived from a haemopoietic tissue, e.g. from bone marrow, cord blood, or blood e.g. mobilised peripheral blood, which upon administration to a subject differentiate into mature immune effector cells. In preferred embodiments, the immune effector cell is a T-cell or an NK cell. Primary cells, e.g. cells isolated from a subject to be treated or from a donor subject may be used, optionally with an intervening cell culture step (e.g. to expand the cells), or alternatively other established cultured cells or cell lines (e.g. NK cell lines such as the NK92 cell line) may be used.

The term "directed against the antigen CLPTM1" is synonymous with "specific for CLPTM1" or "anti-CLPTM1", that is it means simply that the CAR is capable of binding specifically to CLPTM1. In particular, the binding domain of the CAR is capable of binding specifically to CLPTM1 (more particularly when the CAR is expressed on the surface of an immune effector cell). Specific binding may be distinguished from non-specific binding to a non-target entity (in this case an entity other than CLPTM1). Thus, an immune effector cell expressing the CAR according to the present invention is redirected to bind specifically to and exhibit cytotoxicity to (e.g. kill) a CLPTM1-expressing target cell. Alternatively expressed, the immune effector cell is modified to redirect cytotoxicity towards target cells expressing CLPTM1.

In an embodiment, specific binding to CLPTM1 may mean that the binding domain (or CAR comprising the binding domain) binds to or associates with CLPTM1 (or more particularly a target cell expressing CLPTM1 on its cell surface) with an affinity or Ka (i.e. equilibrium association constant) of greater than or equal to about $10^5 M^{-1}$, e.g. at least $10^6 M^{-1}$, $10^7 M^{-1}$, or $10^8 M^{-1}$.

The binding of the binding domain of the CAR to its target on the surface of the target cell delivers an activation stimulus to the CAR-containing cell, resulting in induction of effector cell signalling pathways. Binding to the target entity (e.g. target antigen) may thereby trigger proliferation, cytokine production, phagocytosis, lytic activity and/or production of molecules that can mediate cell death of the target cell in an MHC-independent manner.

In a CAR of the present invention an "antigen binding domain", which is derived from the variable region sequences of an antibody specific for CLPTM1, may be provided in various formats, as long as it comprises the $V_L$ and $V_H$ sequences as defined above. It may accordingly be, or may correspond to, a natural or synthetic antibody sequence. Accordingly, the nucleotide sequence encoding the antigen binding domain in the nucleic acid molecules of the invention may be derived from, or may correspond to a natural sequence or may encode a genetically engineered product. Thus the antigen binding domain may be (or more precisely may correspond to) a fragment of an antibody specific for CLPTM1 comprising the variable region (the antibody light chain and heavy chain variable regions; the $V_L$ and $V_H$ regions), e.g. a Fv or Fab or Fab2 or the light and heavy chain variable regions can be joined together in a single chain and in either orientation (e.g., $V_L$-$V_H$ or $V_H$-$V_L$). The $V_L$ and/or $V_H$ sequences may be modified. In particular the framework regions may be modified (e.g. substituted, for example to humanise the antigen binding domain).

In a preferred embodiment, the binding domain is a single chain antibody (scFv) derived from an antibody specific for CLPTM1. The single chain antibody may be cloned using known and readily available techniques from the V region genes of a hybridoma producing an antibody for CLPTM1.

"Single-chain Fv antibody" or "scFv" refers to an engineered antibody consisting of a light chain variable region ($V_L$) and a heavy chain variable region ($V_H$) connected to one another directly or via a peptide linker sequence.

"Heavy chain variable region" or "$V_H$" refers to the fragment of the heavy chain of an antibody that contains three CDRs (complementarity determining regions) interposed between flanking stretches known as framework regions, which are more highly conserved than the CDRs and form a scaffold to support the CDRs. "Light chain variable region" or "$V_L$" refers to the fragment of the light chain of an antibody that contains three CDRs interposed between framework regions.

"Fv" refers to the smallest fragment of an antibody to bear the complete antigen binding site. An Fv fragment consists of the variable region of a single light chain bound to the variable region of a single heavy chain.

In one preferred embodiment the $V_L$ and $V_H$ are linked together by a linker sequence. More precisely this may be referred to as a "variable region linker sequence", which is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. The linker sequence may be used to provide for appropriate spacing and conformation of the molecule.

More preferably, the $V_L$ sequence is linked to $V_H$ by a linker sequence. The linker sequence may be between 1-30, more preferably 1-25, 1-22 or 1-20, amino acids long. The linker may be a flexible linker. Suitable linkers can be readily selected and can be of any of a suitable length, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids or longer.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein.

The $V_L$ and $V_H$ sequences may, if desired, be humanised by modifying one or more of the framework regions to correspond to at least one human framework region. A "human framework region" refers to a wild type (i.e., naturally occurring) framework region of a human immunoglobulin variable region, an altered framework region of a human immunoglobulin variable region with less than about 50% (e.g., preferably less than about 45%, 40%, 30%, 25%, 20%, 15%, 10%, 5%, or 1%) of the amino acids in the region deleted or substituted (e.g., with one or more amino acid residues of a nonhuman immunoglobulin framework region at corresponding positions), or an altered framework region of a nonhuman immunoglobulin variable region with less than about 50% (e.g., less than 45%, 40%, 30%, 25%, 20%, 15%, 10%, or 5%) of the amino acids in the region deleted or substituted (e.g., at positions of exposed residues and/or with one or more amino acid residues of a human immunoglobulin framework region at corresponding positions) so that, in one aspect, immunogenicity is reduced.

The CAR, and more particularly the extracellular domain thereof, may also comprise a signal sequence (or targeting domain). Such a sequence will generally be provided at the N-terminal end of the molecule (construct) and may function to, co-translationally or post-translationally, direct transfer of the molecule. In particular, the signal sequence may be a sequence which targets the CAR to the plasma membrane of the immune effector cell. This may be linked directly or indirectly (e.g. via a linker sequence) to the binding domain, generally upstream of the binding domain, at the N-terminal end of the CAR molecule/construct.

The binding domain of the CAR is generally followed by a hinge domain. The hinge region in a CAR is generally between the transmembrane domain and the binding domain. In certain embodiments, a hinge region is an immunoglobulin hinge region and may be a wild type immunoglobulin hinge region or an altered wild type immunoglobulin hinge region, for example a truncated hinge region. Other exemplary hinge regions which may be used include the hinge region derived from the extracellular regions of type 1 membrane proteins such as CD8a, CD4, CD28 and CD7, which may be wild-type hinge regions from these molecules or may be altered. Preferably the hinge region is, or is derived from, the hinge region of human CD8a, CD4, CD28 or CD7.

The transmembrane domain may be based on or derived from the transmembrane domain of any transmembrane protein. Typically it may be, or may be derived from, a transmembrane domain from CD8α, CD28, CD4, CD3ζ CD45, CD9, CD16, CD22, CD33, CD64, CD80, CD86, CD134, CD137, and CD154, preferably from a human said protein. In one embodiment, the transmembrane domain may be, or may be derived from, a transmembrane domain from CD8α, CD28, CD4, or CD3ζ, preferably from human CD28, CD4, or CD3ζ. In another embodiment the transmembrane domain may be synthetic in which case it would comprise predominantly hydrophobic residues such as leucine and valine. The "intracellular signalling domain" refers to the part of the CAR protein that participates in transducing the message of effective CAR binding to a target entity into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the term "intracellular signalling domain" refers to the portion of a protein which transduces the effector function signal and that directs the cell to perform a specialized function. While the entire intracellular signalling domain can be employed, in many cases it is not necessary to use the entire domain. To the extent that a truncated portion of an intracellular signalling domain is used, such truncated portion may be used in place of the entire domain as long as it transduces the effector function signal. The term intracellular signalling domain is meant to include any truncated portion of the intracellular signalling domain sufficient to transduce effector function signal. The intracellular signalling domain is also known as the, "signal transduction domain," and is typically derived from portions of the human CD3ζ or FcRγ chains.

Additionally to allow or to augment full activation of the immune effector cell the CAR may be provided with a secondary or co-stimulatory domain. Thus, the intracellular signalling domain may initiate target dependent primary activation (i.e. may be a primary cytoplasmic signalling sequence) and the co-stimulatory domain may act in a target-independent manner to provide a secondary or co-stimulatory signal (secondary cytoplasmic signalling sequence(s)). Primary cytoplasmic signalling sequences may regulate primary activation, including in an inhibitory way. Primary cytoplasmic signalling sequences that act in a co-stimulatory manner may contain signalling motifs which are known as immunoreceptor tyrosine-based activation motif or ITAMs.

Examples of ITAM containing primary cytoplasmic signalling sequences that may be used in the invention include those derived from TCRζ, FcRγ, FcRβ, CD3γ, CD3δ, CD3ε, CD5, CD22, CD79a, CD79b and CD66d. In certain particular embodiments, the intracellular signalling domain is derived from CD3ζ or FcRγ, preferably human CD3ζ or FcRγ.

The term "co-stimulatory signalling domain" or "co-stimulatory domain" refers to the portion of the CAR comprising the intracellular domain of a co-stimulatory molecule. Co-stimulatory molecules are cell surface molecules other than antigen receptors or Fc receptors that provide a second signal required for efficient activation and function of an immune effector cell (e.g. a T-cell) upon binding to antigen. Examples of such co-stimulatory molecules include CD27, CD28, 4-IBB (CD137), OX40 (CD134), CD30, CD40, PD-1, ICOS (CD278), LFA-1, CD2, CD7, LIGHT, NKD2C, B7-H2 and a ligand that specifically binds CD83, more particularly the intracellular domains of such molecules. Preferably the molecules are human. Accordingly, while exemplary or preferred co-stimulatory domains are derived from 4-1BB, CD28 or OX40 (CD134), other co-stimulatory domains are contemplated for use with the CARs described herein. The co-stimulatory domains may be used singly or in combination (i.e. one or more co-stimulatory domains may be included. The inclusion of one or more co-stimulatory signalling domains may enhance the efficacy and expansion of immune effector cells expressing the CARs.

The nucleic acid molecule of the invention may be an isolated nucleic acid molecule and may further include DNA or RNA or chemical derivatives of DNA or RNA, including molecules having a radioactive isotope or a chemical adduct such as a fluorophore, chromophore or biotin ("label"). Thus the nucleic acid may comprise modified nucleotides. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "nucleic acid molecule" specifically includes single and double stranded forms of DNA and RNA.

Likewise methods for preparing a nucleic acid molecule encoding the CAR are also well known e.g. conventional polymerase chain reaction (PCR) cloning techniques can be used to construct the nucleic acid molecule. The nucleic acid molecule can be cloned into a general purpose cloning vector such as pENT (Gateway), pUC19, pBR322, pBluescript vectors (Stratagene Inc.) or pCR TOPO® from Invitrogen Inc. The resultant nucleic acid construct (recombinant vector) carrying the nucleic acid molecule encoding the CAR can then be subcloned into expression vectors or viral vectors for protein expression, e.g. in mammalian cells. This may be for preparation of the CAR protein, or for expression in immune effector cells, e.g. in human T cells or in NK cells or cell lines. Further the nucleic acid may be introduced into mRNA expression vectors for production of mRNA encoding the CAR. The mRNA may then be transferred into immune effector cells.

Thus, the nucleic acid molecule may be introduced into a cell in a vector or as a nucleic acid molecule or recombinant construct. Methods of heterologous gene expression are known in the art, both in terms of construct/vector preparation and in terms of introducing the nucleic acid molecule (vector or construct) into the cell. Thus, promoters and/or other expression control sequences suitable for use with mammalian cells, in particular immune effector cells (e.g. lymphoid cells or NK cells), and appropriate vectors etc. (e.g. viral vectors) are well known in the art.

Vectors or constructs (nucleic acid molecules) may be introduced into a cell of the invention by a variety of means, including chemical transfection agents (such as calcium phosphate, branched organic compounds, liposomes or cationic polymers), electroporation, cell squeezing, sonoporation, optical transfection, hydrodynamic delivery, or viral transduction. In a preferred embodiment, a vector or construct is introduced by viral transduction. This may allow for more persistent expression of the CAR. However, in some situations, e.g. in clinical trials, or in some clinical situations, it may be desirable to have a more transient period of expression of CAR protein. In such a situation it may be desirable to deliver the nucleic acid molecule to the immune effector cell as mRNA. mRNA expression vectors for production of mRNA may be prepared according to methods known in the art (e.g. using Gateway Technology) and are known in the art (e.g. pCIpA102, Sæbøe-Larssen et al, 2002, J. Immunol. Methods 259, p 191-203 and pCIpA120-G, Wälchli et al, 2011, PLoS ONE 6 (11) e27930).

The mRNA can be produced in vitro by e.g. in vitro transcription. The mRNA may then be introduced into the immune effector cells, e.g. as naked mRNA, e.g. by electroporation (as described for example in Almasbak et al., Cytotherapy 2011, 13, 629-640, Rabinovich et al., Hum. Gene Ther., 2009, 20, 51-60 and Beatty et al., Cancer Immunol. Res. 2014, 2, 112-120. Alternatively, mRNA may be introduced by other means such as by liposomes or cationic molecules etc. Heterologous nucleic acid molecules introduced into a cell may be expressed episomally, or may be integrated into the genome of the cell at a suitable locus.

Thus the nucleic acid molecule may be introduced or inserted into a vector. The term "vector" as used herein refers to a vehicle into which the nucleic acid molecule may be introduced (e.g. be covalently inserted) so as to bring about the expression of the CAR protein or mRNA and/or the cloning of the nucleic acid molecule. The vector may accordingly be a cloning vector or an expression vectors.

The nucleic acid molecule may be inserted into a vector using any suitable methods known in the art, for example, without limitation, the vector may be digested using appropriate restriction enzymes and then may be ligated with the nucleic acid molecule having matching restriction ends.

Expression vectors can contain a variety of control sequences, which refer to nucleic acid sequences necessary for the transcription and possibly translation of an operatively linked coding sequence in a particular host cell. In addition to control sequences that govern transcription and translation, vectors may contain additional nucleic acid sequences that serve other functions, including for example for replication, selectable markers etc.

The expression vector should have the necessary 5' upstream and 3' downstream regulatory elements such as promoter sequences such as CMV, PGK and EF1 a promoters, ribosome recognition and binding TATA box, and 3' UTR AATAAA (SEQ ID NO: 94) transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing the CAR. This provides a molecular switch capable of turning expression of the nucleic acid molecule on or off. Examples of inducible promoters include, but are not limited to a metallothionine promoter, a glucocorticoid promoter, a progesterone promoter, or a tetracycline promoter.

Further the expression vector may contain 5' and 3' untranslated regulatory sequences that may function as enhancer sequences, and/or terminator sequences that can facilitate or enhance efficient transcription of the nucleic acid molecule.

Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI—derived artificial chromosome (PAC), bacteriophages such as lambda phage or MI 3 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4N5-DEST™ and pLenti6/V5-DEST™ for lentivirus-mediated gene transfer and expression in mammalian cells.

In certain embodiments viral vectors are preferred. A viral vector can be derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the nucleic acid molecule of the invention in place of nonessential viral genes. The vector and/or particle can be utilized for the purpose of transferring DNA, RNA or other nucleic acids into cells either in vitro or in vivo.

Accordingly, a further aspect of the invention includes a viral particle comprising a nucleic acid molecule as defined and described herein, or a preparation or composition comprising such viral particles. Such a composition may also contain at least one physiologically acceptable carrier.

Numerous forms of viral vectors are known in the art. In certain embodiments, the viral vector is a retroviral vector or a lentiviral vector. The vector may be a self-inactivating vector in which the right (3') LTR enhancer-promoter region, known as the U3 region, has been modified (e.g., by deletion or substitution) to prevent viral transcription beyond the first round of viral replication. Consequently, the vectors are capable of infecting and then integrating into the host genome only once, and cannot be passed further.

The retroviral vectors for use herein can be derived from any known retrovirus, e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV), human T cell leukemia viruses, HTLV-1 and HTLV-2, and the lentiviral family of retroviruses, such as Human Immunodeficiency Viruses, HrV-1, HIV-2, simian immunodeficiency virus (SIV), feline immunodeficiency virus (FIV), equine immunodeficiency virus (EIV), and other classes of retroviruses.

A lentiviral vector is derived from a lentivirus, a group (or genus) of retroviruses that give rise to slowly developing disease. Viruses included within this group include HIV (human immunodeficiency virus; including HIV type 1, and HIV type 2).

A retroviral packaging cell line (typically a mammalian cell line) may be used to produce viral particles, which may then be used for transduction of the immune effector cells.

Illustrative viral vectors are described in WO2002087341, WO2002083080, WO2002082908, WO2004000220 and WO2004054512.

It is within the scope of the invention to include gene segments that cause immune effector cells e.g., T cells, to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., Cell 11 (1):223-232, 1977) which confers ganciclovir sensitivity; the cellular hypoxanthinephosphribosyltransferase (HPRT) gene, the cellular adenine phosphoribosyltransferase (APRT) gene, bacterial cytosine deaminase, (Mullen et al., Proc. Natl. Acad. Sci. USA. 89:33-37 (1992)).

In some embodiments it may be useful to include in the genetically modified immune effector cells, such as T cells, a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine daminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374-3378, 1991.

For cloning of the nucleic acid molecule the vector may be introduced into a host cell (e.g., an isolated host cell) and such "production host cells" containing a cloning vector of the invention may form a further aspect of the invention. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. A production host cell may alternatively contain an mRNA expression vector comprising the nucleic acid molecule.

The nucleic acid molecules or vectors are introduced into a host cell (e.g. a production host cell or an immune effector cell) using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or a may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into viral particles or virions prior to contact with a cell.

An "immune effector cell," is any cell of the immune system that has one or more effector functions (e.g., cytotoxic cell killing activity, secretion of cytokines, induction of ADCC and/or CDC). Representative immune effector cells thus include T lymphocytes, in particular cytotoxic T cells (CTLs; CD8+ T cells) and helper T cells (HTLs; CD4+ T cells). Other populations of T cells are also useful herein, for example naive T cells and memory T cells. Other immune effector cells include NK cells, NKT cells, neutrophils, and macrophages. As noted above, immune effector cells also include progenitors of effector cells, wherein such progenitor cells can be induced to differentiate into an immune effector cells in vivo or in vitro.

T-cells, particularly CD8+ T-cells, and NK cells represent preferred immune effector cells according to the invention.

The term "NK cell" refers to a large granular lymphocyte, being a cytotoxic lymphocyte derived from the common lymphoid progenitor which does not naturally comprise an antigen-specific receptor (e.g. a T-cell receptor or a B-cell receptor). NK cells may be differentiated by their $CD3^-$, $CD56^+$ phenotype. The term as used herein thus includes any known NK cell or any NK-like cell or any cell having the characteristics of an NK cell. Thus primary NK cells may be used or in an alternative embodiment, a NK cell known in the art that has previously been isolated and cultured may be used. Thus a NK cell-line may be used. A number of different NK cells are known and reported in the literature and any of these could be used, or a cell-line may be prepared from a primary NK cell, for example by viral transformation (Vogel et al. 2014, Leukemia 28:192-195). Suitable NK cells include (but are by no means limited to), in addition to NK-92, the NK-YS, NK-YT, MOTN-1, NKL, KHYG-1, HANK-1, or NKG cell lines In a preferred embodiment, the cell is an NK-92 cell (Gong et al. 1994, Leukemia 8:652-658), or a variant thereof. A number of different variants of the original NK-92 cells have been prepared and are described or available, including NK-92 variants which are non-immunogenic. Any such variants can be used and are included in the term "NK-92". Variants of other cell lines may also be used.

The present invention provides methods for making the immune effector cells which express the CAR as described herein. In one embodiment, the method comprises transfecting or transducing immune effector cells such that the immune effector cells express one or more CAR as described herein.

In certain embodiments, the immune effector cells may be isolated from a subject and modified by introduction of the nucleic acid molecule without further manipulation in vitro. Such cells can then be directly re-administered into the subject. In further embodiments, the immune effector cells are first activated and stimulated to proliferate in vitro prior to being modified to express a CAR. In this regard, the immune effector cells may be cultured before or after being genetically modified (i.e., transduced or transfected to express a CAR as described herein).

T cells can be obtained from a number of sources, including peripheral blood mononuclear cells, bone marrow, lymph nodes tissue, cord blood, thymus issue, tissue from a site of infection, ascites, pleural effusion, spleen tissue, and tumours. In certain embodiments, T cells can be obtained from a unit of blood collected from the subject using any number of techniques known to the skilled person, such as FICOLL™ separation. In one embodiment, cells from the circulating blood of a subject are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium and/or magnesium or may lack many if not all divalent cations. As would be appreciated by those of ordinary skill in the art, a washing step may be accomplished by methods known to those in the art, such as by using a semiautomated flowthrough centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CDI Ib, CD16, HLA-DR, and CD8. Flow cytometry and cell sorting may also be used to isolate cell populations of interest for use in the present invention.

PBMC may be used directly for genetic modification using methods as described herein. In certain embodiments, after isolation of PBMC, T lymphocytes are further isolated and in certain embodiments, both cytotoxic and helper T lymphocytes can be sorted into naïve, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD 127, and positive for granzyme B and perforin. In some embodiments, naive CD 8+T lymphocytes are characterized by the expression of phenotypic markers of naive T cells including CD62L, CCR7, CD28, CD3, CD 127, and CD45RA.

The immune effector cells, such as T cells, can be modified following isolation, or the immune effector cells can be activated and expanded (or differentiated in the case of progenitors) in vitro prior to being modified. In another embodiment, the immune effector cells, such as T cells, are modified by introduction of the nucleic acid molecules and then are activated and expanded in vitro. Methods for activating and expanding T cells are known in the art and are described, for example, in U.S. Pat. Nos. 6,905,874; 6,867, 041; 6,797,514; WO2012079000. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

Standard procedures may be used for storage, e.g. cryopreservation, of the modified immune effector cells and/or preparation for use in a human or other subject.

In yet another aspect, the present invention provides a bi-specific binding agent comprising a first binding domain capable of binding to CLPTM1 and a second binding domain capable of binding to a cytotoxic immune cell.

This aspect of the invention acts to recruit cytotoxic immune cells to a cell expressing CLPTM1 at its surface by providing a 'bridging' binding moiety that allows such cytotoxic cells to recognise CLPTM1 without requiring any further modification of said cells (e.g. to express a molecule capable of binding CLPTM1 directly such as a CAR).

Such bi-specific binding agents comprise two separate binding domains having specificity for different cell surface receptors. In a preferred aspect, one or both of the binding domains may be an antibody. Thus, the bi-specific binding agents according to this aspect of the invention may comprise first and/or second antibody domains, and in a preferred embodiment comprise first and second antibody domains, wherein the first antibody domain is capable of binding to CLPTM1 and the second antibody domain is capable of binding to a cytotoxic immune cell.

The respective binding domains of the bi-specific binding agent may therefore include an antibody-based or antibody-derived domain (i.e. region or part etc.) which may be an antibody, as defined above. In particular the binding domain will be an antibody fragment which includes the, or a, binding domain of an antibody, or a derivative thereof, e.g. a molecule which includes an antibody binding domain or a derivative thereof. This can be any antibody fragment or molecule as described above Preferably, the first and second binding domains of a bi-specific binding agent are single chain antibodies (scFv), as defined above. Thus, according to a preferred embodiment, the first binding domain is a scFv derived from an antibody specific for CLPTM1. The single chain antibody may be cloned using known and readily available techniques from the V region genes of a hybridoma producing an antibody for CLPTM1.

In one preferred embodiment the $V_L$ and $V_H$ are linked together by a linker sequence. More precisely this may be referred to as a "variable region linker sequence", which is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. The linker sequence may be used to provide for appropriate spacing and conformation of the molecule.

More preferably, the $V_L$ sequence is linked to $V_H$ by a linker sequence. The linker sequence may be between 1-30, more preferably 1-25, 1-22 or 1-20, amino acids long. The linker may be a flexible linker. Suitable linkers can be readily selected and can be of any of a suitable length, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids or longer.

Exemplary flexible linkers include glycine polymers $(G)n$, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein.

The $V_L$ and $V_H$ sequences may, if desired, be humanised by modifying one or more of the framework regions to correspond to at least one human framework region. A "human framework region" refers to a wild type (i.e., naturally occurring) framework region of a human immunoglobulin variable region, an altered framework region of a human immunoglobulin variable region with less than about 50% (e.g., preferably less than about 45%, 40%, 30%, 25%, 20%, 15%, 10%, 5%, or 1%) of the amino acids in the region deleted or substituted (e.g., with one or more amino acid residues of a nonhuman immunoglobulin framework region at corresponding positions), or an altered framework region of a nonhuman immunoglobulin variable region with less than about 50% (e.g., less than 45%, 40%, 30%, 25%, 20%, 15%, 10%, or 5%) of the amino acids in the region deleted or substituted (e.g., at positions of exposed residues and/or with one or more amino acid residues of a human immunoglobulin framework region at corresponding positions) so that, in one aspect, immunogenicity is reduced.

Preferably, the first and second binding domains of a bi-specific binding agent according to this aspect of the present invention are provided as a single polypeptide chain. The domains may therefore be connected by a linker sequence as hereinbefore described.

The second binding domain may bind to any cytotoxic immune cell capable of effecting an immune response against a target cell (i.e. a cell expressing CLPTM1 at its surface). Thus, any of the aforementioned cytotoxic immune cells may be the target for the second binding domain of a bi-specific binding agent according to this aspect of the present invention, and suitable receptors found on different types of immune cell are known to one of skill in the art. In a particularly preferred embodiment, the cytotoxic immune cell is a cytotoxic T-cell.

As noted above, according to a preferred embodiment, the second binding domain of the bi-specific binding agent is capable of binding to a cytotoxic T-cell. In preferred embodiments, the second binding domain is capable of binding to a component of CD3 (the T-cell receptor complex) on the surface of a cytotoxic T-cell, and in particularly preferred embodiments, is capable of binding to CD3ϵ on the surface of a cytotoxic T-cell.

In a preferred embodiment, the bi-specific binding agent is a Bi-specific T-cell Engager (BiTE®). The first and second binding domains of a BiTE are scFvs of monoclonal antibodies for CD3ϵ on T-cells and a surface molecule on a target cell, connected via a non-immunogenic linker (e.g. a 5-amino-acid repetitive linker). Thus, in the present invention, the bi-specific binding agent may preferably be a BiTE comprising a first binding domain being an scFv capable of binding to CLPTM1 and a second binding domain being an scFv capable of binding to CD3E, wherein the first and second binding domains are connected by a linker.

As noted above, any of the therapeutic agents of the invention have utility in therapy. Accordingly, further aspects of the invention include:

a composition, particularly a therapeutic or pharmaceutical composition, comprising any one of the therapeutic agents as defined herein and at least one physiologically acceptable carrier or excipient;

a therapeutic agent or a composition of the invention as defined herein for use in the treatment of cancer;

a method of treating cancer, said method comprising administering to a subject in need thereof a therapeutic agent of the invention as defined herein, particularly an effective amount of said agent or composition; and use of a therapeutic agent of the invention as defined herein for the manufacture of a medicament (or composition) for use in cancer therapy.

By binding specifically is meant that an agent is capable of binding to CLPTM1 (or an extracellular domain thereof) in a manner which distinguishes it from binding to a non-target molecule. Thus, binding to a non-target molecule may be negligible or substantially reduced as compared to binding to CLPTM1. Binding agents, antibodies and CARs as defined above therefore have a specific binding affinity for CLPTM1 i.e. they are an affinity binding partner for CLPTM1, or more particularly for an extracellular domain thereof.

Agents (including antibodies having immune effector function, cells expressing CARs, binding agent-drug (e.g. toxin) conjugates and bi-specific binding agents) of or for use according to the invention capable of binding to CLPTM1 preferably bind to the extracellular domain of CLPTM1. As discussed above, the extracellular domain of CLPTM1 comprises approximately 350 amino acids, and thus the agents of the present invention may bind to any portion of this domain in order to target a cell which expresses this receptor. Thus, the agent capable of binding to CLPTM1 may bind to a polypeptide having an amino acid sequence as set forth in SEQ ID NO: 2. In a particular embodiment, the agent may bind to a polypeptide having or comprising an amino acid sequence as set forth in SEQ ID NO:5. In a further embodiment, the agent may bind to a polypeptide having or comprising an amino acid sequence as set forth in SEQ ID NO: 6. In yet another embodiment, the agent may bind to a polypeptide having or comprising an amino acid sequence as set forth in SEQ ID NO: 3 and/or to a polypeptide having or comprising an amino acid sequence as set forth in SEQ ID NO: 4. In another embodiment, the agent may bind to a polypeptide having or comprising an amino acid sequence as set forth in SEQ ID NO:7. SEQ ID NOs: 3, 4, 5, 6 and 7 represent parts or sub-sequences of the extracellular domain.

Epitope mapping studies to identify the binding site for an anti-CLPTM1 antibody have been performed, and Example 4 below describes the elucidation of the binding site in the ECD of CLPTM1 (SEQ ID NO:2) for an anti-CLPTM1 antibody which demonstrates antagonist activity against this receptor. The common denominator of this antibody is indicated to be PKD (SEQ ID NO: 8) at positions 97-99 of SEQ ID NO: 2. Accordingly, in a still further embodiment, the agent may bind to a polypeptide having or comprising the sequence PKD (SEQ ID NO:8), e.g. a polypeptide having or comprising an amino acid sequence as set forth in SEQ ID NO:9 (PKDT), or having or comprising any one of SEQ ID NOs:10-36 or any one of SEQ ID NOs: 37 to 40. A second epitope is also identified in Example 4. Accordingly, in a yet further embodiment the agent may bind to a polypeptide having or comprising an amino acid sequence as set forth in any one of SEQ ID NOs:41-47. Alternatively, the agents of the present invention may bind to any one of SEQ ID NOs: 48 to 54, or any one of SEQ ID NOs: 48 to 55, or any one of SEQ ID NOs: 48 to 57.

Any of the therapeutic agents or therapeutic agents for use described herein, and in particular a therapeutic agent being a conjugate comprising a binding agent capable of binding to CLPTM1 conjugated to a drug, a bi-specific binding agent having a first domain capable of binding to CLPTM1 and a second binding domain capable of binding to a cytotoxic immune cell or a cytotoxic immune cell expressing a CAR capable of binding to CLPTM1, may comprise a binding agent, first binding domain or CAR which may comprise a binding region or domain based on or derived or obtained from the antibodies 7G12 or 59D04. Thus the binding agent, binding region or domain or CAR may comprise, respectively:

(i) a VL region having an amino acid sequence as set forth in SEQ ID NO: 63, or an amino acid sequence having at least 80% sequence identity thereto, and a VH region having an amino acid sequence as set forth in SEQ ID NO: 62, or an amino acid sequence having at least 80% sequence identity thereto; or (ii) a VL region having an amino acid sequence as set forth in SEQ ID NO: 60, or an amino acid sequence having at least 80% sequence identity thereto, and a VH region having an amino acid sequence as set forth in SEQ ID NO: 59, or an amino acid sequence having at least 80% sequence identity thereto.

In particular embodiments the level of amino acid sequence identity may be at least 85, 86, 87, 88, 89, 90, 91, 92, 93, 94, 95, 96, 97, or 99%. Sequence identity may be determined as described above.

In some embodiments the framework regions of said VL and VH sequences have at least 80% amino acid sequence identity to the framework regions of SEQ ID NOS. 62 or 60 and/or 63 or 59, respectively. For example in some embodiments the framework regions of SEQ ID NOS: 62 and 63 may be humanised.

This aspect of the invention also provides a therapeutic agent (and in particular an isolated specific therapeutic agent) which binds human CLPTM1, wherein said therapeutic agent is a conjugate comprising a binding agent capable of binding to CLPTM1 conjugated to a drug, a bi-specific binding agent having a first binding domain capable of binding to CLPTM1 and a second binding domain capable of binding to a cytotoxic immune cell, or a cytotoxic immune cell expressing a CAR capable of binding to CLPTM1; and wherein said binding agent, first binding domain or the CAR comprises the complementarity-determining regions (CDRs) VLCDR1, VLCDR2, VLCDR3, VHCDR1, VHCDR2 and VHCDR3, wherein (i) each of said CDRs has an amino acid sequence as follows:
VLCDR1 has the sequence set forth in SEQ ID NO: 66;
VLCDR2 has the sequence set forth in SEQ ID NO: 67;
VLCDR3 has the sequence set forth in SEQ ID NO: 68;
VHCDR1 has the sequence set forth in SEQ ID NO: 69;
VHCDR2 has the sequence set forth in SEQ ID NO: 70; and
VHCDR3 has the sequence set forth in SEQ ID NO: 71;
or, for each sequence, an amino acid sequence with at least 85% sequence identity thereto,
or wherein one or more of said CDR sequences of SEQ ID NOs: 66 to 71 (or more particularly one more of said CDR1 and CDR2 sequences) may optionally be modified by substitution, addition or deletion of 1 to 3 (e.g. 1 or 2) amino acids; or (ii) each of said CDRs has an amino acid sequence as follows:
VLCDR1 has the sequence set forth in SEQ ID NO: 72;
VLCDR2 has the sequence set forth in SEQ ID NO: 73;
VLCDR3 has the sequence set forth in SEQ ID NO: 74;
VHCDR1 has the sequence set forth in SEQ ID NO: 75;
VHCDR2 has the sequence set forth in SEQ ID NO: 76; and
VHCDR3 has the sequence set forth in SEQ ID NO: 77;
or, for each sequence, an amino acid sequence with at least 85% sequence identity thereto,
or wherein one or more of said CDR sequences of SEQ ID NOs: 72 to 77 (or more particularly one more of said CDR1 and CDR2 sequences) may optionally be modified by substitution, addition or deletion of 1 to 3 (e.g. 1 or 2) amino acids.

By "or, for each sequence, an amino acid sequence with at least 85% sequence identity thereto" is meant that each of the said CDRs may have the amino acid sequence specified in the relevant SEQ ID NO, or an amino acid sequence with at least 85% sequence identity thereto. Thus, in parts (i) and (ii) respectively, VLCDR1 has the sequence set forth in SEQ ID NO: 66 or 72, or an amino acid sequence with at least 85% sequence identity to SEQ ID NO: 66 or 72; VLCDR2 has the sequence set forth in SEQ ID NO: 67 or 73, or an amino acid sequence with at least 85% sequence identity to SEQ ID NO: 67 or 73; VLCDR3 has the sequence set forth in SEQ ID NO: 68 or 74, or an amino acid sequence with at least 85% sequence identity to SEQ ID NO: 68 or 74; VHCDR1 has the sequence set forth in SEQ ID NO: 69 or 75, or an amino acid sequence with at least 85% sequence identity to SEQ ID NO: 69 or 75; VHCDR2 has the sequence set forth in SEQ ID NO: 70 or 76, or an amino acid sequence with at least 85% sequence identity to SEQ ID NO: 70 or 76; and VHCDR3 has the sequence set forth in SEQ ID NO: 71 or 77, or an amino acid sequence with at least 85% sequence identity to SEQ ID NO: 71 or 77.

In particular embodiments of the invention, in parts (i) and (ii) respectively VLCDR1 has (by which is meant herein consists of) the sequence set forth in SEQ ID NO: 66 or 72, VLCDR2 has the sequence set forth in SEQ ID NO: 67 or 73, VLCDR3 has the sequence set forth in SEQ ID NO: 68 or 74, VHCDR1 has the sequence set forth in SEQ ID NO: 69 or 75, VHCDR2 has the sequence set forth in SEQ ID NO: 70 or 76; and VHCDR3 has the sequence set forth in SEQ ID NO: 70 or 77. The sequences used in the therapeutic agent may comprise the sequences described herein.

The therapeutic agent of this aspect of the invention may alternatively be defined as comprising a VL sequence and a VH sequence each comprising three CDR sequences, wherein the CDR sequences are as defined above.

In embodiments of this aspect of the invention the sequence identity may be at least 86, 87, 88, 89, 90, 91, 92, 93, 94, 95, 96, 97, or 99%. Sequence identity may be determined as described above.

In some embodiments the amino acid sequences of at least CDR3 of said VL and VH sequences are unmodified, and preferably the amino acid sequences of all of the CDRs are unmodified.

In some embodiments the combined sequences of the CDRs have at least 90% sequence identity to the combined sequences set forth in SEQ ID NOs: 66 to 71, or SEQ ID NOs: 72 to 76, respectively.

By the "combined sequence of the CDR sequences" (or the combined sequences of the CDRs) is meant the sequence formed when the sequences are assembled end-to-end (even if in the molecule of interest they would appear with intervening sequences). In other words, the combined sequence of the CDR sequences is the amino acid sequence obtained when the CDR sequences are joined together in the order listed above (i.e. VLCDR1-VLCDR2-VLCDR3-VHCDR1-VHCDR2-VHCDR3), thus the combined sequence has at its N-terminus the N-terminal amino acid of VLCDR1; the C-terminus of VLCDR1 is joined directly to the N-terminus of VLCDR2; the C-terminus of VLCDR2 is joined directly to the N-terminus of VLCDR3; the C-terminus of VLCDR3 is joined directly to the N-terminus of VHCDR1; the C-terminus of VHCDR2 is joined directly to the N-terminus of VHCDR3; and the C-terminal amino acid of VHCDR3 forms the C-terminus of the combined sequence. By "joined directly" herein is meant that the N-terminal amino acid of a particular CDR sequence is placed immediately next to the C-terminal amino acid of the preceding CDR sequence, with no intervening amino acids (for the purposes of sequence identity assessment).

When a CDR sequence is modified by substitution of a particular amino acid residue, the substitution may be a conservative amino acid substitution. The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus a conservative amino acid substitution may be considered to be a substitution in which a particular amino acid residue is substituted for a different amino acid in the same family. However, a substitution of a CDR residue may equally be a non-conservative substitution, in which one amino acid is substituted for another with a side-chain belonging to a different family.

Amino acid substitutions or additions in the scope of the invention may be made using a proteinogenic amino acid encoded by the genetic code, a proteinogenic amino acid not encoded by the genetic code, or a non-proteinogenic amino acid. Preferably any amino acid substitution or addition is made using a proteinogenic amino acid. The amino acids making up the sequence of the CDRs may include amino acids which do not occur naturally, but which are modifications of amino acids which occur naturally. Providing these non-naturally occurring amino acids do not alter the sequence and do not affect specificity, they may be used to generate CDRs described herein without reducing sequence identity, i.e. are considered to provide an amino acid of the CDR. For example derivatives of the amino acids such as methylated amino acids may be used.

Modifications to the amino acid sequences of the CDRs set out above may be made using any suitable technique, such as site-directed mutagenesis of the encoding DNA sequence or solid state synthesis.

Therapeutic agents of the invention comprise the above described CDRs. Additionally such molecules may contain linker moieties or framework sequences to allow appropriate presentation of the CDRs. Suitable linker molecules are well known in the art. Additional sequences may also be present which may conveniently confer additional properties, e.g. peptide sequences which allow isolation or identification of the molecules containing the CDRs such as those described hereinbefore. In such cases a fusion protein may be generated.

The CDR sequences are located in the variable domains of the heavy and light chains. The CDR sequences sit within a polypeptide framework, which positions the CDRs appropriately for antigen binding. Thus the remainder of the variable domains (i.e. the parts of the variable domain sequences which do not form a part of any one of the CDRs) constitute framework regions. The N-terminus of a mature variable domain forms framework region 1 (FR1); the polypeptide sequence between CDR1 and CDR2 forms FR2; the polypeptide sequence between CDR2 and CDR3 forms FR3; and the polypeptide sequence linking CDR3 to the constant domain forms FR4. In therapeutic agents according to this aspect of the invention the variable region framework regions may have any appropriate amino acid sequence such that the agent binds to CLPTM1 (or more particularly the ECD thereof) via its CDRs. The constant regions may, for example, be the constant regions of any mammalian (preferably human) antibody isotype.

As previously discussed, elevated levels of anti-inflammatory immune cells, including M2 macrophages, are typically associated with a negative prognosis in several cancers. Without wishing to be bound by theory, it is believed that the elevated levels of ligands for CLPTM1 may lead to immune cells in the tumour micro-environment adopting an anti-inflammatory fate rather than a pro-inflammatory fate, which reduces the ability of the immune system to attack the cells of a cancer. Thus, the various strategies provided herein for eliminating cells expressing CLPTM1 may be used to eliminate immune cells expressing this receptor, and thus relieve the anti-inflammatory effect that these immune cells can have within the tumour micro-environment.

As noted above, any of the foregoing therapeutic agents of the invention find particular utility in the treatment or prevention of cancer. The cancer may be any cancer, that is it may be a cancer of any cells or tissues of the body, including both solid tumours and other cancers.

Accordingly the present invention is applicable to any cancer. Cancer is defined broadly herein to include any neoplastic condition, and includes particularly malignant or pre-malignant conditions, as well as non-malignant conditions. The cancer may cause or result in or manifest in solid tumours, but is not limited to such, and includes also cancers of the haemopoietic system. Benign tumours are also included. However, in a particular embodiment the cancer is a malignant cancer.

The cancer may occur in any tissue or organ of the body. For example, the present invention can be used in the treatment or prevention of any of the following cancers in a patient or subject:

Acute Lymphoblastic Leukaemia (ALL), Acute Myeloid Leukaemia (AML), Adrenocortical Carcinoma, AIDS-Related Cancer (e.g. Kaposi Sarcoma and Lymphoma), Anal Cancer, Appendix Cancer, Astrocytomas, Atypical Teratoid/Rhabdoid Tumour, Basal Cell Carcinoma, Bile Duct Cancer, Extrahepatic Bladder Cancer, Bone Cancer (e.g. Ewing Sarcoma, Osteosarcoma and Malignant Fibrous Histiocytoma), Brain Stem Glioma, Brain Cancer, Breast Cancer, Bronchial Tumours, Burkitt Lymphoma, Carcinoid Tumour, Cardiac (Heart) Tumours, Cancer of the Central Nervous System (including Atypical Teratoid/Rhabdoid Tumour, Embryonal Tumours, Germ Cell Tumour, Lymphoma), Cervical Cancer, Chordoma, Chronic Lymphocytic Leukemia (CLL), Chronic Myelogenous Leukaemia (CML), Chronic Myeloproliferative Disorder, Colon Cancer, Colorectal Cancer, Craniopharyngioma, Cutaneous T-Cell Lymphoma, Bile Duct Cancer, Extrahepatic Ductal Carcinoma In Situ (DCIS), Embryonal Tumours, Endometrial Cancer, Ependymoma, Esophageal Cancer, Esthesioneuroblastoma, Ewing Sarcoma, Extracranial Germ Cell Tumour, Extragonadal Germ Cell Tumour, Extrahepatic Bile Duct Cancer, Eye Cancer (including Intraocular Melanoma and Retinoblastoma), Fibrous Histiocytoma of Bone, Gallbladder Cancer, Gastric (Stomach) Cancer, Gastrointestinal Carcinoid Tumour, Gastrointestinal Stromal Tumours (GIST), Germ Cell Tumor, Gestational Trophoblastic Disease, Glioma, Hairy Cell Leukaemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumours, Pancreatic Neuroendocrine Tumours, Kaposi Sarcoma, Kidney Cancer (including Renal Cell and Wilms Tumour), Langerhans Cell Histiocytosis, Laryngeal Cancer, Leukaemia (including Acute Lymphoblastic (ALL), Acute Myeloid (AML), Chronic Lymphocytic (CLL), Chronic Myelogenous (CML), Lip and Oral Cavity Cancer, Liver Cancer (Primary), Lobular Carcinoma In Situ (LCIS), Lung Cancer, Lymphoma, Macroglobulinemia, Waldenström, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Childhood, Multiple Myeloma/Plasma Cell Neoplasm, Mycosis Fungoides, Myelodysplastic Syndromes, Myelodysplastic/Myeloproliferative Neoplasms, Multiple Myeloma, Myeloproliferative Disorders, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Oropharyngeal Cancer, Osteosarcoma, Ovarian Cancer, Pancreatic Cancer, Pancreatic Neuroendocrine Tumours (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Urethral Cancer, Uterine Cancer, Endometrial, Uterine Sarcoma, Vaginal Cancer, Vulvar Cancer, Waldenström Macroglobulinemia, and Wilms Tumour.

In certain representative examples, the cancer may be prostate cancer, multiple myeloma, melanoma, colorectal cancer (including colon cancer and rectal cancer), gastric cancer, breast cancer, ovarian cancer, endometrial cancer, oral squamous carcinoma, pancreatic cancer, lung cancer, oral cancer, oesophageal cancer, testicular cancer, liver cancer, bladder cancer or kidney cancer.

In certain other representative embodiments, the cancer may be any cancer other than any one or any combination of colon cancer, colorectal cancer, lung cancer (e.g. primary lung cancer) or renal cancer. In one such embodiment the cancer is not colon cancer or lung cancer.

As noted above, the agents of the present invention bind to target cells expressing CLPTM1. The agents of the invention may act to inhibit the growth and/or viability of a cell expressing CLPTM1, and may thereby eliminate target cells (e.g. anti-inflammatory immune cells, such as M2 macrophages), which express CLPTM1. In one aspect, the mechanism underlying cancer therapy of the present invention is therefore the elimination of cells expressing CLPTM1, and is preferably the elimination of immunosuppressive immune cells, and more preferably Treg (regulator T-cells) or macrophages, such as M2 macrophages, which are known to have an immunosuppressive effect and which are known to infiltrate solid tumours, and which have been found to express CLPTM1 at their surface. More generally, however, this aspect of the present invention comprises the elimination of tumour-infiltrating lymphocytes expressing CLPTM1.

In another aspect of the invention the therapeutic agent acts to stimulate antigen presenting cells and thereby modulates (activates) the activity of the immune system, to treat cancer.

However, beneficially, in certain aspects of the invention tumour cells expressing CLPTM1 may additionally or alternatively be depleted or eliminated by the immunotherapeutic agents of the present invention, and thus this may represent a yet further mechanism by which the immunotherapeutic agents of the present invention may be effective in treating cancer.

In a certain embodiment the cancer is or comprises a solid tumour. More particularly where the agent is an antibody with immune effector function the cancer is or comprises a solid tumour. As noted above, any known cancer or cancer type is envisaged, including but not limited to those listed above. In certain embodiments, however, the cancer is not rectal, colon, or prostate cancer (or is not prostate or rectal cancer). In another embodiment it is not any one or more of breast, cervical, or endometrial cancer, or it is not a glioma, a sarcoma other than Ewing Sarcoma, mesothelioma or blood cell cancer. In other embodiments such cancers are included.

The cancer may be a primary or secondary cancer, i.e. a cancer which has metastasised to a secondary site in the body, including micrometastases.

The subject may be any human or non-human animal subject and in particular any mammalian subject. In addition to a human patient the subject may therefore be a livestock, domestic, zoo, laboratory, sports animal etc.

As described in Example 14 below, therapeutic agents in the form of an antibody with immune effector function or a conjugate comprising an anti-CLPTM1 binding agent conjugated to a drug are capable of inhibiting metastasis of a cancer, more particularly of reducing the number of metastases from a primary cancer. We have also observed that metastases may in general have higher surface expression of CLPTM1 compared to primary tumours.

Accordingly another aspect disclosed, or provided, herein is a therapeutic agent capable of binding to the receptor CLPTM1 at the surface of a cell and (i) inhibiting the growth and/or viability of a cell and/or (ii) stimulating an antigen-presenting immune cell, for use in inhibiting cancer metastasis, especially metastasis from breast cancer.

Also provided according to this aspect is a method of inhibiting metastasis of a cancer in a subject, said method comprising administering to said subject an effective amount of a therapeutic agent capable of binding to the receptor CLPTM1 at the surface of a cell and (i) inhibiting the growth and/or viability of a cell and/or (ii) stimulating an antigen-presenting immune cell, In particular, this may include metastases of breast cancer to the lung. Conjugates of a binding agent capable of binding to CLPTM1 with a drug, and particularly a tubulin inhibitor, are a preferred therapeutic agent according to this aspect of the invention.

In the treatment of cancer the therapeutic agents of the invention may be used in combination or conjunction with each other and/or other anti-cancer therapies, e.g. with other anti-cancer agents, including immunotherapeutic or immuno-oncological agents or chemotherapeutic agents.

The agents of the present invention may also be used in conjunction with immunotherapeutic agents that target an immune checkpoint, i.e. immune checkpoint inhibitors in the treatment of cancer. As noted above a combination therapy comprising a therapeutic agent as defined herein together with an immune checkpoint inhibitor represents one preferred aspect of the present invention. This may particularly include a therapeutic agent capable of binding to the receptor CLPTM1 at the surface of a cell and capable of (i) inhibiting the growth and/or viability of a cell, and/or (ii) stimulating an antigen-presenting immune cell. In a particular embodiment the therapeutic agent is a conjugate comprising a binding agent capable of binding to CLPTM1 conjugated to an active agent, e.g. drug, particularly an immune cell activator capable of stimulating an antigen-presenting cell, including any such agent defined herein, e.g. a tubulin inhibitor.

Checkpoint proteins keep the immune system in check by indicating to the immune system which cells are healthy and which cells should be destroyed. Checkpoint proteins act as a "brake" on the immune system by preventing T-cell activation. If a cell does not have sufficient checkpoint proteins on its surface it may be destroyed by the immune system. In the case of cancer cells, whilst there may be molecules signalling that the cell is cancerous, if there are enough checkpoint proteins on the cell surface, the cell may evade the immune response, and it has been speculated that checkpoint proteins contribute to a lack of success in some cancer immunotherapies.

The best known example of a checkpoint protein is PD-L1 (for Programme Death Ligand 1). The receptor for PD-L1 is PD-1. PD-L1 prevents T-cells from attacking healthy cells. Cancer cells may upregulate PD-L1 as a protective mechanism. When PD-L1 activates the PD-1 receptor on the surface of a T-cell, the T-cell is signalled to destroy itself. If the T-cells are programmed to selectively attack cancer cells, that set of T-cells will be destroyed and the cancer prevails.

Another checkpoint protein is cytotoxic T-lymphocyte antigen-4, or CTLA4. Once a cytotoxic T cell becomes active it expresses CTLA4 on its surface, which then competes with the co-stimulatory molecule CD28 for their mutually shared ligands, B7-1 and B7-2 on antigen-presenting cells. This balance holds cytotoxic activity in check, while allowing T cell function to proceed in a self-limited manner.

Other checkpoint proteins include CD-137 (4-1BB) which is a costimulatory checkpoint protein; lymphocyte activation gene 3 (LAG-3, CD223), a CD4-related inhibitory receptor coexpressed with PD-1 on tolerant T cells; B7 superfamily proteins B7-H3 and B7-H4; T cell protein TIM3; and phosphatidylserine (PS) which is a phospholipid in normal cells that is translocated to the outer member surface during apoptosis, suppressing the excess immune activation that would otherwise occur during processing and clearance of decaying cell matter. Externalization of PS indirectly stimulates macrophages, resulting in suppression of dendritic ell antigen presentation. Like PD-L1, externalized PS is aberrantly expressed by some tumour cells and tumour-derived microvesicles. Thus, PS is believed to be exploited by tumours to prevent adaptive tumour immunity.

Immunotherapeutic agents which may target or inhibit any of these checkpoint proteins are known as "checkpoint inhibitors". Checkpoint inhibitors (also known as immune checkpoint modulators or CPMs) are designed to lessen the effectiveness of checkpoint proteins. Ideally a CPM should expose cancers to the immune system without causing that same system to attack healthy tissue.

Several checkpoint inhibitors are known and can be used in conjunction with the agents of present invention in the treatment of cancer, for example those inhibitors described in Creelan (2014) Cancer Control 21:80-89, which is hereby incorporated by reference.

Examples of checkpoint inhibitors include: Tremelimumab (CP-675,206), a human IgG2 monoclonal antibody with high affinity to CTLA-4; Ipilimumab (MDX-010), a human IgG1 monoclonal antibody to CTLA-4; Nivolumab (BMS-936558), a human monoclonal anti-PD1 IgG4 antibody that essentially lacks detectable antibody-dependent cellular cytotoxicity (ADCC); MK-3475 (formerly lambrolizumab), a humanized IgG4 anti-PD-1 antibody that contains a mutation at C228P designed to prevent Fc-mediated ADCC; Urelumab (BMS-663513), a fully human IgG4 monoclonal anti-CD137 antibody; anti-LAG-3 monoclonal antibody (BMS-986016); and Bavituximab (chimeric 3G4), a chimeric IgG3 antibody against PS. All of these checkpoint inhibitors can be used.

An alternative strategy is to inhibit PD-L1, the ligand for PD-1, on the tumour cell surface, and therefore inhibitors of PD-L1 are may also be used in conjunction with the agents of the present invention, for example, MPDL3280A (RG7446), a human IgG1-kappa anti-PD-L1 monoclonal antibody. MED14736 is another IgG1-kappa PD-L1 inhibitor.

Another alternative approach is to competitively block the PD-1 receptor, using a B7-DC-Fc fusion protein, and such fusion proteins can also therefore be used.

In a further alternative approach an antibody to Killer cell immunoglobulin like receptor may be used as the immunotherapeutic agent. Killer cell immunoglobulin-like receptor (KIR) is a receptor on NK cells that downregulates NK cytotoxic activity. HLA class I allele-specific KIR receptors are expressed in cytolytic (CD56dimCD16+) NK cells, while CD56brightCD16− NK subset lacks these KIRs. Along these lines, inhibitory KIRs seem to be selectively expressed in the peritumoral NK cell infiltrate and thus seem to be a checkpoint pathway coopted by tumours, similar to PD-L1. As such, inhibition of specific KIRs using antibodies should cause sustained in vivo activation of NK cells. For example lirilumab (IPH2102) is fully human monoclonal antibody to KIR and can be used in a combination therapy according to the invention.

Thus, an immune checkpoint inhibitor may be broadly defined as any agent which inhibits the activity or function of a checkpoint protein. This may be an agent which binds to a checkpoint protein or to a receptor for a checkpoint protein. A checkpoint inhibitor may thus be a binding agent for a checkpoint protein or for a receptor therefor. A binding agent may be, or may be based on or derived from, an antibody. The antibody may be a natural or synthetic antibody, or a fragment or derivative thereof. As noted above, the term "antibody" is used broadly herein to include any type of antibody or antibody-based molecule. This includes not only native antibody molecules but any modified, synthetic or recombinant antibodies, as well as derivatives or fragments thereof. An antibody may thus be any molecule or entity or construct having antibody-based binding region(s), that is a binding domain(s) which is/are derived from an antibody. Accordingly, an antibody may alternatively be defined as a binding molecule comprising an antigen-binding domain obtained or derived from an antibody. The antibody may be of, or may be derived from/based on, an antibody of any convenient or desired species, class or sub-type. As noted above, the antibody may be natural, derivatised or synthetic. It may be monoclonal or polyclonal. Thus the antibody may bind to a single epitope or it may be a mixture of antibodies (or antibody molecules) binding to different epitopes.

Accordingly, the checkpoint inhibitor may be a binding molecule comprising an antigen binding domain from an antibody specific for (or directed against) a checkpoint protein or a receptor therefor. Examples of such "antibodies" (i.e. antibody-based binding molecules) include monoclonal or polyclonal antibodies, antibody fragments including Fab, Fab', F(ab')2 or Fv fragments or any fragment lacking a Fc region, chimeric (e.g. humanised or CDR-grafted) antibodies, single chain antibodies (e.g. ScFv antibodies), antibodies identified or obtained from phage display etc.

In an embodiment the immune checkpoint inhibitor is an antibody against PDL-1, PD-1, CTLA4, TIM3, CD137, CD223, PS, or a KIR on an NK cell, or it is B7-DC-Fc fusion protein.

Any of the checkpoint inhibitors described above, including the antibody to KIR, may be co-administered with a therapeutic agent as defined or described herein in relation to any aspect of the invention. In particularly preferred embodiments, the immune checkpoint inhibitor is an anti-PD1, anti-PDL1 or an anti-CTLA-4 antibody.

Any suitable antibody which recognises and binds to a cancer antigen may also be used in conjunction with the agents of the invention. Examples of cancer antigens, or targets for therapeutic antibodies, include many "CD" proteins, such as CD52, CD47, CD30, CD33, CD20, CD152 and CD279; growth factors such as vascular endothelial growth factor (VEGF); growth factor receptors such as epidermal growth factor receptor (EGFR) or human epidermal growth factor receptor 2 (HER2).

Several antibodies that bind to such antigens or targets are known and have been approved for the treatment of cancer, and any of these antibodies may be used conjunction with the agents of the present invention. Preferred antibodies are those that have utility in treating solid tumours, and especially those with an altered ECM, such as breast, ovarian and pancreatic cancers, and any of the antibodies described above may be used in conjunction with the immunotherapeutic agents and compositions of the present invention.

In addition to the therapeutic agents of the present invention, a therapeutic composition may comprise any pharmaceutically acceptable diluent, carrier or excipient. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, pH, temperature etc.

Pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Dosages of the therapeutic agents may also be determined in routine manner according to standard clinical practice. Doses of 0.1-10 mg/kg, such as doses of 0.1-0.5 mg/kg, 0.1-1 mg/kg, 0.1-2 mg/kg, 0.1-5 mg/kg, 0.5-1 mg/kg, 0.5-2 mg/kg, 0.5-5 mg/kg, 0.5-10 mg/kg, 1-2 mg/kg, 1-5 mg/kg, 1-10 mg/kg, 2-5 mg/kg, 2-10 mg/kg or 5-10 mg/kg may be administered daily, weekly, or every 10 days, 2 weeks, 3 weeks or monthly until disease progression, or until unacceptable toxicity is observed.

Likewise the pharmaceutical compositions or therapeutic agents may be administered in any convenient or desired manner, e.g. parenterally or non-parenterally, for example by enteral administration, e.g. orally (depending on the nature and/or formulation of the agent), or by intravenous, subcutaneous, intramuscular, intraperitoneal injection or infusion. The administration may be systemic or local, depending e.g. on the condition to be treated, the nature of the agent and/or formulation etc. Thus, for example the agent may be delivered locally e.g. by infusion or direct injection, e.g. to the site or location of a cancer.

High levels of CLPTM1 expression on particular cells or in particular tissues of a patient may indicate that a particular patient may be responsive to a therapy which targets cells expressing CLPTM1 for elimination. CLPTM1 may therefore be detected at the surface of cells, and such detection may indicate that a subject might benefit from treatment with any of the therapeutic agents of the present invention. The detection of CLPTM1 may be used to determine whether a subject may in need of therapy according to the present invention. In particular, the method may identify a cancer-suffering subject who may benefit from therapy with a therapeutic agent capable of binding to CLPTM1 at the surface of an immune cell and modulating the activity of the immune cell, said method comprising detection of CLPTM1 is at the surface of an immune cell. Thus, detecting the presence of CLPTM1 at the surface of an immune cell might indicate that a subject may benefit from such therapy.

Thus, in a yet further aspect, the present invention provides methods for identifying whether a patient might be responsive to a treatment comprising the elimination of cells expressing CLPTM1, comprising detecting the presence of CLPTM1 expressed at the surface of an immune cell. Preferably, the immune cell is an immunosuppressive immune cell, tumour-infiltrating lymphocyte, $T_{reg}$ or macrophage cell, Myeloid Derived Suppressor Cell, M2 macrophage cell, or antigen presenting cell e.g. a dendritic cell.

CLPTM1 may be detected in vivo (i.e. in a subject) or in vitro. This receptor may be detected in the body of a subject, or, preferably in a sample from a subject.

The sample may be any appropriate clinical sample from a subject, particularly a cell-containing sample, e.g. it may be a sample of tissue or body fluid, e.g. a tissue biopsy sample, blood or a blood-derived sample, urine, CSF, saliva, stool or a swab, washing or rinsate. The method of the invention thus preferably comprises providing a sample from a subject and detecting CLPTM1 in said sample.

CLPTM1 may be detected by any means known in the art for detecting a protein, preferably in methods which detect the presence of a protein at the surface of a cell. Thus, the method may be any method based on detecting expression of a protein at the surface of a cell.

Preferred methods comprise detection using an antibody capable of binding to CLPTM1. An antibody may be labelled (e.g. fluorescently, or radiolabelled, or may comprise an enzyme moiety).

Detection may comprise detection by microscopy, e.g. by dark-field (fluorescence) microscopy, or bright-field microscopy, and suitable detection labels for various microscopy-based detection assays are known in the art. Other detection means, including immunoassays such as enzyme-linked immunoassay (ELISA), radioimmunoassay (RIA) or immuno-PCR may also be used.

The detection may comprise a proximity assay-based detection method, an in particular a proximity assay based on using antibody-based binding partners for CLPTM1. Proximity assays are well-known in the art, and are widely described in the literature. Proximity assays based on pairs (or more) of proximity probes each comprising a binding partner capable of binding directly or indirectly to an analyte (e.g. via an intermediate analyte-binding antibody or other binding partner for the analyte) and a nucleic acid domain which interacts with the nucleic acid domain of the other proximity probe(s) to generate a detectable signal when the probes have been bound in proximity (e.g. when the partners of an interacting pair have interacted or bound together) have been developed and commercialised by Olink AB of Uppsala, Sweden. The interaction between the nucleic acid domains of proximity probes may comprise a nucleic acid ligation and/or extension reaction and may be detected by detecting a ligation and/or extension product. The nucleic acid domains themselves may interact (e.g. may be ligated together), or they may template the formation of a ligation and/or extension product from one or more added oligonucleotides. Particular mention may be made of an in situ proximity ligation assay (PLA) which may be used to detect an interaction in situ in a cell or tissue sample. Such an assay has been developed by Olink AB and is marketed under the Duolink® brand name. Proximity assay are described in U.S. Pat. Nos. 6,878,515, 7,306,904, WO5 2007/107743, WO/EP2012/051474 and WO2012/152942.

In an additional aspect of the present invention it is possible to monitor the treatment of subject having cancer who has been treated with a therapeutic agent capable of stimulating antigen presenting immune cells as described above. As these therapies comprise the stimulation of an antigen presenting immune cell, which in turn activates an anti-cancer immune response, detection of markers for immune activation may provide an indication of the progression of treatment. Indeed, a correlation between tumour size following treatment, and levels of certain chemokines in the plasma of subjects subjected to such therapies has been identified. Example 8 describes a strong inverse correlation between the size of B16 mouse melanoma tumour treated with an anti-CLPTM1 antibody conjugated to the tubulin inhibitor DM1, and the level of various chemokines detected in blood extracted from mice which were the subject of the experiment. Without wishing to be bound by theory, it is believed that higher levels of these chemokines may indicate a greater degree of immune activation and thus a greater anti-cancer immune response.

The present invention therefore provides a method of monitoring the treatment of a subject who has been treated with a therapeutic agent of the invention, wherein said therapeutic agent is capable of stimulating an antigen-presenting immune cell and acts to stimulate antigen-presenting immune cells in the subject to activate an immune response, said method comprising detecting in a sample from said subject a chemokine selected from CCL2, CCL3, CCL5 and CXCL9. In preferred embodiments, the method may comprise detecting any two or more of said chemokines in any combination.

Preferably, the chemokine or chemokines may be detected in blood (i.e. whole blood) or in a blood fraction, for example plasma, serum. Detection may take place according to any convenient method known in the art.

The present invention may be better understood through the following Examples and Figures, in which:

FIG. 1 shows that CD14+ immune cells express CLPTM1 at their surface. CD14+ monocytes from peripheral blood were stained for CLPTM1. Dotted line—negative FMO control. Middle peak—Extra-cellular CLPTM1 staining. Right hand peak—Total (extra-cellular & intracellular CLPTM1 staining).

FIG. 2 shows that CLPTM1 is at the surface of CD14+ macrophages with low levels of MHC2.

FIG. 3 shows that T-cells with low levels of TMEM173 expression express CLPTM1 at their cell surface. CD45+; CD19-; CD3+ tumour infiltrating lymphocytes were analysed.

FIG. 8 shows the expression of CLPTM1 at the cell surface for various cells of the immune system and in tumour cells isolated from the following mouse cancer model: 4T1 (breast), B16 (melanoma), CT26 (colon) and LLC (lung), and from healthy spleen tissue. High levels of expression are observed in various cells of the immune system isolated from the different tumour microenvironments.

Figure 9:
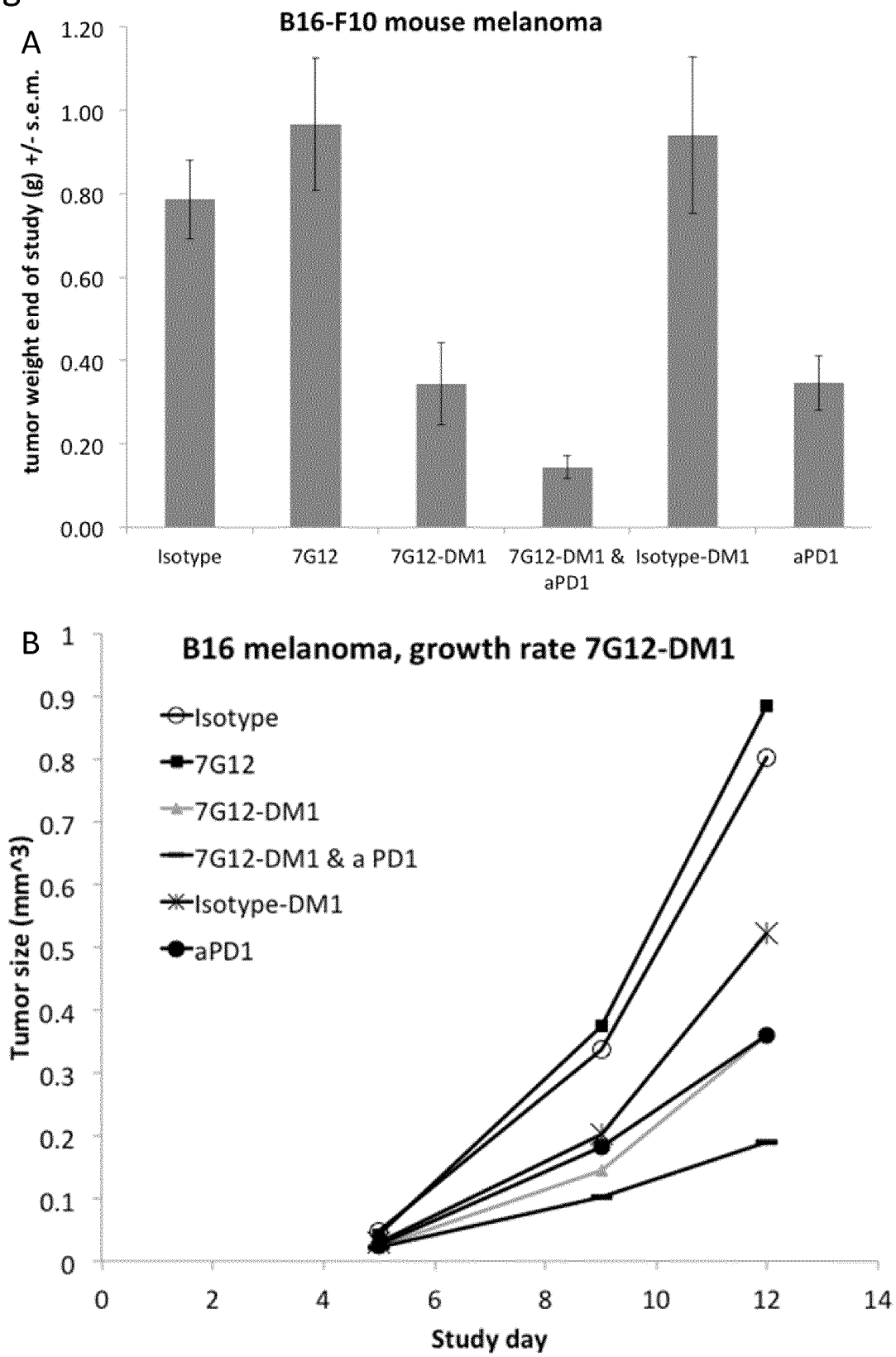

FIG. 9 shows the effect of an anti-CLPTM1 antibody (7G12) conjugated to DM1 (ADC) on tumour growth in a B16 mouse melanoma model. A) Tumour weight (g) at end of study. B) Tumour size ($mm^3$) over time. The ADC reduces tumour growth to a similar extent to an anti-PD1 antibody (aPD1), compared to isotype controls and the 7G12 antibody alone, and the combined therapy of the ADC and aPD1 results in a greater reduction in tumour growth than either treatment in isolation.

Figure 10:
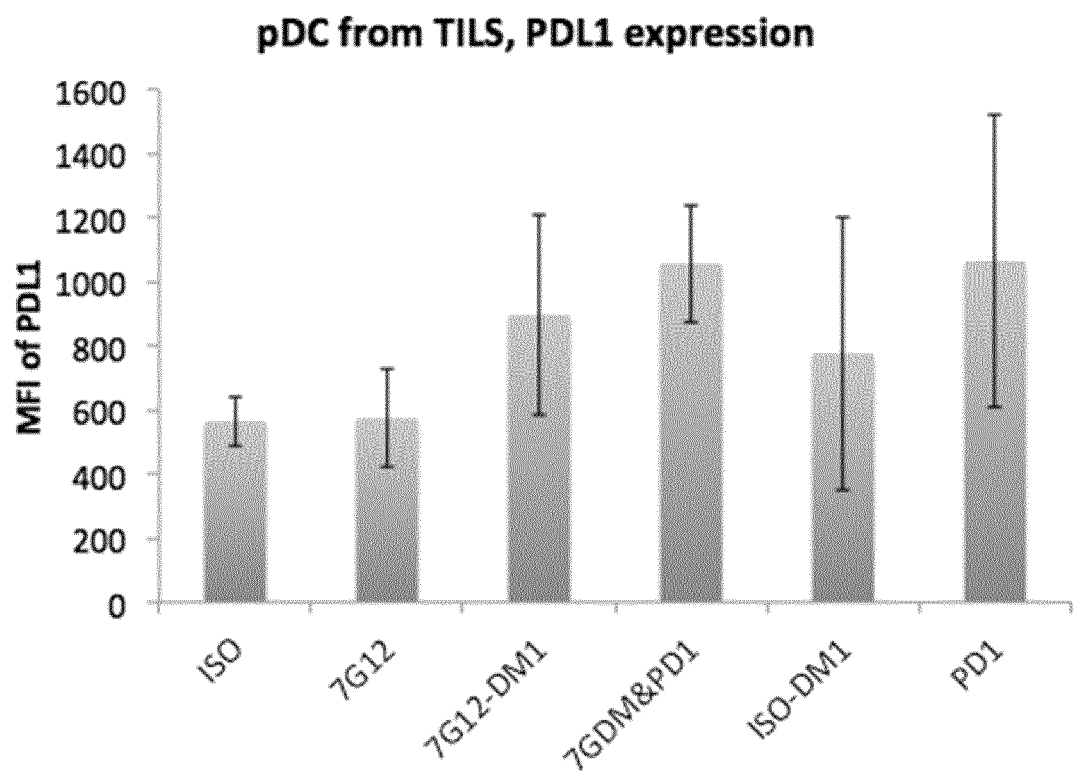

FIG. 10 shows the expression of PDL1 at the cell surface in pDC cells isolated from tumour infiltrating lymphocytes (TILs). PDL1 expression is a marker of immune activation. The anti-CLPTM1 antibody (7G12) conjugated to DM1 (ACD) induces a higher level of PDL1 expression than either an isotype control or the 7G12 antibody alone. The combination of the ADC and an anti-PD1 antibody causes a significant increase in PDL1 expression at the cell surface relative to the isotype control and 7G12 antibody alone.

Figure 11:
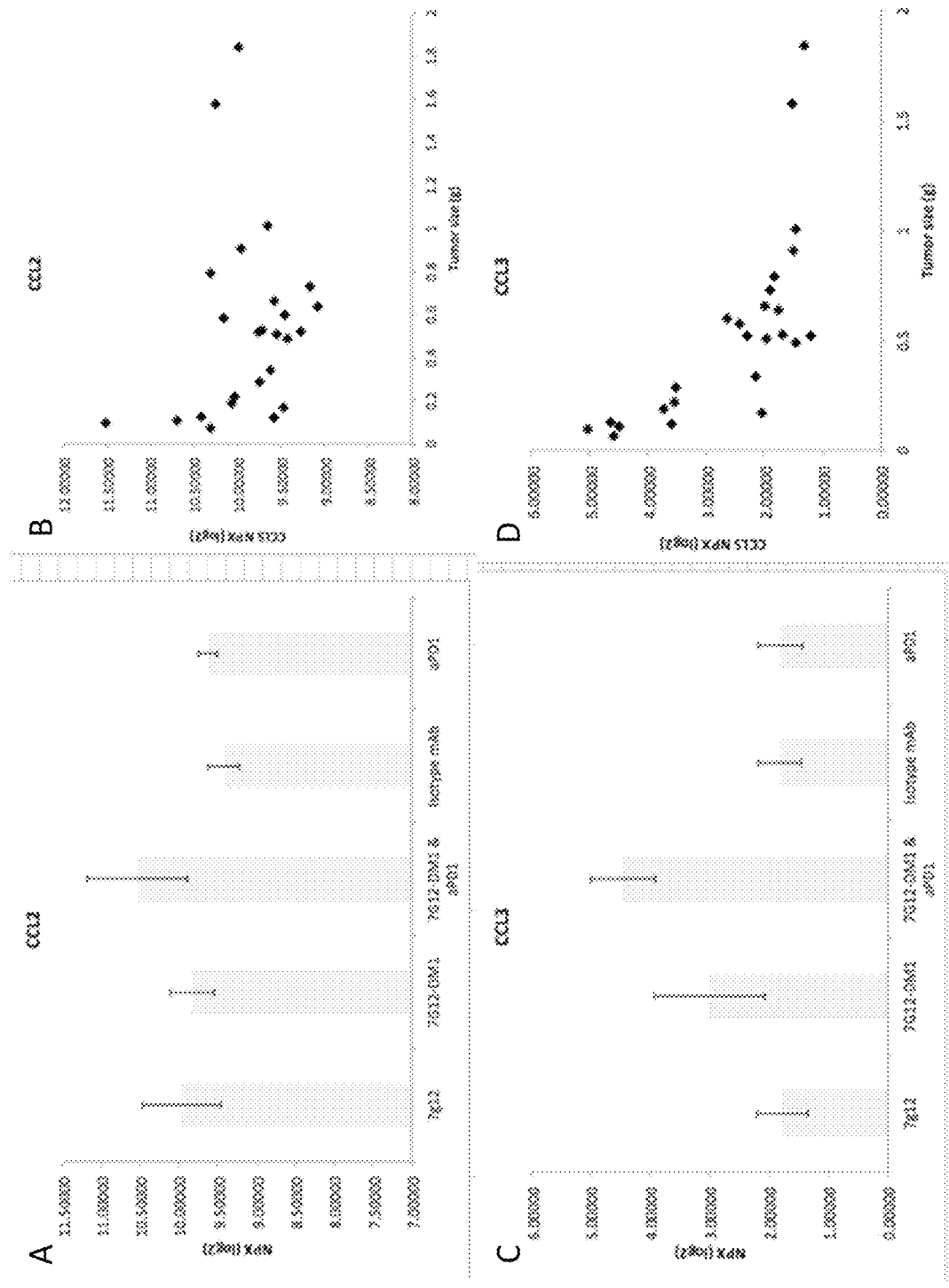
Figure 11:
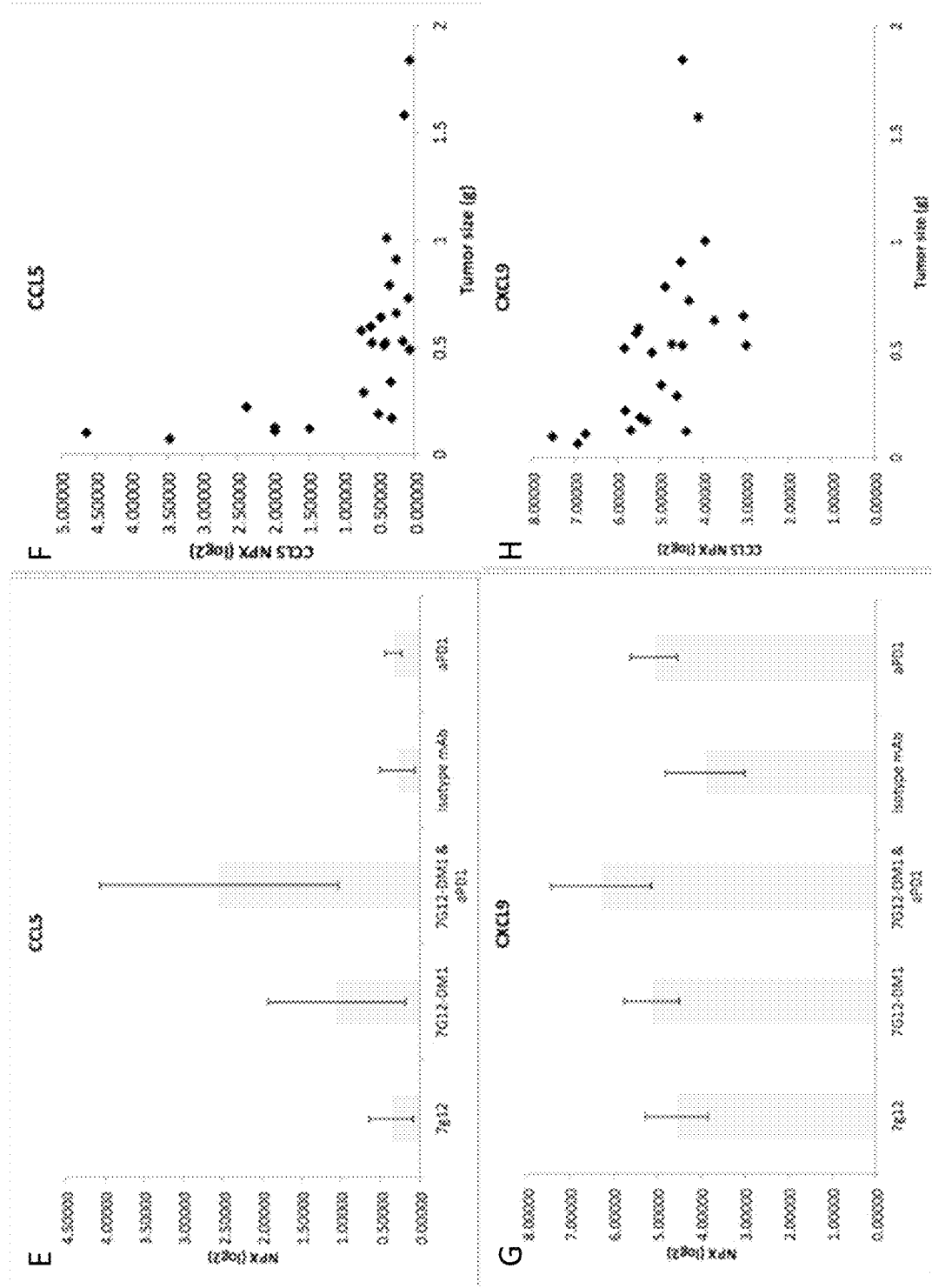
Figure 11:
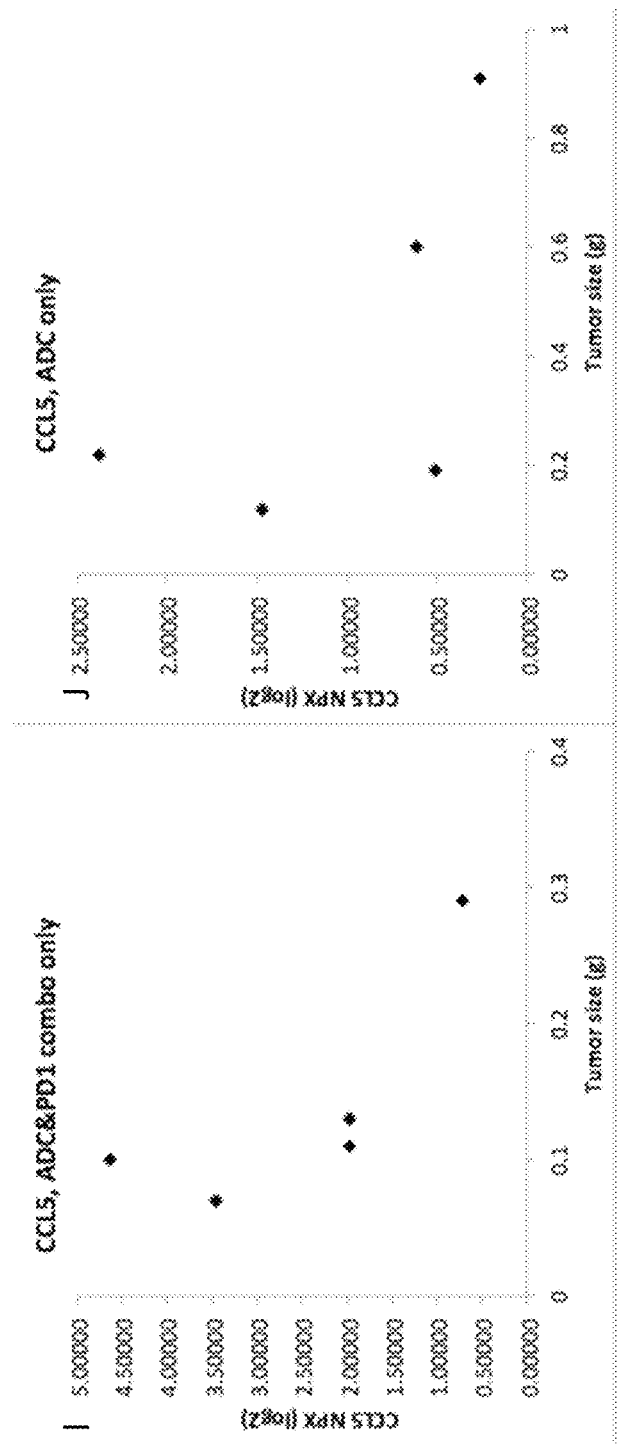

FIG. 11 shows the induction of cytokine expression, and the correlation between levels of cytokines and tumour size in serum isolated from the mice in the Example 6 study. A), C), E) and G) levels of CCL2. CCL3. CCL5 and CXCL9 in response to different treatments. The ADC and aPD1 combination were found to increase all of the tested cytokines above the control level. B). D). F) and H) levels of CCL2, CCL3, CCL5 and CXCL9 correlated to tumour size (g). Higher levels of the cytokines are linked to smaller tumour size. I), J) levels of CCL5 in response to ADC and aPD1 combination treatment and ADC only. Higher levels of the cytokine are linked to small tumour size. Together, these data demonstrate immune activation against cancers.

Figure 12:
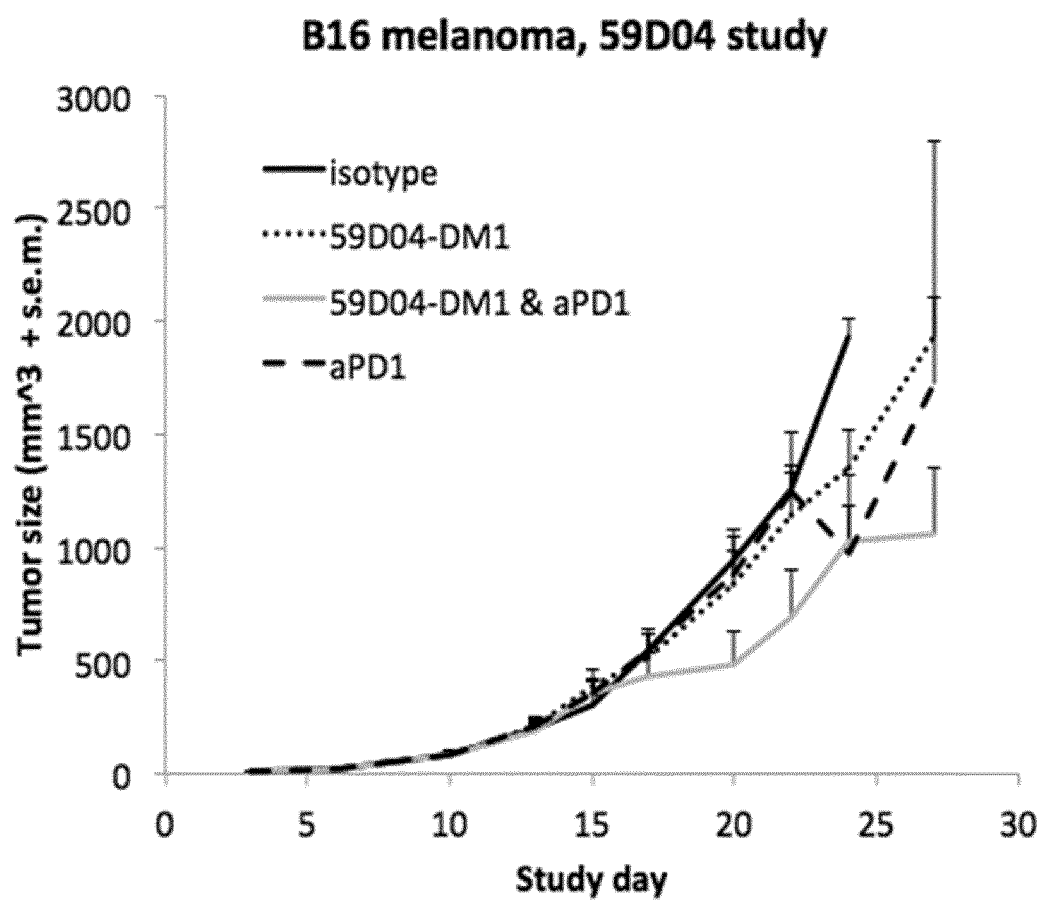

FIG. 12 shows the effect of an anti-CLPTM1 antibody (59D04) conjugated to DM1 (ADC) on tumour growth in a B16 mouse melanoma model. The ADC and aPD1 combination treatment resulted in reduced tumour growth relative to the ADC or aPD1 alone, and relative to an isotype control.

Figure 13:
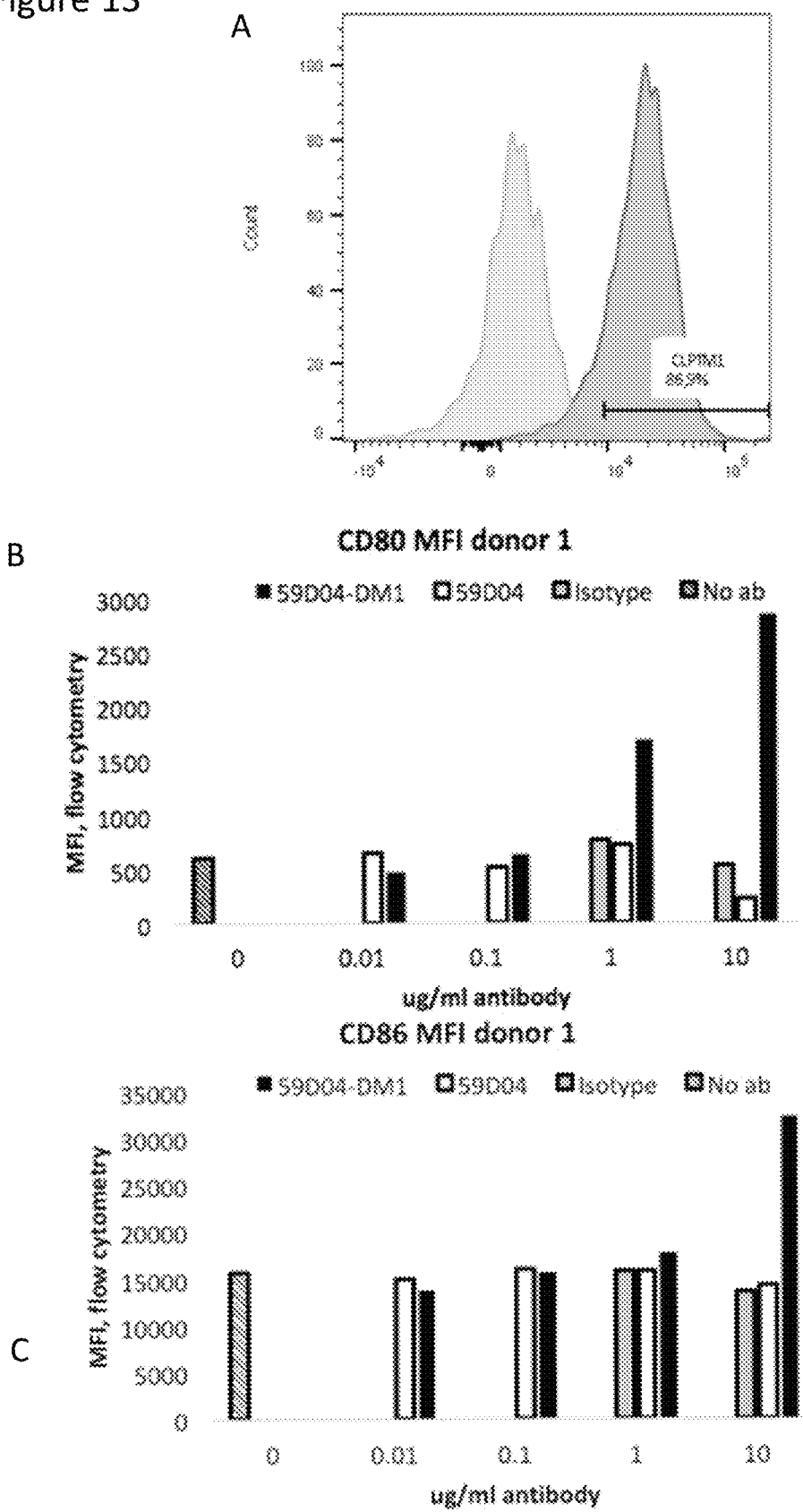

FIG. 13 shows the expression of CLPTM1 at the cell surface in M2 macrophages and activation of macrophages by the 59D04 antibody conjugated to DM1 (ADC). A) Cell surface expression of CLPTM1 measured by flow cytometry. B), C) expression of CD80 and CD86 on the cell surface in a dilution series of the ADC. Both CD80 and CD86 were stimulated by the ACD, relative to the 59D04 antibody alone or an isotype control.

Figure 14:
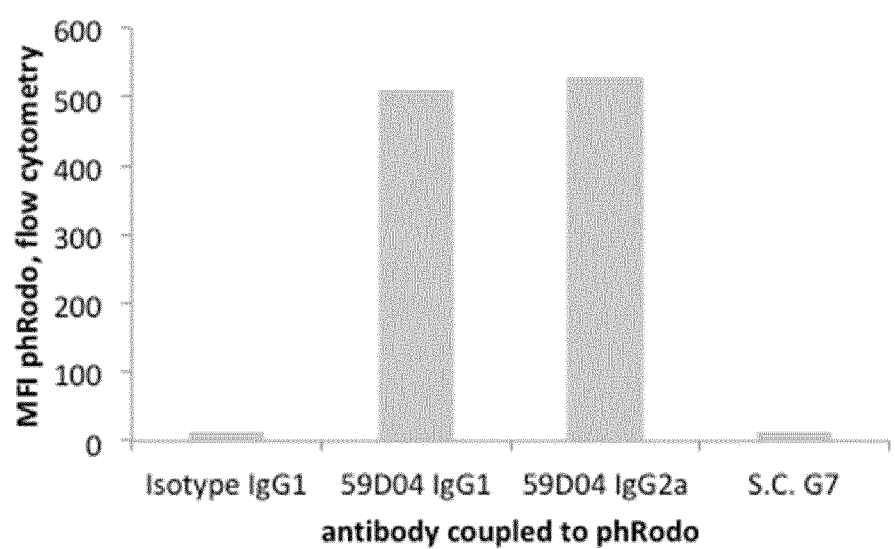

FIG. 14 shows internalisation of the 59D04 antibody conjugated to phRhodo. Both IgG1 and IgG2a isotype antibodies show a high level of internalisation. Isotype control and the "Santa Cruz" anti-CLPTM1 antibody show very low levels of internalisation.

Figure 15:
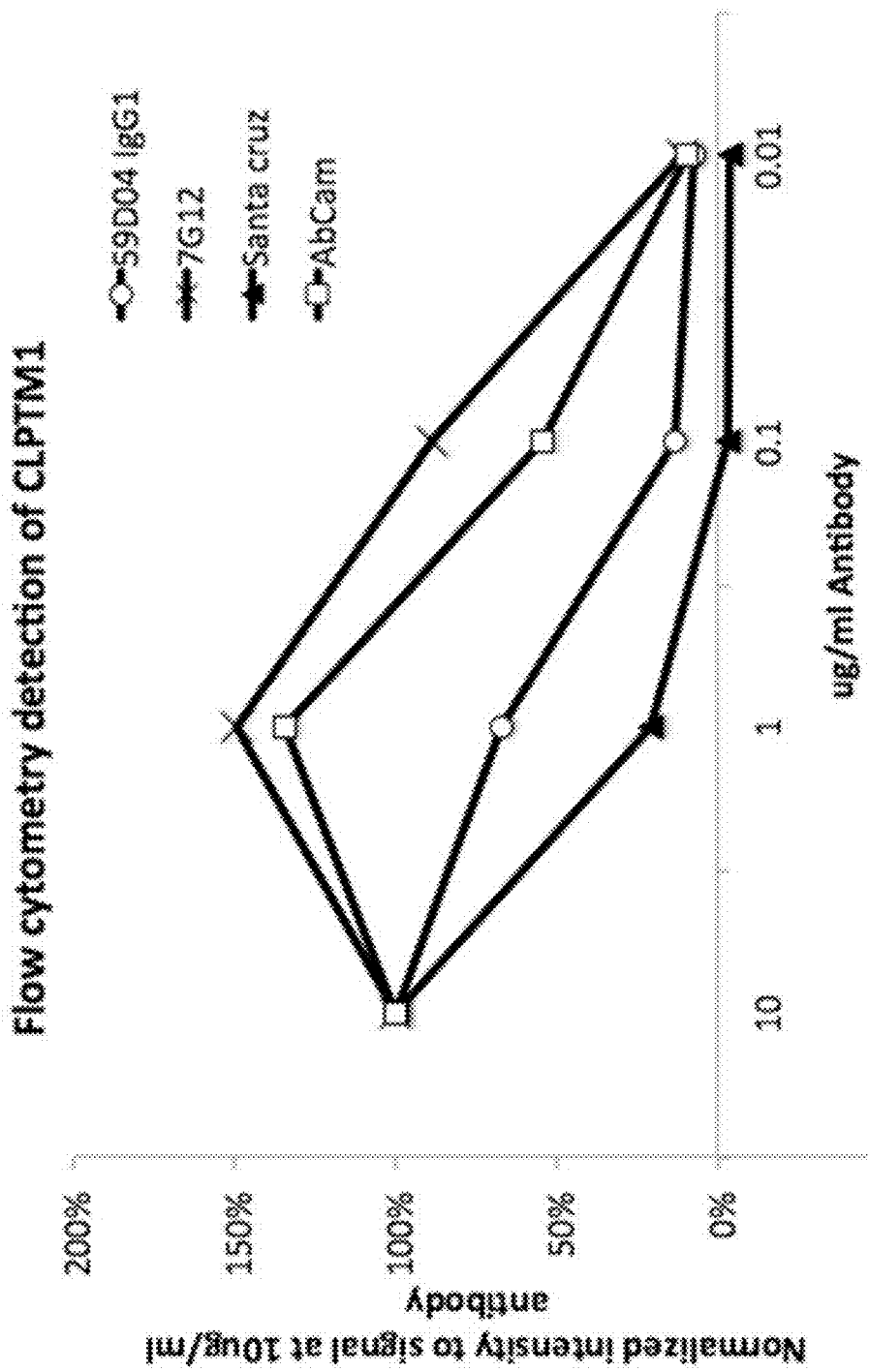

FIG. 15 shows the measurement of the affinity of the 59D04, 7G12, Santa Cruz and AbCam antibodies by flow cytometry. CLPTM1 binding in permeabilised 0-876 cells expressing native CLPTM1 was measured in a 10× dilution series. The highest affinity antibody measured was 7G12, which retained greater than 50% of its maximum binding at 0.1 μg/ml. The AbCam antibody also retained greater than 50% of its maximum binding at 0.1 μg/ml. The 59D04 antibody retained greater than 50% of its maximum binding at 1 μg/ml, whilst the Santa Cruz antibody had less than 50% of its maximum binding at this level.

Figure 16:
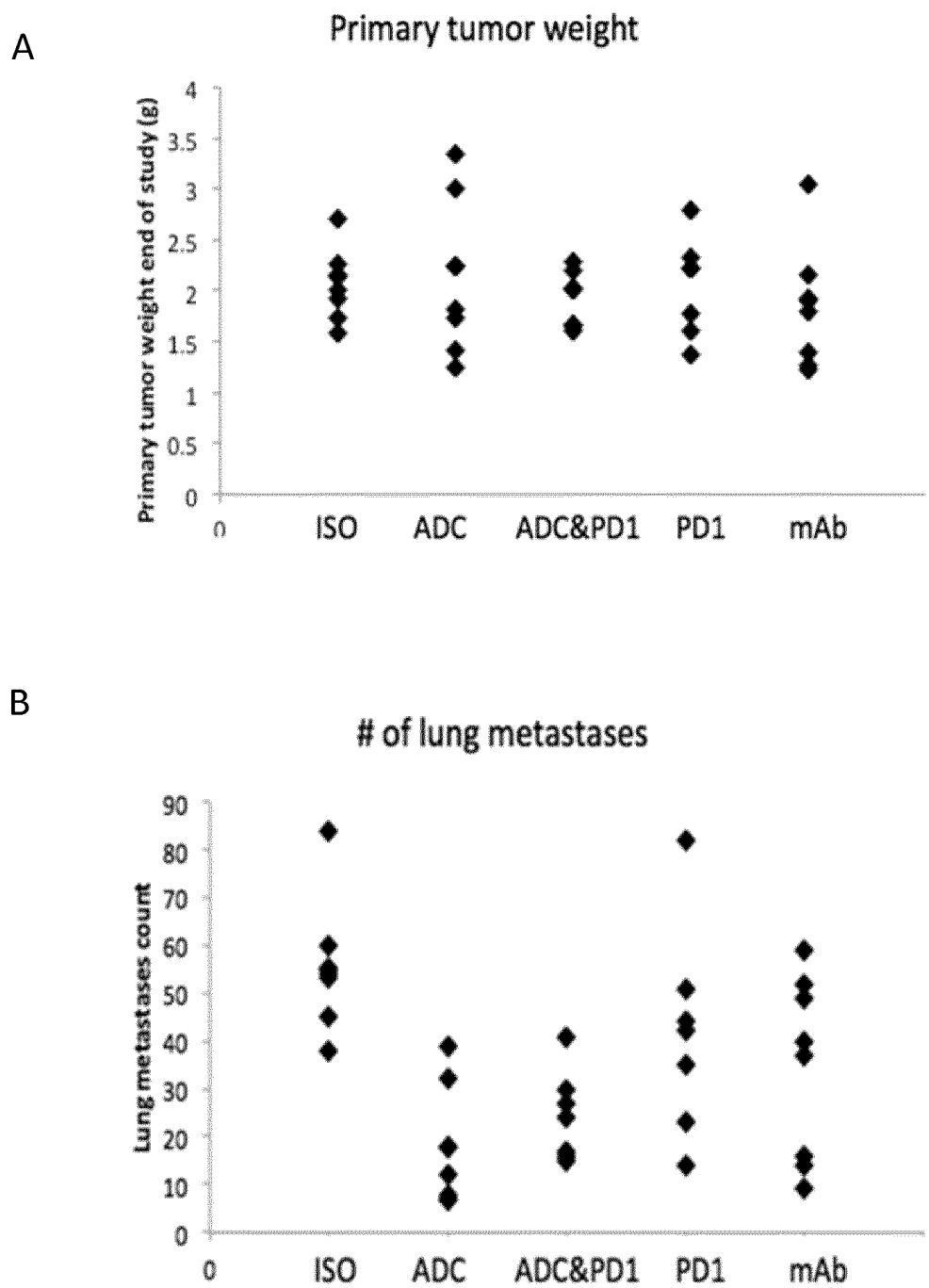

FIG. 16 shows the effect of an anti-CLPTM1 antibody (59D04) as an IgG2A antibody or as a conjugate with DM1 (59D04-DM1) alone or in combination with an anti-PD1 antibody (aPD1), compared to aPD1 or an isotype control on the syngeneic orthotopic breast cancer model 4T1 in mouse. A) Primary tumour weight (g) at end of study. B) Number of lung metastases. Whilst there was no statistically significant change in primary tumour size, the number of metastases was affected both by the 59D04 IgG2A antibody and the 59D04-DM1 conjugate, compared to isotype antibody control.

EXAMPLES

Example 1—Expression of CLPTM1 on Immune Cells

Materials and Methods
Cell Isolation, Selection and Culture

The cell suspension of heparinized peripheral blood was diluted 1:1 and placed on a Ficoll Paque Plus, after which the suspension was centrifuged at 400×g for 30 minutes. The PMBC layer was transferred to 50 mL tube of PBS and centrifuged for 7 min at 250×G. CD14+ cells were isolated using EasySep Positive Selection kit CD14 (Stemcell inc) according to the manufacturer's instructions. Cell culture was performed in 48 well cell culture plates which were seeded with cell suspension at a $0.833 \times 10^6$ cells/mL in RPMI medium and 300 uL added to each well. CD14+ cells were allowed to adhere for 90 minutes at 37° C. in an incubator and non-adherent cells were removed.

Derivation of M1, M2 and Dendritic Cells (DC) from CD14+ Monocytes

PBMCs from buffy coat of healthy blood donor were obtained and CD14 positive cells were isolated and plated in 0.5 ml 1640 RPMI, $1 \times 10^{\hat{ }}6$ cells/ml. For M2 macrophage derivation, 50 ng/ml M-CSF was added. For M1 derivation 50 ng/ml GM-CSF was added. For DC derivation 50 ng/ml GM-CSF+20 ng/ml IL-4 was added, and 3 days before harvest 20 ng/ml TNFα. All cells were harvested after 7 day total culture. Medium and cytokines were changed every 2-3 days. M1 and M2 differentiation cultures were in a separate reaction also given 20 μg/ml of the 7G12 anti-CLPTM1 antibody 24 hours before harvest and flow cytometry analysis. All cytokines purchased from RnD Systems.

Flow Cytometry

Figure 1:
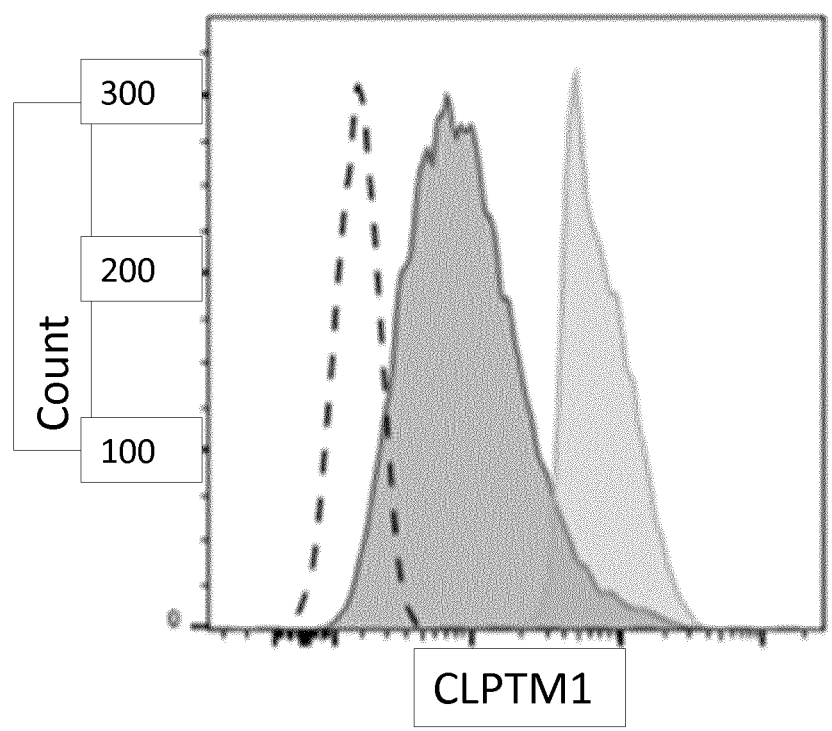
Figure 2:
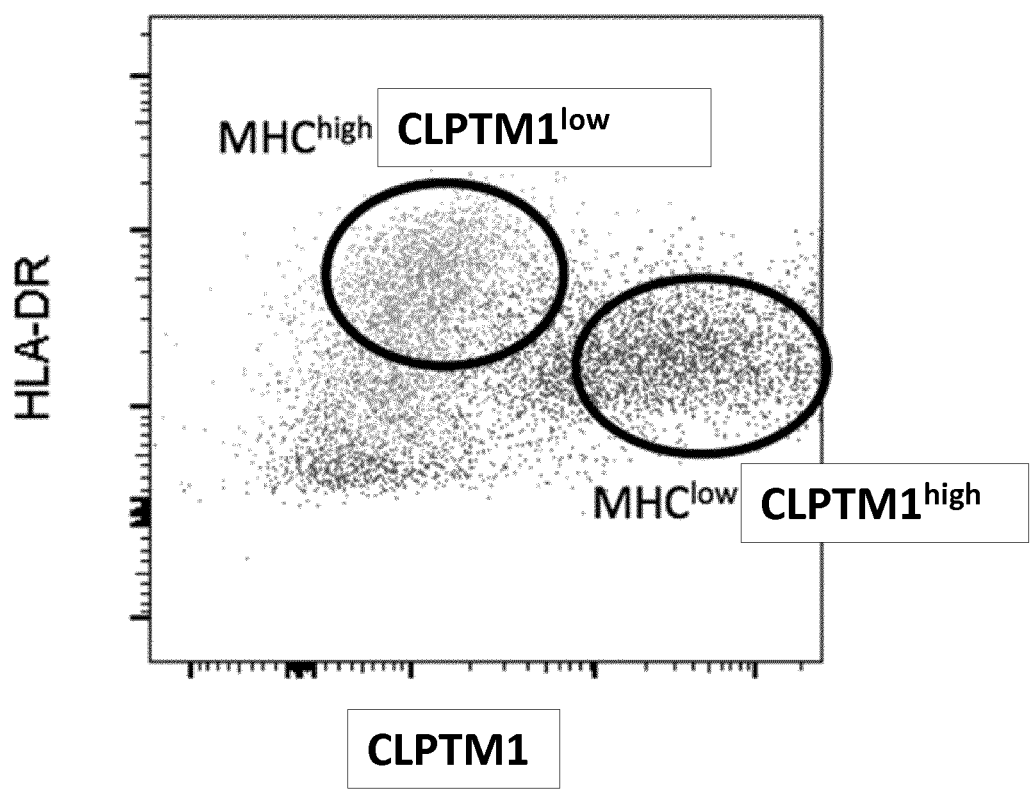
Figure 3:
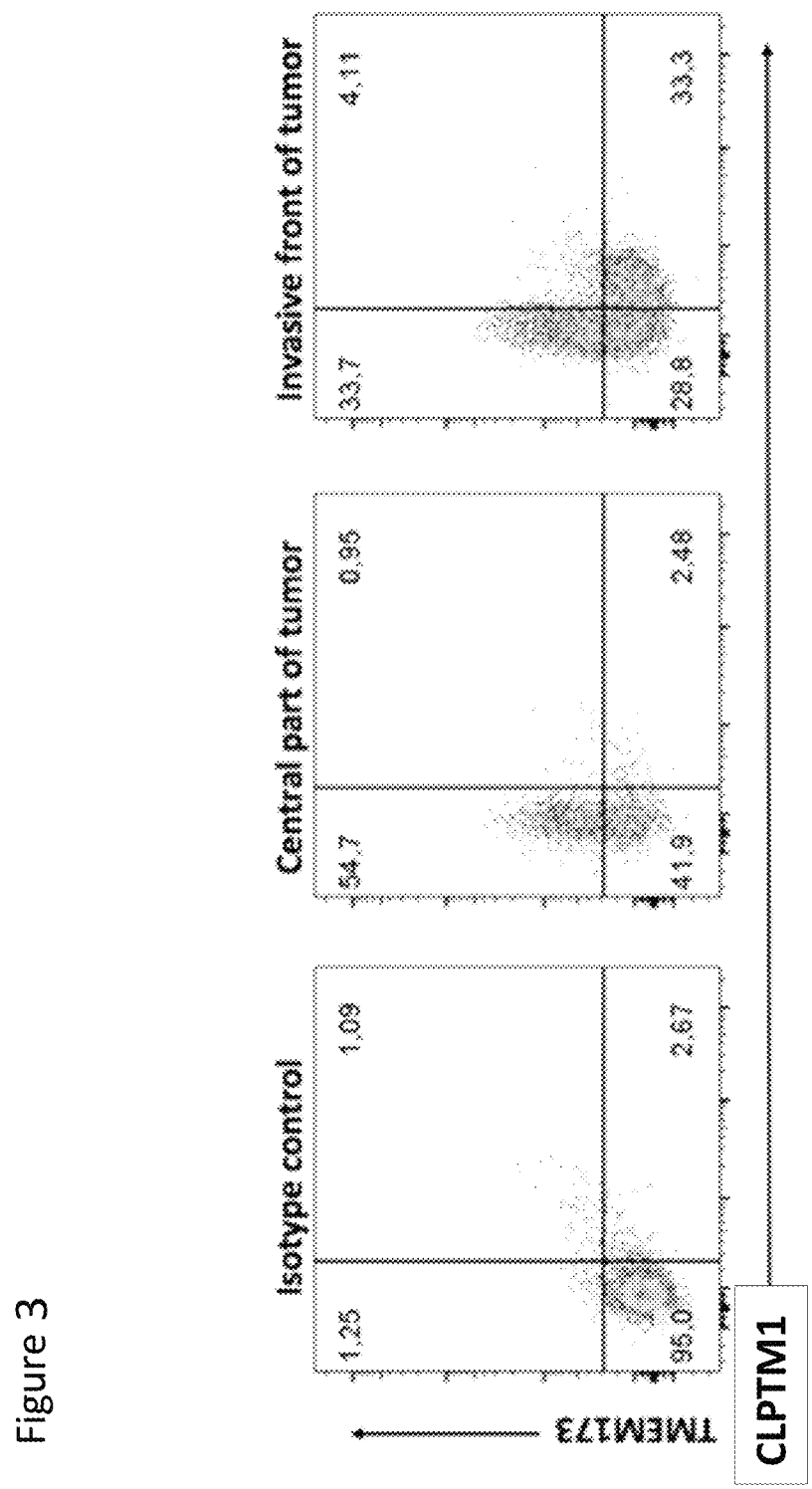
Figure 4:
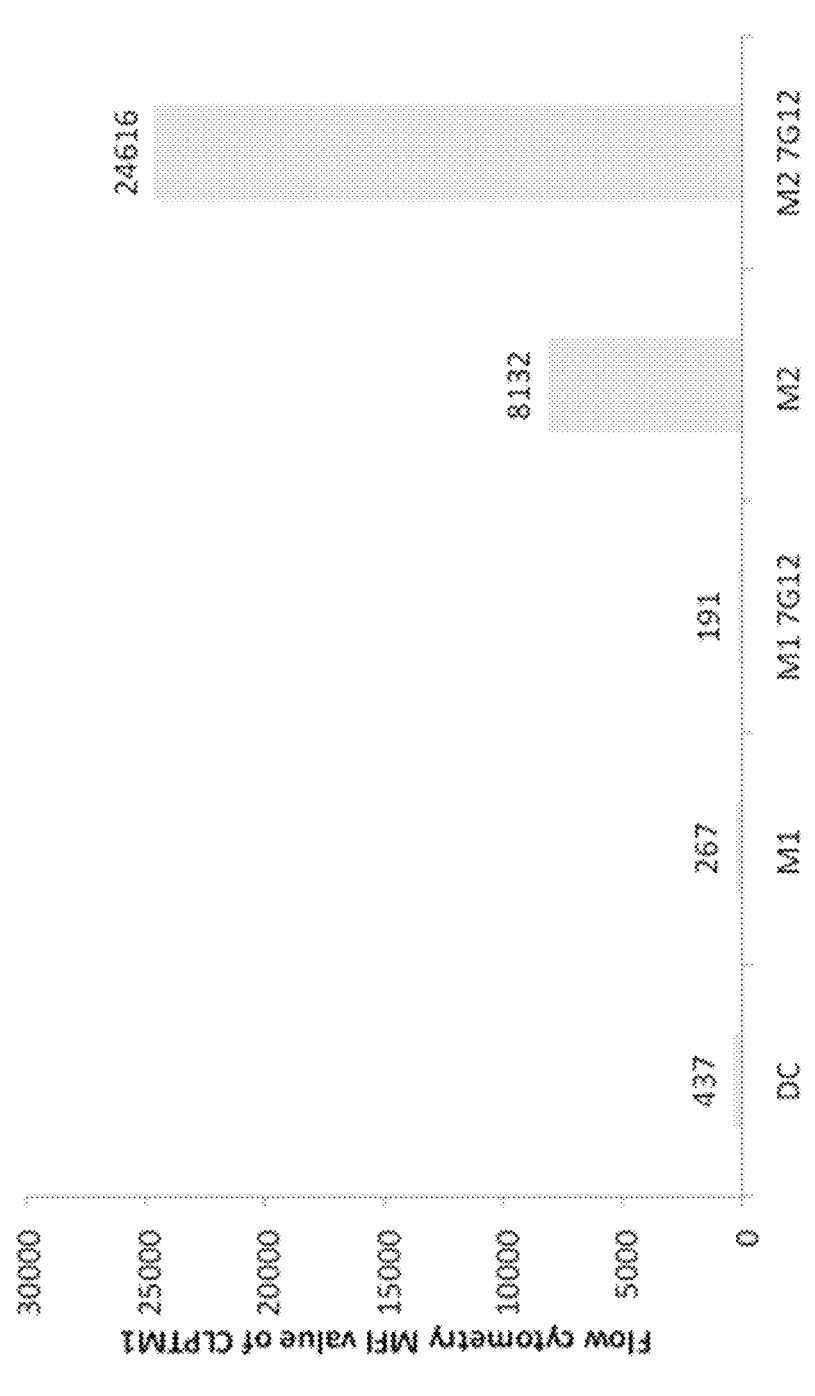
FIG. 4 shows that M2 macrophages, but not dendritic cells or M1 macrophages, express high levels of CLPTM1.

The amount of surface expression of CLPTM1 was analyzed by flow cytometry using the 3A10-PE antibody. 3A10 mouse monoclonal antibody was conjugated to phycoerythrin using Lightning link kit from Innova Biosciences. FIG. 4 shows that CLPTM1 surface expression more than 100× higher on M2 macrophages illustrating the applicability of this receptor as a suitable drug target for cell elimination by various means in cancer. Addition of the 7G12 antibody further increased the CLPTM1 surface expression but only on the M2 macrophages and did not increase CLPTM1 on the surface of M1 macrophages.

Example 2—ADCP Assay

Materials and Methods

Mouse monoclonal antibodies were developed by immunization with synthetic peptides using Rapid-Prime™ method by ImmunoPrecise (Victoria, Canada). The following peptide sequences where used giving rise to corresponding antibody clones: PWNFLGDELYEQSDE (SEQ ID NO: 48) (3A10, 7G12), DEEQDSVKVALLET (SEQ ID NO: 49) (2D12), TEADPEMIKRAEDY-C(SEQ ID NO: 51) (5H8, 10F4, 6E4), C-GDYYPIIYFNDYW (SEQ ID NO: 53) (1G10, 3G11, 10F3, 6A1), C-RNLFPKDTLMNLH (SEQ ID NO: 55) (9E3). The "-C" or "C-" in SEQ ID NOs: 51, 53 and 55 indicates that a cysteine (C) residue has been added to the native sequence for conjugation purposes, and is not part of the natural amino acid sequence. (The corresponding native sequences are shown in SEQ ID NOs: 50, 52 and 54 respectively).

J774 cells were stained with either CellTrace Violet (ThermoFisher C34557) or CellTrace Green (ThermoFisher C34554) according to the manufacturer's instructions. Cell cultures containing 50% of each labelled cell where grown overnight with 20 ug/ml of each monoclonal antibody. Double positive cells were detected and scored as a percentage of total cell population using flow cytometry FACSCANTOII (Becton Dickinson).

Mouse macrophage cell line J774 with high cell surface expression of CLPTM1 was cultured. These cells where labeled with a red or violet fluorescent dye and co-cultured overnight with various CLPTM1 antibodies.

Figure 5:
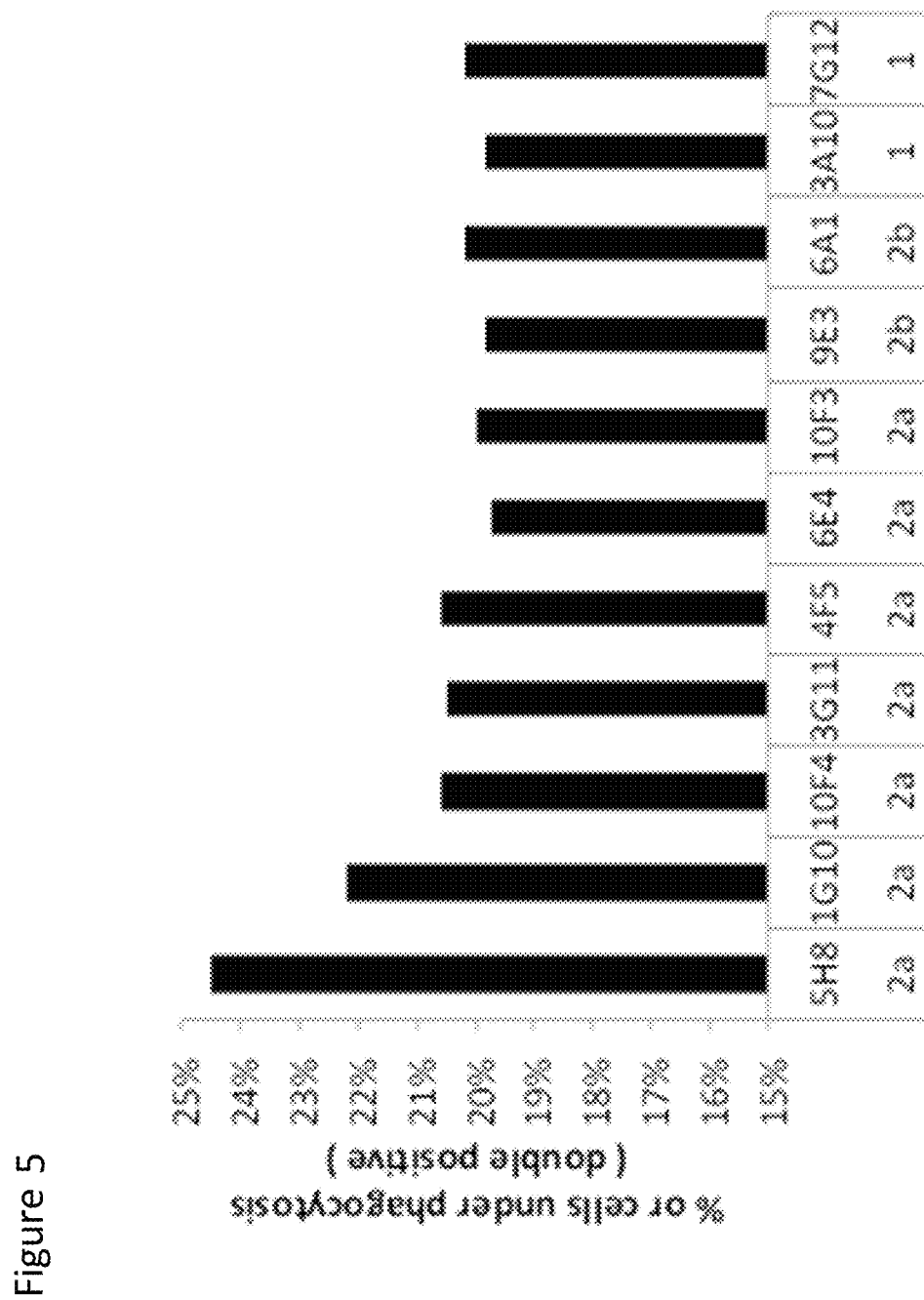
FIG. 5 shows that mouse IgG2a-type antibodies are capable of eliciting strong ADCP.

Antibody Dependent Cellular Phagocytosis (ADCP) was assessed for several mouse monoclonal antibodies binding to CLPTM1. These antibodies bind to different epitopes on CLPTM1 and have various effector functions on their Fc. Mouse macrophage cell line J774 was used due to its high expression of surface CLPTM1 as we found by flow cytometry analysis. These cells were labelled with a red or violet fluorescent dye and co-cultured overnight with various CLPTM1 antibodies. Flow cytometry analysis revealed the % of double labeled cells showing the level of phagocytosis. Only IgG2a effector functionalized mAb clones are capable of eliciting strong ADCP. Our data in FIG. 5 show that clone 5H8 and 1G10, both IgG2a-type, increase phagocytosis.

These data indicate that antibodies having immune effector function can lead to the elimination of cells expressing CLPTM1.

Example 3—Effect of Cytotoxic Drug Conjugate on Cells Expressing CLPTM1

Materials and Methods

CLPTM1 clone 7G12 (IgG1) was conjugated to Mertansine DM1 (Abcam ab146096) using an SMCC cross-linker (ThermoFisher 22360). 100 ug of antibody in 100 uL was first PBS equilibrated in a Zeba spin column (ThermoFisher 89808). Then 10 uL of SMCC in DMSO (1.76 ug/uL) was added and set at room temperature for 2 hours. Surplus SMCC was removed by a Zeba spin column then mixed with 5 uLs of Mertansine (1.3 mM dissolved in dimethylformamide). Reaction was set overnight at room temperature then excess mertansine removed by Zeba spin column 7kMW-cut off.

Figure 6:
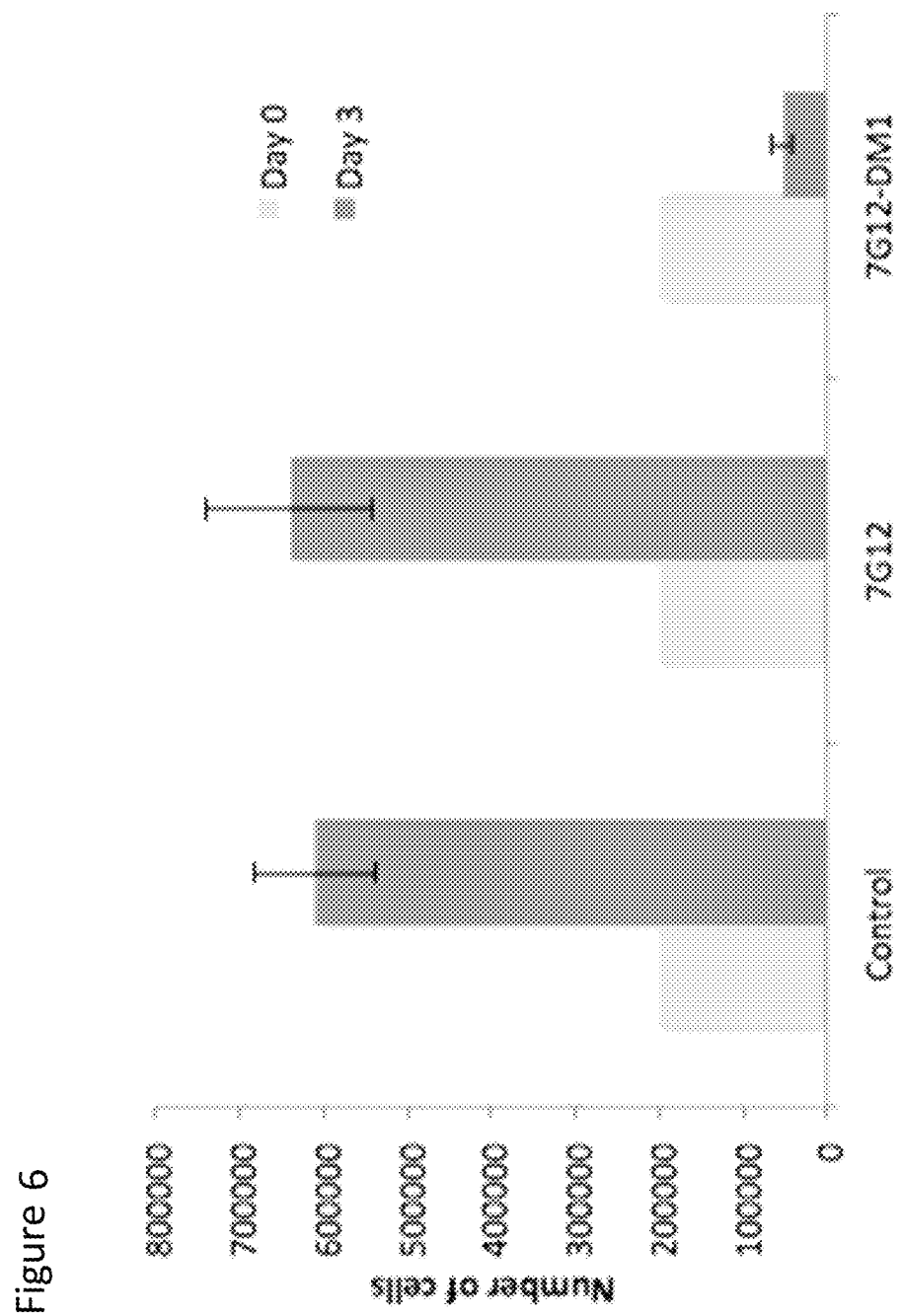
FIG. 6 shows that an antibody conjugated to a cytotoxic drug are effective at eliminating cells expressing CLPTM1 at their cell surface.

Cultures of 200,000 seeded mouse macrophage cells J774 with verified high levels of CLPTM1 expression were prepared. A control was prepared, in which no antibody was added to the culture. A negative control sample in which the unconjugated 7G12 antibody was used. 7G12 antibody conjugated to Mertansine was added to a test sample. Cells were seeded on Day 0, and grown for three days. After three days, manual counting was performed to establish cell numbers. The number of cells present in each condition is shown in FIG. 6.

After three days' culture, the test sample to which Mertansine-conjugated antibody had been added demonstrated a large decrease in the number of cells present. By contrast, both the control and the negative control samples showed high levels of cell growth following three days' culture.

This demonstrates that cytotoxic drug conjugates to antibodies are effective at eliminating cells expressing CLPTM1 at their cell surface.

Example 4—Epitope Mapping of 'Bioss' pAb on CLPTM1

Materials and Methods
Peptide Array

The N-terminal aa 1-354 aa of CLPTM1 was divided with complete coverage into 86 unique 15-mers with 11 aa overlap, produced by JPT peptide Technologies GmbH. The Bioss 8018R polyclonal antibody was incubated at 1 µg/ml o/n at +4 C, washed extensively in PBST followed by 1 hour incubation at room temperature with Alexa flour 647 (Thermo scientific) Rabbit IgG (H+L) Polyclonal Secondary Antibody (Catalog #: A-21244) diluted 1:60000 and after repeated PBST wash detected using a G2502 Microarray scanner (Agilent Technologies). The polypeptides used are shown in FIG. 7.

The epitope 1 for Bioss BS8018R has the highest Median fluorescence intensity (MFI) (signal intensity) on array, demonstrating highest binding affinity for this site.

Figure 7A:
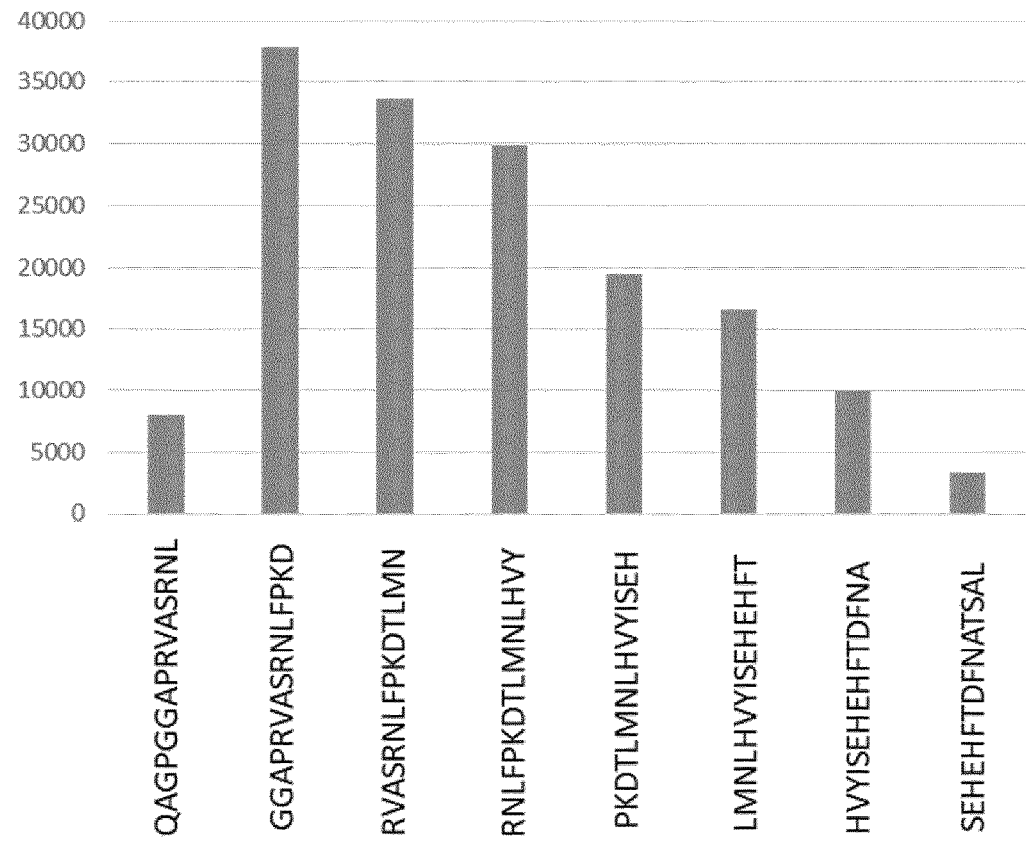
FIG. 7 shows combined results of a peptide screen to identify residues within the extracellular domain of CLPTM1 that are required for binding to GDF15 measuring binding on a peptide array. The results of binding of GDF15 to immobilised peptides are shown.

Binding of the antibody to the various peptides in the array is shown in FIG. 7A.

Minimal common denominator: PKD (SEQ ID NO: 8)

Most likely flanking amino acids also participate within the region: GGAPRVASRNLFPKDTLMNLHVYISEH (SEQ ID NO: 56).

Figure 7B:
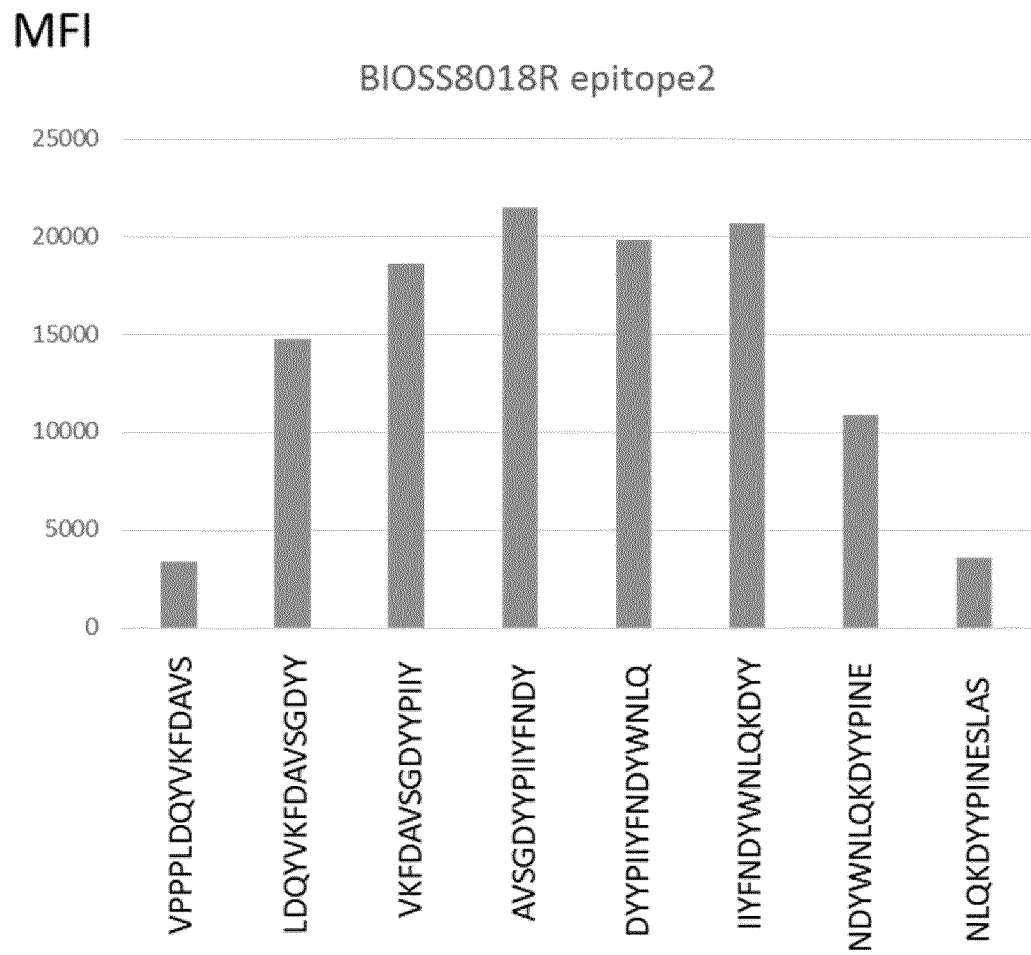

The epitope 2 displayed a slightly lower MFI, yet suggest a second site with affinity for this antibody. Binding of the antibody to the various peptides in the array is shown in FIG. 7B. The region for epitope 2 is within: LDQYVKF-DAVSGDYYPIIYFNDYWNLQKDYYPINE (SEQ ID NO: 57).

Example 5—CLPTM1 Expression Levels on Various Immune Cells and Cancer Cells

Four syngeneic mouse models of cancer were analyzed as of tumor infiltrating leucocytes and expression of CLPTM1. Data is illustrated in FIG. 8 as percentage of positive cells over isotype control and Mean Fluorescence Intensity (MFI) in comparison to immune cells isolated from healthy mouse spleen. The data show expression of CLPTM1 on various immune cells and the tumor cells themselves but no expression on immune cells from healthy spleen. Data was acquired by standard flow cytometry protocol using antibodies from Biolegend and Beckton-Dickinson on a FACS Fortessa instrument.

Especially antigen presenting cells such as dendritic cells and macrophages show high surface expression of CLPTM1 as well as myeloid derived suppressor cells (MDSCs).

Example 6—B16-F10 Tumor Growth Data 7G12-DM1

Antigen-Drug Conjugate (ADC) Preparation

DM1-antibody conjugates were prepared as previously described in Example 3 but using a PEG4 linker in the SMCC (Pierce, ThermoFisher) in order to improve water solubility of the conjugate and scaled up to 20 mg of antibody, either 7G12 or a mouse IgG1 isotype control (BioXcell). A drug antibody ratio of 7.3 was achieved with for the 7G12-DM1 conjugate as analyzed by spectrophotometry at OD 252 and OD 280 using extinction coefficients 28044 and 5700 for DM1 at A252 and A280 respectively (M^-1 cm^-1) and 87360 and 224000 at A252 and A280 respectively for the antibody (NanoDrop). The isotype control showed DAR of 1.8. ADCs were stored at +4C in sterile conditions.

In Vivo Models

An in vivo effect study of the 7G12-DM1 ADC was performed using B16-F10 melanoma in mice (Adlego, Stockholm Sweden). 6 Study groups 1) Isotype IgG1 (MOPC21, BioXcell), 2) 7G12, 3) 7G12-DM1, 4) 7G12-DM1 & anti-PD1, 5) Isotype-DM1, 6) anti-PD1 (RPM1-14, BioXcell). Group 1 had 10 animals and the other 8 in each. 150 ug of antibody was administered i.v. for each of the 4 doses, twice weekly. Tumor size was measured by calipering during the study and at termination of the study tumors where excised and weighed.

Results

Tumor Growth of B16-F10 Melanoma, 7G12-Study

At the end of the study, tumor sizes were statistically significantly smaller in weight compared to isotype control in the 7G12-DM1 group and even smaller when combined with PD1 inhibiting antibody, see FIG. 9 and Table 1.

TABLE 1

|  | tumor (g) avg | stdev | TGI (T/C) | Ttest vs. isotype p-value | Ttest vs aPD1 p-value |
|---|---|---|---|---|---|
| Isotype | 0.786 | 0.298 |  |  |  |
| 7G12 | 0.965 | 0.449 | 122% | 0.34448 |  |
| 7G12-DM1 | 0.344 | 0.277 | 44% | 0.00662 |  |
| 7G12-DM1 & aPD1 | 0.144 | 0.079 | 18% | 0.00004 | 0.01813 |
| Isotype-DM1 | 0.940 | 0.531 | 119% | 0.46396 |  |
| aPD1 | 0.346 | 0.184 | 44% | 0.00420 |  |

Example 7—Activation of Antigen-Presenting Cells by Anti-CLPTM1 Antibodies Conjugated to DM1

We have shown that dendritic cells have high CLPTM1 in the tumour microenvironment. Upon treatment with 7G12-DM1 in the B16 melanoma study in Example 6 we see an increase in PDL1 expression on plasmacytoid dendritic cells isolated from the tumour, indicating a higher level of immune activation (see FIG. 10). TILs were isolated and analysed as described in Example 5. Up-regulated PDL1 expression is an established marker for immune stimulation. This is one of the effects by which our ADC therapy is active.

Example 8-7G12-DM1 Affects Cytokine/Chemokines

The 7G12-DM1 ADC positively affects chemokines capable of attracting immune cells in vivo. Sera were collected from the animals in the B16 melanoma study in Example 6 above and analysed by an Olink Proteomics prototype mouse panel (Uppsala Sweden). The ADC showed statistically significant increases in CCL2 (monocyte and dendritic cell attractant), CCL3 (macrophage and monocyte attractant), CCL5 (T-cell attractant), and CXCL9 (T-cell attractant) (see FIG. 11). PD1 inhibition alone did not affect these chemokines but did show an additive positive effect together with the 7G12-DM1 ADC. Also, a small tumour size at study termination correlated with high levels of these chemokines. Even within a treatment group (ADC and ADC&PD1 combination), CCL5 correlates with small tumour size illustrating an immune cell based anti-tumour response of variable degree between individual animals, FIG. 11. These chemokines may be used clinically to monitor response of therapy by measuring blood levels of these proteins.

Example 9—Tumour Growth of B16-F10 Melanoma Using a Fully Human Antibody 59D04 IgG2a ADC Preparation
DM1-antibody conjugates were prepared as described in Example 3 but using a PEG4 linker in the SMCC in order to improve water solubility of the conjugate and scaled up to 40 mg of CLPTM1 antibody 59D04 IgG2a. A drug antibody ratio of 3.7 was achieved for the 59D04-DM1 conjugate.
In Vivo Models
A B16-F10 efficacy study was performed by Oncodesign (Montreal, Canada). 5 groups with 8 animals in each comprised: 1) Isotype IgG2a (C1.18.4 BioXcell). 2) 59D04-DM1, 3) 59D04-DM1&aPD1 (RPM1-14, BioXcell), 4) aPD1, and 5) 59D04. Six doses where given at 100 ug i.v. each twice weekly for three weeks.

Antibody 59D04 is a fully human phage display derived antibody developed at Yumab (Germany) using a peptide target portion of CLPTM1 (LWRWQLYAAQSTKSPWN-FLGDELYEQSDEEQDSVKVALLETNP)(SEQ ID NO: 61) and screening on a naive antibody library. In vivo data generated using 59D04 was using a scFv-mouse IgG2a Fc version produced and purified by Icosagen (Estonia) in CHO cells.

Data in FIG. 12 shows a significant effect using the combination of 59D04-DM1 and anti-PD1 on tumour growth over isotype control. A summary of the data at day 20 of the study and p-value of a two-tailed T-test is shown in Table 2.

TABLE 2

Ttest for tumor size difference at day 20

|  | m^3 avg | m^3 stdev | vs isotype p-value | vs PD1 p-value |
|---|---|---|---|---|
| Isotype | 941 | 208 |  |  |
| 59D04-DM1 | 840 | 374 | 0.6335 |  |
| 59D04-DM1 & aPD1 | 485 | 292 | 0.0439 | 0.1811 |
| aPD1 | 883 | 482 | 0.8282 |  |
| 59D04 | 1167 | 935 | 0.6533 |  |

Example 10—Direct Activating Effect on Antigen Presenting Cells In Vitro by an Anti-CLPTM1 ADC Tubulin inhibitors can enhance the surface expression of T-cell co-stimulatory proteins CD80 and CD86. Both CD80 and CD86 are critical for cytotoxic T-cell activation. In vitro we derived M2 macrophages from a human donor using the protocol from Example 1 above. CLPTM1 expression was verified by flow cytometry using 59D04 antibody and shown in FIG. 13A. Isotype control staining (left peak) and staining with the 59D04 antibody (right peak) are shown.

On these same M2 macrophages, a dilution series of either Isotype control, none, 59D04 mouse IgG2a or 59D04-DM1 was added and incubated overnight. CD80 and CD86 expression was analyzed by flow cytometry and found to be increased only with the DM1 conjugated antibody (FIGS. 13B and C). No enhancement was seen with an isotype control antibody or the non-conjugated 569D04 mAb. These data illustrate the applicability of our antibody drug conjugate comprising an anti-CLPTM1 antibody coupled to a tubulin inhibitor to stimulate antigen presenting cells in the tumor microenvironment and thereby enhance tumor cell killing by the immune system.

Example 11—Antibody Internalization into Cells for ADC

Human CD14 cells were isolated according to standard protocols and cultured. A set of anti-CLPTM1 antibodies were coupled to phRodo (ThermoFisher). This dye fluoresces at low pH. Antibodies carrying phRodo that are internalized and transported to the lysosome compartments inside cells for protein degradation are thus transported to an environment of low pH making the dye brighter. The CLPTM1 antibody 59D04 as either mouse IgG1 or IgG2a chimera was conjugated and compared to an isotype control antibody and Santa Cruz G7. Flow cytometry data shown in FIG. 14 are from a 5 hour incubation. These antibodies capable of internalization and degradation by transport to endosomes/lysosomes are especially suited as antibody drug conjugates where the drug effect requires free drug to be released from the link to the antibody such as a covalent link between DM1 and the antibody.

Example 12—Anti-CLPTM1 Antibody Generation

Mouse monoclonal antibody 7G12 was raised against a CLTPM1 synthetic peptide PWNFLGDELYEQSDE (SEQ ID NO: 40) using Rapid-Prime™ method by ImmunoPrecise (Victoria, Canada).

Antibody 59D04 is a fully human phage display derived antibody developed at Yumab (Germany) using a peptide target portion of CLPTM1

(SEQ ID NO: 61)
(LWRWQLYAAQSTKSPWNFLGDELYEQSDEEQDSVKVALLETNP)

and screening on a naive antibody library.

Variable heavy sequence of 59D04 is (SEQ ID NO: 59)
EVQLVESGGGVVQPGRSLRLSCAASGFTFSTYAMHWVRQAPGKGLEWVAV

ISYDGTNKYYADSVKGRFTIFRDNSKNTLYLQMNSLRAEDTAVYYCGSGS

YWGQGTLVTVSS

Variable light sequence of 59D04 is (SEQ ID NO: 60)
QPVLTQPASVSGSPGQSITISCTGTSSDVGGYNYVSWYQQHPGKAPKLMI

YEVTNRPSGVSDRFSGSKSGNTASLTISGLQAEDEADYYCSSYKSSNTVV

FGGGTKVTVL

Variable heavy sequence of 7G12 (IgG1 isotype) is (SEQ ID NO: 62)
QVQLQQSGTELVRPGTSVKVSCKASGYAFTNYLIEWVKQRPGQGLEWIGV

INPGSGGTRYNEKFKGKATLTADKSSTTAHMQLSSLTSDDSAVYCARWGG

NYSGYAMDYWGQGTSVTVSS

Variable light sequence of 7G12 (Kappa isotype) is (SEQ ID NO: 63)
QIVLTQSPVIMSASPGEKVTITCSASSSVSYMHWFQQKPGTSPKLWIYST

SNLASGVPARFSGSGSGTSYSLTISRMEAEDAATYYCQQRSSYPPTFGAG

TKL.

The CDRs of the 7G12 antibody are shown in SEQ ID NOs: 66-71, and the CDRs for the 59D04 antibody are shown in SEQ ID NOs: 72-77.

Consensus DNA sequences encoding the heavy and light chains for 7G12 are provided as SEQ ID NOs: 64 and 65, respectively.

Example 13—Antibody Affinity Determination

Affinity of antibodies was determined by finding the half-maximal binding on the native target in a flow cytometry assay. Since the native target is found inside most cells and rarely on the cell surface, the assay was performed using plasma membrane-permeabilised cells, an intra-cellular staining protocol. Using the native target is more applicable when evaluating and comparing various antibodies as it is the true antigen to be bound in a therapeutic setting in vivo. 0-876 cells were permeabilised with BD-fix and permeabilisation buffer (554722 BD-Biosciences). Antibody at various concentrations was incubated with cells for 30 minutes at +4° C., then washed twice with wash buffer (BD-Biosciences 554723). Secondary antibodies a-mouse IgG-PE (Molecular Probes) was used for mouse monoclonal antibodies according to manufacturer's instructions and a-rabbit-IgG-PE (Molecular Probes) for rabbit monoclonal antibody (Abcam ERP8800). Three washes followed and fluorescence intensity in cells was quantified by FACS CantoII in PBS with cells in 2% FCS buffer.

7G12 had the greatest affinity showing more than having half maximal binding (Flow Signal) at 0.1 µg/mL suggesting a Kd (as defined by half maximal binding) below 1 nM. The assay was performed on O-876 cancer cell line. Binding data are shown in FIG. 15. Antibodies 7G12, 59D04 and the Abcam antibody showed more half maximal binding at 1 µg/mL.

The Abcam antibody against CLPTM1 has reported affinity according to Biacore data supplied by the manufacturer of 0.0345 nM Kd. This was derived on a non-native recombinant portion of the antigen as test.

Of these antibodies 59D04 showed internalisation (Example 11, FIG. 17). The Santa Cruz mAb was not internalised.

Example 14—4T1 Breast Cancer Model of Metastasis

The syngeneic orthotopic breast cancer model 4T1 in mouse spontaneously metastasises to the lung. At the end of a study, the number of metastases can be counted. A study at Oncodesign (Montreal, Canada) was conducted using the same groups and treatments as for the B16 melanoma study in Example 9 using 59D04-DM1. Animals were treated with 100 ug i.v. of substances twice weekly for three weeks. At the end of the study, the groups had no statistically significant change in primary tumour size but the number of lung metastases was affected by both 59D04-mouse IgG2a-Fc and 59D04-DM1 compared to the isotype antibody control. Primary tumour sizes are plotted for each animal in FIG. 16A as well as the number of metastases counted in the lungs in FIG. 16B.

Our cancer tissue microarray data has indicated that in general metastases have higher surface expression of CLPTM1 compared to primary tumours.

Table 3 shows the significance of the treatment groups on lung metastases.

TABLE 3

| | metastases | p-value (2-sided Ttest) | |
|---|---|---|---|
| | # of, average | vs. isotype | vs. aPD1 |
| Isotype | 55.5 | | |
| 59D04-DM1 | 17.6 | 0.000036 | |
| 59D04-DM1 & aPD1 | 24.3 | 0.000188 | 0.078975 |
| aPD1 | 41.6 | 0.077617 | |
| 59D04 IgG2a | 34.5 | 0.023511 | |

The invention claimed is:
1. A product comprising:
(a) a therapeutic agent capable of binding to CLPTM1 at the surface of a cell and inhibiting the growth and/or viability of said cell; and
(b) an immune checkpoint inhibitor, the immune checkpoint inhibitor being an antibody which binds to an immune checkpoint protein or to a receptor for an immune checkpoint protein;
wherein said therapeutic agent and said immune checkpoint inhibitor are formulated for combined administration separately, sequentially or simultaneously, and wherein the therapeutic agent is selected from:
(i) an antibody having immune effector function selected from antibody dependent cell-mediated cytotoxicity (ADCC), antibody dependent cell-mediated phagocytosis (ADCP), and/or complement dependent cytotoxicity (CDC); and
(ii) a conjugate comprising an antibody conjugated to a cytotoxic or cytostatic drug, wherein said antibody is capable of being internalized by the cell,
wherein said antibody in said therapeutic agent is capable of binding to CLPTM1 and comprises the complementarity-determining regions (CDRs) VLCDR1, VLCDR2, VLCDR3, VHCDR1, VHCDR2 and VHCDR3, and wherein
(i) each of said CDRs has an amino acid sequence as follows:
VLCDR1 has the sequence set forth in SEQ ID NO: 66;
VLCDR2 has the sequence set forth in SEQ ID NO: 67;
VLCDR3 has the sequence set forth in SEQ ID NO: 68;
VHCDR1 has the sequence set forth in SEQ ID NO: 69;
VHCDR2 has the sequence set forth in SEQ ID NO: 70; and
VHCDR3 has the sequence set forth in SEQ ID NO: 71;
or
(ii) each of said CDRs has an amino acid sequence as follows:
VLCDR1 has the sequence set forth in SEQ ID NO: 72;
VLCDR2 has the sequence set forth in SEQ ID NO: 73;
VLCDR3 has the sequence set forth in SEQ ID NO: 74;
VHCDR1 has the sequence set forth in SEQ ID NO: 75;
VHCDR2 has the sequence set forth in SEQ ID NO: 76; and
VHCDR3 has the sequence set forth in SEQ ID NO: 77.
2. The product of claim 1, wherein
the therapeutic agent is capable of inhibiting the growth and/or viability of an anti-inflammatory and/or immunosuppressive cell to relieve unwanted or deleterious immunosuppression by eliminating anti-inflammatory and/or immunosuppressive immune cells; and/or
wherein the immune checkpoint inhibitor is an anti-PD1, anti-PDL1 or an anti-CTLA-4 antibody.
3. The product of claim 1 wherein the therapeutic agent is a conjugate comprising the antibody conjugated to a tubulin inhibitor.
4. A therapeutic agent capable of binding to CLPTM1 at the surface of an immune cell and modulating its activity, wherein
(i) the therapeutic agent is capable of inhibiting the growth and/or viability of an anti-inflammatory and/or immunosuppressive cell; and/or
(ii) the therapeutic agent is capable of stimulating an antigen-presenting immune cell;
wherein each said therapeutic agent (i) and (ii) is a conjugate comprising an antibody capable of binding to CLPTM1, conjugated to a drug; and
wherein said antibody comprises the complementarity-determining regions (CDRs) VLCDR1, VLCDR2, VLCDR3, VHCDR1, VHCDR2 and VHCDR3, wherein
(i) each of said CDRs has an amino acid sequence as follows:
VLCDR1 has the sequence set forth in SEQ ID NO: 66;
VLCDR2 has the sequence set forth in SEQ ID NO: 67;
VLCDR3 has the sequence set forth in SEQ ID NO: 68;
VHCDR1 has the sequence set forth in SEQ ID NO: 69;
VHCDR2 has the sequence set forth in SEQ ID NO: 70; and
VHCDR3 has the sequence set forth in SEQ ID NO: 71;
or
(ii) each of said CDRs has an amino acid sequence as follows:
VLCDR1 has the sequence set forth in SEQ ID NO: 72;
VLCDR2 has the sequence set forth in SEQ ID NO: 73;
VLCDR3 has the sequence set forth in SEQ ID NO: 74;
VHCDR1 has the sequence set forth in SEQ ID NO: 75;
VHCDR2 has the sequence set forth in SEQ ID NO: 76; and
VHCDR3 has the sequence set forth in SEQ ID NO: 77.
5. The product of claim 1, wherein said antibody in said therapeutic agent is:
(i) a half-molecule antibody fragment;
(ii) a single-chain antibody;
(iii) an afucosylated monoclonal antibody;
(iv) a humanised or chimeric antibody; or
(v) a human antibody.
6. The product of claim 1, wherein in said conjugate of part (ii), said drug is a radioisotope or a toxin or a small molecule compound or a chemotherapy drug.
7. The product of claim 6, wherein said drug is (i) a maytansinoid, or (ii) mertansine, emtansine or monomethyl auristatin E(MMAE).
8. The product of claim 1, wherein
said therapeutic agent is capable of inhibiting the growth and/or viability of an anti-inflammatory and/or immunosuppressive cell selected from or including:
(i) immunosuppressive immune cells;
(ii) tumour-infiltrating lymphocytes;
(iii) Treg or macrophage cells; or
(iv) M2 macrophage cells.
9. The product of claim 1, wherein said checkpoint inhibitor is an antibody against PDL-1, PD-1, CTLA4, TIM3, CD137, CD223, or phosphatidylserine.
10. A method of treating melanoma or breast cancer in a subject, or reducing cancer metastasis to the lung in a subject, said method comprising administering to said subject a therapeutically effective amount of the product of claim 1.
11. The method of claim 10, wherein said therapeutic agent is the antibody having immune effector function.
12. The method of claim 10, wherein the antibody is IgG.
13. The method of claim 12, wherein said IgG is IgG1 or IgG3.
14. The method of claim 10, wherein said therapeutic agent is the conjugate comprising an antibody capable of binding to CLPTM1 conjugated to a cytotoxic or cytostatic drug, optionally wherein the antibody is conjugated to the drug by a linker.
15. The method of claim 10, wherein said antibody is:
(i) a half-molecule antibody fragment;
(ii) a single-chain antibody;
(iii) an afucosylated monoclonal antibody;
(iv) a humanised or chimeric antibody; or
(v) a human antibody.

16. The method of claim 14, wherein said drug is a radioisotope or a toxin or a small molecule compound or a chemotherapy drug.

17. The method of claim 16, wherein said drug is (i) a tubulin inhibitor; (ii) a maytansinoid, or (iii) mertansine, emtansine or monomethyl auristatin E (MMAE).

18. The method of claim 10, wherein
(a) said therapeutic agent is capable of inhibiting the growth and/or viability of an anti-inflammatory and/or immunosuppressive cell selected from or including:
(i) immunosuppressive immune cells;
(ii) tumour-infiltrating lymphocytes;
(iii) Treg or macrophage cells; or
(iv) M2 macrophage cells.

19. The method of claim 18, wherein the immune checkpoint inhibitor is an anti-PD1, anti-PDL1 or an anti-CTLA-4 antibody.

20. A product comprising:
(a) a therapeutic agent capable of binding to CLPTM1 at the surface of antigen-presenting cells (APC) selected from dendritic cells and macrophage cells and stimulating said APC to activate an immune response; and
(b) an immune checkpoint inhibitor, being an antibody which binds to an immune checkpoint protein, or to a receptor for an immune checkpoint protein;
wherein said therapeutic agent and said immune checkpoint inhibitor are formulated for combined administration separately, sequentially or simultaneously;
and wherein the therapeutic agent is an antibody-drug conjugate (ADC) wherein the drug comprises a tubulin inhibitor and the antibody is capable of binding specifically to CLPTM1 and comprises the complementarity-determining regions (CDRs) VLCDR1, VLCDR2, VLCDR3, VHCDR1, VHCDR2 and VHCDR3, wherein (i) each of said CDRs has an amino acid sequence as follows:
VLCDR1 has the sequence set forth in SEQ ID NO: 66;
VLCDR2 has the sequence set forth in SEQ ID NO: 67;
VLCDR3 has the sequence set forth in SEQ ID NO: 68;
VHCDR1 has the sequence set forth in SEQ ID NO: 69;
VHCDR2 has the sequence set forth in SEQ ID NO: 70; and
VHCDR3 has the sequence set forth in SEQ ID NO: 71; or
(ii) each of said CDRs has an amino acid sequence as follows:
VLCDR1 has the sequence set forth in SEQ ID NO: 72;
VLCDR2 has the sequence set forth in SEQ ID NO: 73;
VLCDR3 has the sequence set forth in SEQ ID NO: 74;
VHCDR1 has the sequence set forth in SEQ ID NO: 75;
VHCDR2 has the sequence set forth in SEQ ID NO: 76; and
VHCDR3 has the sequence set forth in SEQ ID NO: 77.

21. A method of treating melanoma or breast cancer in a subject, or reducing cancer metastasis to the lung in a subject, said method comprising administering to said subject a therapeutically effective amount of the product of claim 20.

22. A method of modulating the immune system within a tumor microenvironment in a subject, said method comprising administering to the subject a therapeutically effective amount of the product of claim 1.

23. A method of modulating the immune system within a tumor microenvironment in a subject, said method comprising administering to the subject a therapeutically effective amount of the product of claim 20.

24. The product of claim 20, wherein said tubulin inhibitor is (i) a maytansinoid, or (ii) mertansine, emtansine or monomethyl auristatin E.

* * * * *